(12) United States Patent
Elmaanaoui

(10) Patent No.: US 12,277,731 B2
(45) Date of Patent: Apr. 15, 2025

(54) METHODS AND SYSTEMS FOR SYSTEM SELF-DIAGNOSIS

(71) Applicant: Canon U.S.A., Inc., Melville, NY (US)

(72) Inventor: Badr Elmaanaoui, Belmont, MA (US)

(73) Assignee: CANON U.S.A., INC., Melville, NY (US)

(*) Notice: Subject to any disclaimer, the term of this patent is extended or adjusted under 35 U.S.C. 154(b) by 301 days.

(21) Appl. No.: 17/870,681

(22) Filed: Jul. 21, 2022

(65) Prior Publication Data
US 2024/0029305 A1 Jan. 25, 2024

(51) Int. Cl.
*G06T 7/80* (2017.01)
*G01B 9/02055* (2022.01)
(Continued)

(52) U.S. Cl.
CPC ............ *G06T 7/80* (2017.01); *G01B 9/02072* (2013.04); *G01B 9/02091* (2013.01); *G06T 7/0012* (2013.01); *G06T 2207/10101* (2013.01)

(58) Field of Classification Search
CPC ......... G06T 2207/30041; G06T 19/006; G06T 2207/10024; G06T 2207/10148;
(Continued)

(56) References Cited

U.S. PATENT DOCUMENTS 4,379,633 A * 4/1983 Bickel ...................... G01H 9/00
73/657
6,763,261 B2 7/2004 Casscells, III et al.
(Continued)

FOREIGN PATENT DOCUMENTS

CN 107646087 A * 1/2018 ............ B21D 11/10
EP 3831279 A1 * 6/2021 ........... A61B 5/0066
(Continued)

OTHER PUBLICATIONS

Marco Ruggeri, et al., "Imaging and full-length biometry of the eye during accommodation using spectral domain OCT with an optical switch", Biomedical Optics Express, vol. 3, No. 7, Jul. 2012, pp. 1506-1520.

*Primary Examiner* — Michael P Stafira
(74) *Attorney, Agent, or Firm* — CANON U.S.A., INC. IP DIVISION

(57) ABSTRACT

One or more devices, systems, methods, and storage mediums for performing self-diagnosis using one or more imaging modalities are provided herein. Examples of applications include imaging, evaluating and diagnosing biological objects, such as, but not limited to, for Gastro-intestinal, cardio and/or ophthalmic applications, and being obtained via one or more optical instruments, such as, but not limited to, optical probes, catheters, capsules and needles (e.g., a biopsy needle). Devices, systems, methods, and storage mediums may include or involve a method, such as, but not limited to, for determining status or health (such as optical health) of a rotary joint of an apparatus/system and/or of the apparatus/system. A device, system, method, or storage medium may perform self-diagnosis or diagnosis to minimize, reduce, and/or avoid optical failures, rotary joint failures, or apparatus/system failures and to have a robust method(s) of determining the health of the rotary joint and/or the apparatus or system.

31 Claims, 14 Drawing Sheets

(51) Int. Cl.
*G01B 9/02091* (2022.01)
*G06T 7/00* (2017.01)

(58) Field of Classification Search
CPC . G06T 2207/10152; G06T 2207/10101; G06T 7/0012; G06T 7/0014; G06T 2200/24; G06T 2207/30104; G06T 11/003; G06T 2207/10028; G06T 2207/30101; G06T 7/0016; G06T 7/246; G06T 7/337; G06T 7/74; G06T 15/08; G06T 2207/20036; G06T 2210/41; G06T 2207/20182; G06T 2207/10068; G06T 2207/30021; G06T 5/70; G06T 7/12; G06T 7/13; G06T 2207/10056; G06T 2207/30028; G06T 2207/20081; G06T 2207/20084; G06T 2207/20096; G06T 2207/30024; G06T 3/40; G06T 5/40; G06T 7/11; G06T 7/30; G06T 7/33; G06T 7/62; G06T 2207/10064; G06T 2207/20028; G06T 2207/20076; G06T 2207/20101; G06T 2207/30004; G06T 7/136; G06T 7/149; G06T 7/168; G06T 7/80; G01B 9/02091; G01B 9/02044; G01B 2290/70; G01B 9/02007; G01B 9/0203; G01B 9/0209; G01B 9/02004; G01B 9/02083; G01B 9/02084; G01B 9/02087; G01B 9/02002; G01B 9/02057; G01B 2290/65; G01B 9/02069; G01B 9/02078; G01B 9/02011; G01B 2290/45; G01B 9/0201; G01B 9/02067; G01B 9/02072; G01B 9/02077; G01B 9/02063; G01B 2290/60; G01B 9/02012; G01B 9/02071; G01B 11/2441; G01B 9/02043; G01B 9/02049; G01B 9/0205; G01B 2290/35; G01B 9/02027; G01B 9/02079; G01B 9/04; G01B 9/02028; G01B 9/02032; G01B 9/02034; G01B 9/02037; G01B 11/00; G01B 11/026; G01B 11/06; G01B 11/12; G01B 9/02047; G01B 9/02014; G01B 9/02041; G01B 9/02058; G01B 9/02064; G01B 9/0207; G01B 9/02081; G01B 9/02085; G01B 9/02097; G01B 9/02015; G01B 11/18; G01B 11/24; G01B 9/02005; G01B 9/02009; G01B 9/02019; G01B 9/02022; G01B 9/02025; G01B 9/02048; G01B 9/02074; G01B 9/02082

See application file for complete search history.

(56) References Cited

U.S. PATENT DOCUMENTS

| | | | |
|---|---|---|---|
| 7,366,376 B2 | 4/2008 | Shishkov | |
| 7,843,572 B2 | 11/2010 | Tearney et al. | |
| 7,872,759 B2 | 1/2011 | Tearney et al. | |
| 7,889,348 B2 | 2/2011 | Tearney et al. | |
| 8,289,522 B2 | 10/2012 | Tearney et al. | |
| 8,676,013 B2 | 3/2014 | Bouma et al. | |
| 8,928,889 B2 | 1/2015 | Tearney et al. | |
| 9,086,264 B2 * | 7/2015 | Wang | G01N 21/4795 |
| 9,087,368 B2 | 7/2015 | Tearney et al. | |
| 9,332,942 B2 | 5/2016 | Jaffer et al. | |
| 9,557,154 B2 | 1/2017 | Tearney et al. | |
| 9,795,301 B2 | 10/2017 | Fleming et al. | |
| 9,869,828 B2 | 1/2018 | Altshuler | |
| 10,323,926 B2 | 6/2019 | Elmaanaoui | |
| 10,558,001 B2 | 2/2020 | Altshuler et al. | |
| 10,601,173 B2 | 3/2020 | Altshuler | |
| 10,606,064 B2 | 3/2020 | Wu | |
| 10,743,749 B2 | 8/2020 | Yamada | |
| 10,884,199 B2 | 1/2021 | Altshuler et al. | |
| 10,895,692 B2 | 1/2021 | Yamada | |
| 10,912,462 B2 | 2/2021 | Wang et al. | |
| 11,175,126 B2 | 11/2021 | Elmaanaoui et al. | |
| 2008/0170231 A1 * | 7/2008 | Ressler | G01J 3/0202 356/451 |
| 2010/0092389 A1 | 4/2010 | Jaffer | |
| 2011/0292400 A1 | 12/2011 | Fleming et al. | |
| 2012/0101374 A1 | 4/2012 | Tearney et al. | |
| 2014/0276011 A1 | 9/2014 | Schmitt et al. | |
| 2016/0228097 A1 | 8/2016 | Jaffer et al. | |
| 2017/0135584 A1 | 5/2017 | Tearney et al. | |
| 2018/0003481 A1 * | 1/2018 | Yamada | A61B 5/6852 |
| 2018/0045501 A1 * | 2/2018 | Elmaanaoui | G01B 9/02091 |
| 2018/0372477 A1 * | 12/2018 | Elmaanaoui | G01B 9/02091 |
| 2019/0150720 A1 * | 5/2019 | Altshuler | A61B 1/07 |
| 2019/0254506 A1 | 8/2019 | Hamm et al. | |
| 2019/0374109 A1 * | 12/2019 | Wu | G06T 11/008 |
| 2020/0318944 A1 * | 10/2020 | Elmaanaoui | G01B 9/02068 |
| 2020/0390323 A1 | 12/2020 | Yamada | |
| 2021/0077037 A1 | 3/2021 | Kunio | |
| 2021/0121132 A1 | 4/2021 | Watanabe et al. | |
| 2021/0174125 A1 | 6/2021 | Zhang | |
| 2021/0407098 A1 * | 12/2021 | Athanasiou | A61B 5/6852 |
| 2022/0040454 A1 | 2/2022 | Hamm et al. | |
| 2022/0042781 A1 * | 2/2022 | Yamada | G01B 9/02044 |
| 2022/0042783 A1 * | 2/2022 | Elmaanaoui | G06T 7/33 |
| 2022/0044428 A1 | 2/2022 | Elmaanaoui et al. | |
| 2022/0104786 A1 * | 4/2022 | Kunio | A61B 6/463 |
| 2023/0108133 A1 * | 4/2023 | Kunio | A61B 5/0084 600/300 |

FOREIGN PATENT DOCUMENTS

| | | | | |
|---|---|---|---|---|
| EP | 3949835 A2 | * | 2/2022 | A61B 5/0033 |
| JP | 4477230 B2 | * | 6/2010 | A61B 10/06 |
| JP | 2020018840 A | * | 2/2020 | A61B 5/0066 |
| WO | 2016015052 A1 | | 1/2016 | |
| WO | 20160144878 A1 | | 9/2016 | |
| WO | WO-2019222616 A1 | * | 11/2019 | A61B 3/102 |
| WO | WO-2020159984 A1 | * | 8/2020 | A61B 6/12 |
| WO | 2021055837 A1 | | 3/2021 | |

* cited by examiner

METHODS AND SYSTEMS FOR SYSTEM SELF-DIAGNOSIS

FIELD OF THE INVENTION

The present disclosure generally relates to computer imaging, computer vision, and/or to the field of medical and/or optical imaging, particularly to devices/apparatuses, systems, methods, and storage mediums, that employ attachment of rotatable optical probe(s) to imaging device(s) and/or for using one or more imaging modalities, including but not limited to, angiography, Optical Coherence Tomography (OCT), Multi-modality OCT (MM-OCT), near-infrared fluorescence (NIRF), near-infrared auto-fluorescence (NIRAF), OCT-NIRAF, robot imaging, snake robot imaging, etc. Examples of OCT applications include imaging, evaluating, and diagnosing biological objects, including, but not limited to, for gastro-intestinal, pulmonary, cardio, ophthalmic, and/or intravascular applications, and being obtained via one or more optical instruments, including but not limited to, one or more optical probes, one or more catheters, one or more endoscopes, one or more capsules (e.g., one or more tethered capsules), and one or more needles (e.g., a biopsy needle). One or more devices, systems, methods, and storage mediums for characterizing, examining and/or diagnosing, and/or measuring viscosity of, a sample or object in system self-diagnosis application(s) using an apparatus or system that uses and/or controls one or more imaging modalities are discussed herein.

BACKGROUND OF THE INVENTION

Intraluminal imaging aims to acquire high resolution cross-sectional images of biological tissue and non-biological materials, and enables real time visualization. Intraluminal imaging usually requires rotation of an optical probe and a rotatable section of a system rotary joint. A section of the rotary joint is static. A health or quality of a rotary joint throughput and of back-reflections has to be adequate and a status of the rotary joint health or quality should be known in order for a device or system to properly function and in order to determine whether servicing is required before wasting usually single-use expensive probes. Performing a case or application with the device or system when the rotary joint health is not at an acceptable level would yield useless data, cause a delay in procedure, and result in wasted physician time. More importantly, performing a case or application with the device or system when the rotary joint health is not at an acceptable level may cause undue harm to an object to be imaged, a specimen or target, or a patient.

Fiber optic catheters and endoscopes have been developed to gain access to internal organs. For example, in cardiology OCT (Optical Coherence Tomography) has been developed to capture and visualize depth-resolved images of vessels with a catheter. The catheter, which may include a sheath, a coil and an optical probe, may be navigated to a coronary artery.

Optical coherence tomography (OCT) is a technique for obtaining high-resolution cross-sectional images of tissues or materials, and enables real time visualization. The aim of the OCT techniques is to measure the time delay of light by using an interference optical system or interferometry, such as via Fourier Transform or Michelson interferometers. Light from a light source delivers and splits into a reference arm and a sample (or measurement) arm with a splitter (e.g., a beamsplitter). A reference beam is reflected from a reference mirror (partially reflecting or other reflecting element) in the reference arm while a sample beam is reflected or scattered from a sample in the sample arm. Both beams combine (or are recombined) at the splitter and generate interference patterns. The output of the interferometer is detected with one or more detectors, such as, but not limited to, photodiodes or multi-array cameras, in one or more devices, such as, but not limited to, a spectrometer (e.g., a Fourier Transform infrared spectrometer). The interference patterns are generated when the path length of the sample arm matches that of the reference arm to within the coherence length of the light source. By evaluating the output beam, a spectrum of an input radiation may be derived as a function of frequency. The frequency of the interference patterns corresponds to the distance between the sample arm and the reference arm. The higher frequencies are, the greater are the differences in path length. Single mode fibers may be used for OCT optical probes, and double clad fibers may be used for fluorescence and/or spectroscopy.

A multi-modality system, such as, but not limited to, an OCT, fluorescence, and/or spectroscopy system with an optical probe, is developed to obtain multiple information at the same time. During vascular diagnosis and intervention procedures, such as Percutaneous Coronary Intervention (PCI), users of optical coherence tomography (OCT) sometimes have difficulty understanding the tomography image in correlation with other modalities because of an overload of information, which causes confusion in image interpretation.

Percutaneous coronary intervention (PCI), and other vascular diagnosis and intervention procedures, have improved with the introduction of intravascular imaging (IVI) modalities, such as, but not limited to, intravascular ultrasound (IVUS) and optical coherence tomography (OCT). IVI modalities provide cross-sectional imaging of coronary arteries with precise lesion information (e.g., lumen size, plaque morphology, implanted devices, etc.). That said, only about 20% of interventional cardiologists in the United States use IVI imaging in conjunction with coronary angiography during PCI procedures. Additionally, IVI imaging uses the rotation of usually disposable single-use sterile catheters or probes to non-disposable imaging systems. Having the imaging system(s) be fully rotatable is not feasible and, as such, in the case of optical interferometric imaging like OCT, either the full catheter core is rotated from its proximal section at an interface with the imaging system or a motor is placed distally to perform the rotation. Performing rotation distally has its limitations and that is why most systems opt for proximal rotation using a rotary joint. Detecting, monitoring, and confirming coupling at the rotary joint is desirable to identify health of the rotary joint and system performance, and to reduce procedure delay and user frustration (e.g., by detecting and monitoring rotary joint health and the system performance to avoid initiating a case, application, or use with an improperly operating system, the system may prevent such delay and frustration).

Interferometry methods such as OFDR (Optical Frequency Domain Reflectometer) and OTDR (Optical Time Domain Reflectometer) are used in telecom networks to measure insertion loss and return loss from fiber optic interfaces. The drawback of such methods is that these methods require specialized complex hardware to measure insertion loss and/or return loss signals from interfaces. Additionally, these methods are not used to determine rotary joint optical health since these methods are slow and require completely different instrumentation.

Another method may potentially check reflections at the distal tip of the optical probe. However, this method does not guarantee knowledge of rotary joint health since a strength of the reflections from the probe may not be necessarily known a priori. Such a method is further deficient because the method is not specific enough to pinpoint whether the issue(s) is/are in the probe or earlier in the system (even if the probe reflection strength is arguably known). This method also suffers from the fact that the user may have to scrap an otherwise good sterile single-use probe since the issue(s) is/are only identified after the probe is mated to the system.

Accordingly, it would be desirable to provide at least one imaging or optical apparatus/device, system, method, and storage medium that applies self-diagnosis techniques. It also would be desirable to provide one or more imaging or optical apparatuses/devices, systems, methods, and storage mediums that operate to determine rotary joint health and device/system health using one or more self-diagnosis techniques at high efficiency and a reasonable cost of manufacture and maintenance.

SUMMARY OF THE INVENTION

Accordingly, it is a broad object of the present disclosure to provide imaging (e.g., OCT, IVI, IVUS, NIRF, NIRAF, SNAKE robots, robots, etc.) apparatuses, systems, methods, and storage mediums for using and/or controlling one or more multiple imaging modalities, that apply self-diagnosis techniques, and that use the results to determine rotary joint health and device/system health. It is also a broad object of the present disclosure to provide OCT devices, systems, methods, and storage mediums using an interference optical system, such as an interferometer (e.g., spectral-domain OCT (SD-OCT), swept-source OCT (SS-OCT), multimodal OCT (MM-OCT), Intravascular Ultrasound (IVUS), Near-Infrared Autofluorescence (NIRAF), Near-Infrared Spectroscopy (NIRS), Near-Infrared Fluorescence (NIRF), therapy modality using light, sound, or other source of radiation, etc.), that may use self-diagnosis techniques discussed herein.

One or more methods, medical imaging devices, Intravascular Ultrasound (IVUS) or Optical Coherence Tomography (OCT) devices, imaging systems, and/or computer-readable storage mediums for performing self-diagnosis may be employed in one or more embodiments of the present disclosure to avoid the aforementioned issues. One or more embodiments may provide a simple and fast method or methods that uses/use techniques and structure to determine rotary joint health and system health using light throughput, system sensitivity, and resolution. Knowledge of rotary junction health and/or device/system optical health may be used to communicate device/system status and to allow or block specific device/system functionality. In one or more embodiments, a test to evaluate rotary joint health and/or device/system health may be performed as part of a power-on self-test.

One or more features of the self-diagnosis techniques discussed in the present disclosure may be employed or exercised using any OCT device/system and may operate with minor modification(s) to the reference arm. For example, in one or more embodiments, a single reference arm path may be used. In one or more other self-diagnosis method embodiments discussed herein, a system or device may employ two reference arm paths or a sufficiently long single reference arm path that operates to adjust an imaging Field of View (FOV) to be at a primary or main sample or imaging object and/or at a rotary joint/junction location.

One or more embodiments may obtain a direct analysis of self-diagnosis techniques, and that use the results to determine rotary joint health and device/system health, using at least one reliable optical interference signal. One or more embodiments may operate with or without prior knowledge of reflection strength(s) from probe/catheter distal reflections, and preferably do not require such knowledge of the reflection strength(s).

Other broad objects of the present disclosure include, but are not limited to, minimizing, reducing, and/or avoiding rotary joint and/or device/system failures and having a robust means of determining status of a rotary joint and/or device/system (e.g., an imaging apparatus, an imaging system, a medical apparatus, a medical system, etc.).

One or more embodiments of the present disclosure may use an OCT signal at a patient interface unit (PIU) output connector to determine rotary joint and/or system/device status, and/or may use an OCT signal about or for the PIU output connector and a catheter connector to perform one or more of the self-diagnosis techniques discussed herein (also referred to herein as an "self-diagnosis process" or "self-diagnosis processes").

In one or more embodiments of a self-diagnosis apparatus or system having one or more processors and having an intravascular imaging catheter, the one or more processors may operate to at least acquire or receive image data during a pullback operation of the intravascular imaging catheter.

One or more features of the present disclosure may be employed or exercised using any OCT apparatus and/or system, and may be done so using only minor modifications to the reference arm where an apparatus and/or system uses a single reference arm path, one or more embodiments of a method or technique of the present disclosure may use two reference arm paths or the ability to sufficiently adjust reference arm delay so as to adjust the imaging FOV to be at either the main sample imaging location or at about the system distal-most point (e.g., a location where the catheter/probe mates with the sample arm, the rotary joint of the PIU, or a location of a sacrificial interface, etc.).

In accordance with one or more embodiments of the present disclosure, apparatuses and systems, and methods and storage mediums for performing self-diagnosis may operate to characterize biological objects, such as, but not limited to, blood, mucus, tissue, etc. In one or more embodiments, the object or sample may include one or more of the following: a vessel, a target specimen or object, and a patient.

One or more embodiments of the present disclosure may be used in clinical application(s), such as, but not limited to, intervascular imaging, intravascular imaging, pulmonary imaging, atherosclerotic plaque assessment, cardiac stent evaluation, intracoronary imaging using blood clearing, balloon sinuplasty, sinus stenting, arthroscopy, ophthalmology, ear research, veterinary use and research, etc.

In accordance with at least another aspect of the present disclosure, one or more technique(s) discussed herein may be employed as or along with features to reduce the cost of at least one of manufacture and maintenance of the one or more apparatuses, devices, systems, and storage mediums by reducing or minimizing a number of optical and/or processing components and by virtue of the efficient techniques to cut down cost of use/manufacture of such apparatuses, devices, systems, and storage mediums.

The one or more processors may further operate to perform the coregistration by co-registering an acquired or received angiography image and an obtained one or more Optical Coherence Tomography (OCT) or Intravascular Ultrasound (IVUS) images or frames.

One or more embodiments of a non-transitory computer-readable storage medium storing at least one program for causing a computer to execute a method for performing device or system self-diagnosis may be used with any method(s) discussed in the present disclosure, including but not limited to, one or more catheter imaging method(s), one or more other self-diagnosis method(s), one or more detecting or detection method(s), etc.

One or more embodiments of any method discussed herein (e.g., self-diagnosis method(s), detecting method(s), imaging or visualization method(s), etc.) may be used with any feature or features of the apparatuses, systems, other methods, storage mediums, or other structures discussed herein.

One or more embodiments of the present disclosure may achieve the efficient catheter (or other imaging device) detection, the efficient determination and/or evaluation of rotary joint health and/or apparatus/system health, and/or efficient coregistration result(s) from image(s). In one or more embodiments, the image data may be acquired during intravascular imaging pullback using a catheter (or other imaging device) that may be visualized in an image.

In at least one further embodiment example, a method of 3D construction or reconstruction without adding any imaging requirements or conditions may be employed. One or more methods of the present disclosure may use intravascular imaging, e.g., IVUS, OCT, etc., and one (1) view of angiography. In the description below, while intravascular imaging of the present disclosure is not limited to OCT, OCT is used as a representative of intravascular imaging for describing one or more features herein.

One or more embodiments of an interferometry and/or Optical Coherence Tomography (OCT) apparatus or system may include any feature or combination or features discussed in the present disclosure. For example, one or more interferometry and/or OCT apparatuses or systems may operate to determine a health of one or more internal components of the interferometry and/or OCT system and/or to determine a health of the interferometry and/or OCT system. The one or more interferometry and/or OCT apparatuses or systems may include: an imaging apparatus or system using one or more imaging modalities; at least one reference reflection that operates so that a reflection from a portion of the one or more internal components of the interferometry and/or OCT system is visible in an observable imaging depth or in an imaging field of view; and one or more processors that operate to determine the health of the one or more internal components and/or the health of the interferometry and/or OCT system based on one or more interferometry signals and/or images. The interferometry and/or OCT apparatuses or systems may include a catheter or probe.

One or more interferometry and/or OCT apparatuses or systems may include internal components, where the one or more internal components may include one or more of the following: a mating part of the catheter or probe; a portion of the catheter or probe; a rotary joint of a Patient Interface Unit (PIU); a rotary joint of the interferometry and/or OCT system; a portion of the PIU; and/or a sacrificial interface in communication with a rotary joint of the interferometry and/or OCT system or in communication with the interferometry and/or OCT system.

One or more processors of one or more apparatuses or systems discussed herein may further operate to: switch the at least one reference reflection from a main reference arm to an auxiliary reference arm; and adjust the auxiliary reference arm such that one or more reflections from one or more optical surfaces of the rotary joint or of the one or more internal components are disposed or located in the observable imaging depth or in the imaging field of view. The one or more processors may further operate to determine the health of the one or more internal components and/or the health of the interferometry and/or OCT system, based on the one or more interferometry signals and/or the images, by characterizing or using one or more of the following: one or more return losses, a noise floor, one or more fixed pattern artifacts, and/or point spread functions (PSF) width. The one or more processors may further operate to: perform peak finding to identify one or more peaks related or relating to one of the following: (i) one or more return signals that return from one or more predetermined locations on the one or more internal components, a rotary joint of the one or more internal components, and/or the interferometry and/or OCT system; and/or (ii) the one or more interferometry signals and/or the images; and determine the health of the one or more internal components or the rotary joint of the interferometry and/or OCT system using the identified one or more peaks and/or determine the health of the interferometry and/or OCT system using the identified one or more peaks. The one or more processors may further operate to one or more of the following: (i) store the determined health of the one or more internal components or of a rotary joint of the one or more internal components and/or the determined health of the interferometry and/or OCT system in one or more memories; and/or (ii) display the determined health of the one or more internal components or of a rotary joint of the one or more internal components and/or the determined health of the interferometry and/or OCT system on a display of the interferometry and/or OCT system or on a display in communication with the interferometry and/or OCT system. In one or more embodiments in a case where a delay of an optical delay line is increased or adjusted so that a length of the main reference arm or of the auxiliary reference arm matches a length of a sample arm of the interferometry and/or OCT system and of a catheter or probe included, the interferometry and/or OCT system may operate or the one or more processors may operate to perform system imaging; or in a case where the delay is decreased or adjusted so that a length of the main reference arm or of the auxiliary reference arm matches a length of a sample arm of the interferometry and/or OCT system without the catheter or probe, the interferometry and/or OCT system may operate or the one or more processors may operate to perform imaging of a region of the one or more internal components, the rotary joint, or of one or more portions of the rotary joint or of the one or more internal components. The one or more processors may further operate to control one or more of the following: (i) a mechanical mating of a sacrificial interface of a rotary joint of the interferometry and/or OCT system, of the one or more internal components of the interferometry and/or OCT system, of a patient interface unit of the interferometry and/or OCT system, or of the interferometry and/or OCT system to a connector of a catheter or probe; and/or (ii) a mechanical de-mating of a connector of a catheter or probe from one of the following: a sacrificial interface of the rotary joint of the interferometry and/or OCT system, the one or more internal components of the interferometry and/or OCT system, a patient interface unit of the interferometry and/or OCT system, or the interferometry and/or OCT system.

In one or more embodiments, an interferometry and/or OCT apparatus or system may further include one of the following: (i) an optical delay line or an optical switch that operates such that the one or more processors switch the at least one reference reflection between the main reference arm and the auxiliary reference arm; (ii) an optical switch, wherein the at least one reference reflection comprises a main reflector for the main reference arm and an auxiliary reflector for the auxiliary reference arm, and the optical switch operates to switch between the main reflector of the main reference arm and the auxiliary reflector of the auxiliary reference arm; (iii) a 1×2 optical switch, wherein the at least one reference reflection comprises a main reflector for the main reference arm and an auxiliary reflector for the auxiliary reference arm, and the 1×2 optical switch operates to switch between the main reflector of the main reference arm and the auxiliary reflector of the auxiliary reference arm; (iv) an optical switch, wherein the at least one reference reflection comprises an optical delay line for the main reference arm and an auxiliary reflector for the auxiliary reference arm, the optical switch operates to switch between the optical delay line of the main reference arm and the auxiliary reflector of the auxiliary reference arm, and the optical delay line operates to adjust a length of the main reference arm to account for an optical probe or catheter with varying optical lengths; (v) an optical switch, wherein the at least one reference reflection comprises a main reflector for the main reference arm and an optical delay line for the auxiliary reference arm, the optical switch operates to switch between the main reflector of the main reference arm and the optical delay line of the auxiliary reference arm, and the optical delay line operates to adjust a length of the auxiliary reference arm to account for an optical probe or catheter with varying optical lengths; (vi) an optical switch and an optical delay line, wherein the at least one reference reflection comprises a main reflector for the main reference arm and an auxiliary reflector for the auxiliary reference arm, the optical switch operates to switch between the main reflector of the main reference arm and the auxiliary reflector of the auxiliary reference arm, and the optical delay line is in communication with the optical switch such that the optical delay line operates to adjust a length of the main reference arm and/or the auxiliary reference arm to account for a catheter or probe with a varying optical length and/or to address one or more manufacturing tolerances of the interferometry and/or OCT system or of a portion of the interferometry and/or OCT system; (vii) two optical switches in communication with each other in series, the two optical switches operating to define an auxiliary path portion of the auxiliary reference arm and a main path portion of the main reference arm, the two optical switches being in further communication with the at least one reference reflection or an optical delay line such that the auxiliary path or the main path is used for the reference reflection or the optical delay line; (viii) an optical switch and an optical delay line, wherein the at least one reference reflection comprises a main reflector for the main reference arm and an auxiliary reflector for the auxiliary reference arm, the optical switch operates to switch between the main reflector of the main reference arm and the auxiliary reflector of the auxiliary reference arm, the optical delay line is in communication with the optical switch such that the optical switch is disposed in between the optical delay line and the main and auxiliary reflectors, and the optical delay line operates to adjust a length of the main reference arm and/or the auxiliary reference arm; or (ix) an optical delay line and a light splitter, wherein the at least one reference reflection comprises a main reflector for the main reference arm and an auxiliary reflector for the auxiliary reference arm, the splitter operates to split light or one or more signals between the main reflector of the main reference arm and the auxiliary reflector of the auxiliary reference arm at the same time. In one or more embodiments, the interferometry and/or OCT apparatus or system may further include one or more of the following: (i) a 3-port circulator that is connected to or in communication with, or that operates to transmit one or more signals between, the following: a light source via a first port of the 3-port circulator, the main reference arm and/or the auxiliary reference arm via a second port of the 3-port circulator, and one or more detectors via a third port of the 3-port circulator; (ii) a 4-port circulator that is connected to or in communication with, or that operates to transmit one or more signals between, the following: a light source via a first port of the 4-port circulator, the main reference arm and/or the auxiliary reference arm via a second port of the 4-port circulator, one or more detectors via a third port of the 4-port circulator, and an optical delay line via a fourth port of the 4-port circulator; and/or (iii) another 3-port circulator connected to or included in a sample arm of the interferometry and/or OCT system, the other 3-port circulator being connected to or in communication with, or operating to transmit one or more signals between, the following: a light source via a first port of the another 3-port circulator, the rotary joint or a catheter or probe connected to the rotary joint via a second port of the another 3-port circulator, and one or more detectors via a third port of the another 3-port circulator. In one or more embodiments, an interferometry and/or OCT apparatus or system may further include a linear stage and a rotary motor, wherein the one or more processors further operate to move the linear stage and the rotary motor to one or more positions such that the reflection from the portion of the one or more internal components of the interferometry and/or OCT system is visible in the observable imaging depth or the imaging field of view.

In one or more embodiments, an interferometry and/or OCT apparatus or system may further include, or may be connected to, one or more of the following: (a) a light source that operates to produce a light; (b) an interference optical system that operates to: (i) receive and divide the light from the light source into a first light with which an object or sample is to be irradiated and a second reference light, (ii) send the second reference light for reflection off of a reference mirror of the interference optical system or off of the at least one reference reflection, and (iii) generate interference light by causing reflected or scattered light of the first light with which the object or sample has been irradiated and the reflected second reference light to combine or recombine, and to interfere, with each other, the interference light generating one or more interference patterns; and/or (c) an interference optical system and one or more detectors, the interference optical system operating to: (i) receive and divide the light from the light source into a first light with which an object or sample is to be irradiated and a second reference light, (ii) send the second reference light for reflection off of a reference mirror of the interference optical system or off of the at least one reference reflection, and (iii) generate interference light by causing reflected or scattered light of the first light with which the object or sample has been irradiated and the reflected second reference light to combine or recombine, and to interfere, with each other, the interference light generating one or more interference patterns, and the one or more detectors operating to continuously acquire the interference light and/or the one or more interference patterns such that the the one or more interferometry signals and/or the images is/are obtained.

In one or more embodiments, the one or more imaging modalities may include one or more of the following: Optical Coherence Tomography (OCT); another lumen image(s) modality; an intravascular imaging modality; an imaging modality for fluorescence; a near-infrared auto-fluorescence (NIRAF) imaging modality; a near-infrared auto-fluorescence (NIRAF) imaging modality in a predetermined view, a carpet view, and/or an indicator view; a near-infrared fluorescence (NIRF) imaging modality; a near-infrared fluorescence (NIRF) imaging modality in a predetermined view, a carpet view, and/or an indicator view; a three-dimensional (3D) rendering imaging modality; an imaging modality for a 3D rendering of a vessel; an imaging modality for a 3D rendering of a vessel in a half-pipe view or display; an imaging modality for a 3D rendering of an object, target, or specimen; an imaging modality for a lumen profile; an imaging modality for a lumen diameter display; an imaging modality for a longitudinal view; computer tomography (CT); Magnetic Resonance Imaging (MRI); Intravascular Ultrasound (IVUS); an imaging modality for an X-ray image or view; and an imaging modality for an angiography view.

One or more methods discussed herein may involve or include any feature(s) or combination of features or steps discussed in the present disclosure. For example, a method may be for determining a health of an interferometry and/or Optical Coherence Tomography (OCT) apparatus or system or one or more internal components of the interferometry and/or OCT apparatus or system, the interferometry and/or OCT apparatus or system comprising an imaging apparatus or system using one or more imaging modalities, and at least one reference reflection that operates so that a reflection from a portion of the one or more internal components of the interferometry and/or OCT apparatus or system is visible in an observable imaging depth or in an imaging field of view. In one or more embodimentse, a method for determining a health of an interferometry and/or Optical Coherence Tomography (OCT) apparatus or system or one or more internal components of the interferometry and/or OCT apparatus or system may include determining the health of the one or more internal components and/or the health of the interferometry and/or OCT apparatus or system based on one or more interferometry signals and/or images. In one or more embodiments, one or more of the following may occur or exist: the interferometry and/or OCT apparatus or system further includes a catheter or probe; and/or the one or more internal components includes one or more of the following: a mating part of the catheter or probe; a portion of the catheter or probe; a rotary joint of a Patient Interface Unit (PIU); a rotary joint of the interferometry and/or OCT apparatus or system; a portion of the PIU; and/or a sacrificial interface in communication with a rotary joint of the interferometry and/or OCT apparatus or system or in communication with the interferometry and/or OCT apparatus or system.

In one or more embodiments, the method for determining a health of an interferometry and/or Optical Coherence Tomography (OCT) apparatus or system or one or more internal components of the interferometry and/or OCT apparatus or system may further include: switching the at least one reference reflection from a main reference arm to an auxiliary reference arm; and adjusting the auxiliary reference arm such that one or more reflections from one or more optical surfaces of a rotary joint or of the one or more internal components are disposed or located in the observable imaging depth or in the imaging field of view. In one or more embodiments, the interferometry and/or OCT apparatus or system further operates to determine the health of the one or more internal components and/or the health of the interferometry and/or OCT apparatus or system, based on the one or more interferometry signals and/or the images, by characterizing or using one or more of the following: one or more return losses, a noise floor, one or more fixed pattern artifacts, and/or point spread functions (PSF) width. One or more methods may further include: performing peak finding to identify one or more peaks related or relating to one of the following: (i) one or more return signals that return from one or more predetermined locations on the one or more internal components, a rotary joint of the one or more internal components, and/or the interferometry and/or OCT apparatus/system; and/or (ii) the one or more interferometry signals and/or the images; and determining the health of the one or more internal components or the rotary joint of the interferometry and/or OCT apparatus or system using the identified one or more peaks and/or determining the health of the interferometry and/or OCT apparatus/system using the identified one or more peaks. One or more methods may further include one or more of the following: (i) storing the determined health of the one or more internal components or of a rotary joint of the one or more internal components and/or the determined health of the interferometry and/or OCT apparatus/system in one or more memories; and/or (ii) displaying the determined health of the one or more internal components or of a rotary joint of the one or more internal components and/or the determined health of the interferometry and/or OCT apparatus/system on a display of the interferometry and/or OCT apparatus/system or on a display in communication with the interferometry and/or OCT apparatus/system.

In one or more embodiments, the determining the health of the one or more internal components using the identified one or more peaks and/or the determining the health of the interferometry and/or OCT apparatus/system using the identified one or more peaks step may further include one or more of the following: (i) calculating a value of a selected peak or peaks of the identified one or more peaks and comparing the value of the selected peak or peaks to a measured a measured signal-to-noise ratio (SNR); (ii) calculating a sensitivity value by calculating a value of a selected peak or peaks of the identified one or more peaks and subtracting a return loss of the selected peak or peaks from a measured signal-to-noise ratio (SNR); (iii) using a differential value between a rotatable section of the one or more internal components or of a rotary joint of the one or more internal components and a stationary or fixed section of the one or more internal components or of a rotary joint of the one or more internal components to determine a change in insertion loss across the one or more internal components or of a rotary joint of the one or more internal components; (iv) obtaining insertion loss rotation variation by rotating a rotatable section of one or more internal components or of a rotary joint of the one or more internal components and by measuring insertion loss at two or more discrete or different angles, or by measuring insertion loss as the rotatable section of the one or more internal components or of a rotary joint of the one or more internal components is continuously rotated; (v) using a peak or peaks corresponding to predetermined or set location or locations of the one or more internal components or of a rotary joint of the one or more internal components and/or the interferometry and/or OCT apparatus/system to determine a health at each corresponding location or locations of the one or more internal components or of a rotary joint of the one or more internal components and/or the interferometry and/or OCT apparatus/system; (vi) calculating a resolution for the identified one or more peaks and/or calculating a sensitivity for the identified one or more peaks, where sensitivity is measured by subtracting a return loss (RL) for a specific peak or peaks from a measured, predetermined or set signal-to-noise ratio (SNR), and where resolution is measured or determined by identifying or obtaining a width of a peak point spread function (PSF) at a specific percent or decibel (dB) reduction from a maximum peak value; (vii) placing a peak reflection at a specific depth or location, within a predetermined deviation range, in the imaging depth range or in the imaging field of view, and calculating the sensitivity, the resolution, or both of the sensitivity and the resolution; (viii) determining a noise floor, or determining a noise floor as the mean of a predetermined or selected A-line of the one or more interferometry signals and/or images, the median of a set of A-lines of the one or more interferoemetry signals and/or images, or the mean or the median of a subset of A-line(s) of the one or more interferometry signals and/or images; (ix) determining a noise floor, or determining a noise floor as the mean of a predetermined or selected A-line of the one or more interferometry signals and/or images, the median of a set of A-lines of the one or more interferometry signals and/or images, or the mean or the median of a subset of A-line(s) of the one or more interferometry signals and/or images, where the subset of the A-line(s) is a set number of samples with a smallest amplitude or a specific number of samples about, or a fixed distance away from, the specific peak or peaks; (x) calculating a resolution for the identified one or more peaks and/or calculating a sensitivity for the identified one or more peaks, where sensitivity is measured by subtracting a return loss (RL) for a specific peak or peaks from a measured, predetermined or set signal-to-noise ratio (SNR), where resolution is measured or determined by identifying or obtaining a width of a peak point spread function (PSF) at a specific percent or decibel (dB) reduction from a maximum peak value, and where the RL value is corrected by an insertion loss (IL) amount up to the specific peak or peaks; and/or (xi) comparing a predetermined or set signal-to-noise ratio (SNR) of a selected peak or peaks of the identified one or more peaks with a measured signal-to-noise ratio (SNR) to see whether the values of the predetermined or set SNR and the measured SNR are the same or similar to indicate an acceptable health of the rotary joint and/or the apparatus/system or to see whether the difference in values of the predetermined or set SNR and the measured SNR exceeds a set amount or threshold to indicate an unacceptable health of the one or more internal components or a rotary joint of the one or more internal components and/or the interferometry and/or OCT apparatus/system.

In one or more embodiments, one or more methods may further include: (i) measuring a current return loss (RL) and comparing the measured current RL to a characterized, determined, or obtained return loss (RL) to determine whether the current RL is the same as, or different from, the characterized, determined, or obtained return loss (RL); and (ii) in a case where the current RL is the same as the characterized, determined, or obtained return loss (RL), then determining that the one or more internal components or a rotary joint of the one or more internal components and/or the interferometry and/or OCT apparatus/system or portion of the interferometry and/or OCT apparatus/system corresponding to the measured return loss is healthy, or, in a case where the current RL is different than the characterized, determined, or obtained return loss (RL), then determining that the health of the one or more internal components or of the rotary joint of the one or more internal components and/or the health of the interferometry and/or OCT apparatus/system or portion of the interferometry and/or OCT apparatus/system corresponding to the measured return loss is in question, and performing additional evaluation to determine whether one or more optics are misaligned or dirty. In one or more embodiments, the characterized, determined or obtained RL may be a value recorded during or after manufacture of the interferometry and/or OCT apparatus or system. One or more methods may further include using a reflection from a predetermined surface of the one or more internal components, of a rotary joint of the one or more internal components, and/or of the interferometry and/or OCT apparatus or system to assess whether an endface of the predetermined surface, of the one or more internal components or of the rotary joint, and/or of a patient interface unit housing the one or more internal components or the rotary joint is dirty by tracking an absolute return loss (absolute RL) signal before and/or after each probe or catheter engagement/disengagement process that is performed for the interferometry and/or OCT apparatus or system, where the absolute RL is defined by the return loss (RL) measured at a peak or peaks taking into account any different insertion losses up to that point in the interferometry and/or OCT apparatus or system.

One or more storage mediums discussed herein may involve or include any feature(s) or combination of features or steps discussed in the present disclosure. For example, a non-transitory computer-readable storage medium may store at least one program for causing a computer to execute a method for determining a health of an interferometry and/or Optical Coherence Tomography (OCT) apparatus or system or one or more internal components of the interferometry and/or OCT apparatus or system. As aforementioned, in one or more embodiments, the interferometry and/or OCT apparatus or system may include an imaging apparatus or system using one or more imaging modalities, and at least one reference reflection that operates so that a reflection from a portion of the one or more internal components of the interferometry and/or OCT apparatus or system is visible in an observable imaging depth or in an imaging field of view. In one or more storage medium embodiments, the method may include: determining the health of the one or more internal components and/or the health of the interferometry and/or OCT apparatus or system based one or more interferometry signals and/or images. In one or more embodiments, one or more of the following may exist or may occur: the interferometry and/or OCT apparatus or system further includes a catheter or probe; and/or the one or more internal components includes one or more of the following: a mating part of the catheter or probe; a portion of the catheter or probe; a rotary joint of a Patient Interface Unit (PIU); a rotary joint of the interferometry and/or OCT apparatus or system; a portion of the PIU; and/or a sacrificial interface in communication with a rotary joint of the interferometry and/or OCT apparatus or system or in communication with the interferometry and/or OCT apparatus or system. In one or more storage medium embodiments, the method may further include: switching the at least one reference reflection from a main reference arm to an auxiliary reference arm; and adjusting the auxiliary reference arm such that one or more reflections from one or more optical surfaces of a rotary joint or of the one or more internal components are disposed or located in the observable imaging depth or in the imaging field of view. In one or more embodiments, the interferometry and/or OCT apparatus or system may further operate to determine the health of the one or more internal components and/or the health of the interferometry and/or OCT apparatus or system, based on the one or more interferometry signals and/or the images, by characterizing or using one or more of the following: one or more return losses, a noise floor, one or more fixed pattern artifacts, and/or point spread functions (PSF) width. In one or more storage medium embodiments, the method may further include: performing peak finding to identify one or more peaks related or relating to one of the following: (i) one or more return signals that return from one or more predetermined locations on the one or more internal components, a rotary joint of the one or more internal components, and/or the interferometry and/or OCT apparatus/system; and/or (ii) the one or more interferometry signals and/or the images; and determining the health of the one or more internal components or the rotary joint of the interferometry and/or OCT apparatus or system using the identified one or more peaks and/or determining the health of the interferometry and/or OCT apparatus/system using the identified one or more peaks. In one or more storage medium embodiments, the method may further include one or more of the following: (i) storing the determined health of the one or more internal components or of a rotary joint of the one or more internal components and/or the determined health of the interferometry and/or OCT apparatus/system in one or more memories; and/or (ii) displaying the determined health of the one or more internal components or of a rotary joint of the one or more internal components and/or the determined health of the interferometry and/or OCT apparatus/system on a display of the interferometry and/or OCT apparatus/system or on a display in communication with the interferometry and/or OCT apparatus/system.

The following paragraphs describe certain explanatory embodiments. Other embodiments may include alternatives, equivalents, and modifications. Additionally, the explanatory embodiments may include several novel features, and a particular feature may not be essential to some embodiments of the devices, systems, and methods that are described herein.

According to other aspects of the present disclosure, one or more additional devices, one or more systems, one or more methods, and one or more storage mediums using, or for use with, OCT and/or other imaging modality technique(s) to perform self-diagnosis, to perform coregistration, and/or to perform imaging using results of the self-diagnosis, etc., are discussed herein. Further features of the present disclosure will in part be understandable and will in part be apparent from the following description and with reference to the attached drawings.

BRIEF DESCRIPTION OF THE DRAWINGS

For the purposes of illustrating various aspects of the disclosure, wherein like numerals indicate like elements, there are shown in the drawings simplified forms that may be employed, it being understood, however, that the disclosure is not limited by or to the precise arrangements and instrumentalities shown. To assist those of ordinary skill in the relevant art in making and using the subject matter hereof, reference is made to the appended drawings and figures, wherein.

DETAILED DESCRIPTION OF THE PRESENT INVENTION

Figure 1:
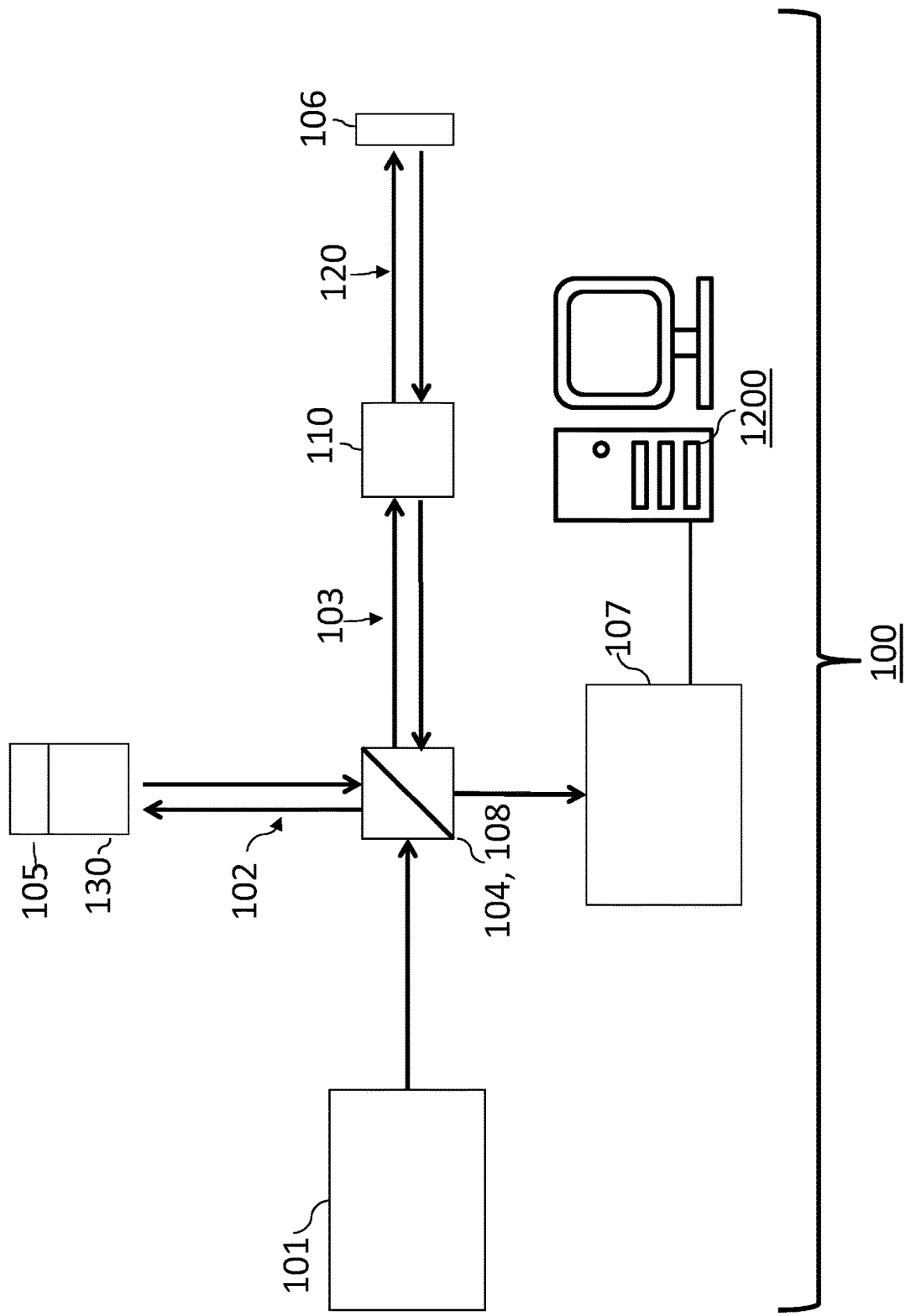
FIG. 1 is a diagram showing an embodiment of a system which can utilize one or more self-diagnosis techniques and/or imaging techniques in accordance with one or more aspects of the present disclosure.

The following description is of certain illustrative embodiments, although other embodiments may include alternatives, equivalents, and modifications. Additionally, the illustrative embodiments may include several novel features, and a particular feature may or may not be used to practice one or more embodiments of the devices, systems, and methods described herein. Embodiments will be described below with reference to the attached drawings.

Like numbers refer to like elements throughout. It shall be noted that the following description is merely illustrative and exemplary in nature, and is in no way intended to limit the disclosure and its applications or uses. The relative arrangement of components and steps, numerical expressions, and numerical values set forth in the embodiments do not limit the scope of the disclosure unless it is otherwise specifically stated. Techniques, methods, and devices which are well known by individuals skilled in the art may not have been discussed in detail since an individual skilled in the art would not need to know these details to enable the embodiments discussed below. Further, endoscopes or other imaging devices discussed herein are not limited to the discussed applications or uses. One or more non-limiting, non-exhaustive embodiments examples of endoscopes or specialized endoscopes may include, but are not limited to, the following: angioscope; anoscope; arthroscope; arterioscope; arthroscope, bronchoscope; capsule endoscope; choledochoscope; colonoscope; colposcope; cystoscope; encephaloscope; esophagogastroduodenoscope; esophagoscope; gastroscope; hysteroscope; laparoscope; laryngoscope; mediastinoscope; nephroscope; neuroendoscope; proctoscope; resectoscope; rhinoscope; sigmoidoscope; sinusoscope; thoracoscope; ureteroscope; uteroscope; borescope; fiberscope; inspection camera; and/or any specialized endoscope or imaging device which may be adapted to include one or more features of the present disclosure. In one or more embodiments, an endoscope may be flexible or rigid. One or more embodiments may also be a probe or an imaging apparatus, such as, but not limited to, the other imaging devices or systems discussed herein.

In medical procedures, improvement or optimization of physiological assessment is preferable to decide a course of treatment for a particular patient. By way of at least one example, physiological assessment is very useful for deciding treatment for cardiovascular disease patients. In a catheterization lab, for example, physiological assessment may be used as a decision-making tool—e.g., whether a patient should undergo a PCI procedure, whether a PCI procedure is successful, etc. While the concept of using physiological assessment is theoretically sound, physiological assessment still waits for more adaption and improvement for use in the clinical setting(s). This situation may be because physiological assessment may involve adding another device and medication to be prepared, and/or because a measurement result may vary between physicians due to technical difficulties. Such approaches add complexities and lack consistency. Therefore, one or more embodiments of the present disclosure may employ computational fluid dynamics based (CFD-based) physiological assessment that may be performed from imaging data to eliminate or minimize technical difficulties, complexities and inconsistencies during the measurement procedure. To obtain accurate physiological assessment, an accurate 3D structure of the vessel may be reconstructed from the imaging data as disclosed in U.S. Provisional Pat. App. No. 62/901,472, filed on Sep. 17, 2019, the disclosure of which is incorporated by reference herein in its entirety.

Visualization, PCI procedure planning, and physiological assessment may be combined to perform complete PCI planning beforehand, and to perform complete assessment after the procedure. Once a 3D structure is constructed or reconstructed and a user specifies an interventional device, e.g., a stent, that is planned to be used, virtual PCI may be performed in a computer simulation (e.g., by one or more of the computers discussed herein, such as, but not limited to, the processor computer 1200, the processor or computer 1200', any other processor discussed herein, etc.). Then, another physiological assessment may be performed based on the result of the virtual PCI. This approach allows a user to find the best device (e.g., interventional device, implant, stent, etc.) for each patient before or during the procedure.

In at least one embodiment of the present disclosure, a method may be used to provide more accurate 3D structure(s) compared to using only one imaging modality. In one or more embodiments, a combination of multiple imaging modalities may be used, catheter connection(s) or disconnection(s) may be detected, rotary joint health (e.g., optical health) and/or apparatus/system health (e.g., optical health) may be determined and evaluated, and coregistration may be processed/performed using one or more techniques discussed herein.

One or more embodiments of the present disclosure may achieve the efficient catheter (or other imaging device) detection, the efficient determination and/or evaluation of rotary joint health and/or apparatus/system health, and/or efficient coregistration result(s) from image(s). In one or more embodiments, the image data may be acquired during intravascular imaging pullback using a catheter (or other imaging device) that may be visualized in an image.

Using one or more of the features or techniques of the present disclosure, one or more embodiments may achieve one or more of the following: (i) get a direct measurement of rotary joint health (or optical health) and/or apparatus/system health (or optical health); (ii) determine rotary joint health without an optical probe or catheter connection which typically is a single-use device; (iii) determine sacrificial interface quality without disconnecting the sacrificial interface and without visual inspection aids; and/or (iv) determine apparatus/system sensitivity as a function of rotary joint rotation angle.

Additionally, one or more embodiments of the present disclosure may achieve at least the following advantages or may include at least the following feature(s): (i) one or more embodiments may achieve the efficient rotary joint health and/or apparatus/system health evaluation and may obtain result(s) without the use of additional equipment; (ii) one or more embodiments may not use trained operators or users (while trained operators or users may be involved, such involvement is not required); (iii) one or more embodiments may perform during a normal course of operation of a catheter and/or an imaging device (as compared with and instead of a separate operation); (iv) one or more embodiments may perform rotary joint health and/or apparatus/system health evaluation using a set of collected images (manually and/or automatically); and (v) one or more embodiments may provide usable measurement(s) with small and/or large samples.

In one or more embodiments of an imaging or medical apparatus/system having one or more processors that operate to evaluate or determine rotary joint health and/or apparatus/system health, the one or more processors may further operate to: (i) acquire or receive the image data during a pullback operation of an intravascular imaging catheter.

In one or more embodiments, the object or sample may include one or more of the following: a vessel, a target specimen or object, and a patient.

One or more devices/apparatuses, optical systems, methods, and storage mediums for performing one or more self-diagnosis or evaluation techniques and/or one or more imaging techniques are disclosed herein. Several embodiments of the present disclosure, which may be carried out by the one or more embodiments of an apparatus, system, method, and/or computer-readable storage medium of the present disclosure are described diagrammatically and visually in at least FIGS. 1 through 13 and other disclosure included herein below.

Turning now to the details of the figures, imaging modalities may be displayed in one or more ways as discussed herein. One or more displays discussed herein may allow a user of the one or more displays to use, control and/or emphasize multiple imaging techniques or modalities, such as, but not limited to, OCT, NIRF, NIRAF, etc., and may allow the user to use, control, and/or emphasize the multiple imaging techniques or modalities synchronously.

In at least one further embodiment example, a method of 3D construction or reconstruction without adding any imaging requirements or conditions may be employed. One or more methods of the present disclosure may use intravascular imaging, e.g., IVUS, OCT, etc., and one (1) view of angiography. In the description below, while intravascular imaging of the present disclosure is not limited to OCT, OCT is used as a representative of intravascular imaging for describing one or more features herein.

In one or more embodiments of the present disclosure, one or more self-diagnosis or evaluation techniques may be used with an OCT or other imaging modality device, system, storage medium, etc. In one or more embodiments, one or more connection or disconnection evaluation techniques may be used for any type of OCT, including, but not limited to, MM-OCT. One or more embodiments of the present disclosure may: (i) determine or calculate rotary joint health and/or apparatus/system health status, and may perform the health status calculation without the use of another piece of equipment; (ii) make evaluations during a normal course of operations (instead of a separate operation) for a catheter (or other imaging device); and (iii) work on small numbers of samples (e.g., as little as one image in an imaging, OCT, and/or MM-OCT application(s)), or may work on large numbers of samples (e.g., a plurality of images or frames, a plurality of samples, a plurality of samples in a plurality of images or frames, etc.), to evaluate rotary joint health and/or apparatus/system health status.

The one or more processors may further operate to perform the coregistration by co-registering an acquired or received angiography image and an obtained one or more Optical Coherence Tomography (OCT) or Intravascular Ultrasound (IVUS) images or frames.

In one or more embodiments, the one or more processors may further operate to one or more of the following: (i) display angiography data along with an image for each of one or more imaging modalities on the display, wherein the one or more imaging modalities include one or more of the following: a tomography image; an Optical Coherence Tomography (OCT) image; a fluorescence image; a near-infrared auto-fluorescence (NIRAF) image; a near-infrared auto-fluorescence (NIRAF) image in a predetermined view, a carpet view, and/or an indicator view; a near-infrared fluorescence (NIRF) image; a near-infrared fluorescence (NIRF) image in a predetermined view, a carpet view, and/or an indicator view; a three-dimensional (3D) rendering; a 3D rendering of a vessel; a 3D rendering of a vessel in a half-pipe view or display; a 3D rendering of the object; a lumen profile; a lumen diameter display; a longitudinal view; computer tomography (CT); Magnetic Resonance Imaging (MRI); Intravascular Ultrasound (IVUS); an X-ray image or view; and an angiography view; and (ii) change or update the displays for the angiography data along with each of the one or more imaging modalities based on the rotary joint health and/or apparatus/system health results and/or an updated location of the catheter (or other imaging device). In one or more embodiments, the one or more imaging modalities may include one or more of the following: Optical Coherence Tomography (OCT); another lumen image(s) modality; an intravascular imaging modality; an imaging modality for fluorescence; a near-infrared auto-fluorescence (NIRAF) imaging modality; a near-infrared auto-fluorescence (NIRAF) imaging modality in a predetermined view, a carpet view, and/or an indicator view; a near-infrared fluorescence (NIRF) imaging modality; a near-infrared fluorescence (NIRF) imaging modality in a predetermined view, a carpet view, and/or an indicator view; a three-dimensional (3D) rendering imaging modality; an imaging modality for a 3D rendering of a vessel; an imaging modality for a 3D rendering of a vessel in a half-pipe view or display; an imaging modality for a 3D rendering of an object, target, or specimen; an imaging modality for a lumen profile; an imaging modality for a lumen diameter display; an imaging modality for a longitudinal view; computer tomography (CT); Magnetic Resonance Imaging (MRI); Intravascular Ultrasound (IVUS); an imaging modality for an X-ray image or view; and an imaging modality for an angiography view.

Just like OCT (or other imaging modality) apparatuses or systems may benefit from evaluating rotary joint health and/or apparatus/system health, SNAKE devices or systems, or other types of robot devices or systems, that may use the same or similar connections may benefit from accurately detecting and/or evaluating rotary joint health and/or apparatus/system health. The OCT application(s) may have mechanisms for saving data, and the SNAKE or robot application(s) may also use saving data mechanisms in one or more embodiments. Additionally, the SNAKE robot or other robot camera(s) may be or may include a color camera, and the OCT images collected by the OCT application(s) may be greyscale or may include greyscale images, so a shift from color to grayscale may also be employed for imaging application(s) and for considering imaging quality and related data in one or more embodiments.

Turning now to the details of the figures, FIG. 1 shows an OCT system too (as referred to herein as "system too" or "the system too") which operates to utilize an imaging modality (such as, but not limited to, angiography, Optical Coherence Tomography (OCT), Multi-modality OCT (MM-OCT), near-infrared auto-fluorescence (NIRAF), near-infrared fluorescence (NIRF), OCT-NIRAF, OCT-NIRF, etc.) technique, including, but not limited to, one or more embodiments of self-diagnosis techniques and/or one or more imaging techniques discussed herein, with optical probe applications in accordance with one or more aspects of the present disclosure. The system too comprises a light source 101, a reference arm 102, a sample arm 103, a splitter 104 (also referred to herein as a "beam splitter"), a reference mirror (also referred to herein as a "reference reflection") 105, and one or more detectors 107. The system too may include a phase shift device or unit 130, and, in one or more embodiments, the phase shift device or unit may be omitted. In one or more embodiments, the system too may include a patient interface device or unit ("PIU") 110 and a catheter or probe 120 (as diagrammatically shown in FIGS. 1-2), and the system too may interact with a sample or target 106 (e.g., via the catheter/probe 120 and/or the PIU 110). In one or more embodiments, the system too includes an interferometer, or an interferometer is defined by one or more components of the system too, such as, but not limited to, at least the light source 101, the reference arm 102, the sample arm 103, the splitter 104, and the reference mirror 105.

The light source 101 operates to produce a light to the splitter 104, which splits the light from the light source 101 into a reference beam passing into the reference arm 102 and a sample beam passing into the sample arm 103. The beam splitter 104 is positioned or disposed at an angle to the reference mirror 105, the one or more detectors 107, and the sample, object, or target 106. The reference beam goes through the phase shift unit 130 (when included in a system, as shown in the system 100), and the reference beam is reflected from the reference mirror 105 in the reference arm 102 while the sample beam is reflected or scattered from a sample, object, or target 106 through the PIU (patient interface unit; also referred to herein as a patient interface component (PIC)) 110 and the catheter 120 in the sample arm 103. In one or more embodiments, the phase shift unit 130 may be omitted from a device or system as desired. Both of the reference and sample beams combine (or recombine) at the splitter 104 and generate interference patterns. The output of the system 100 and/or the interferometer thereof is continuously acquired with the one or more detectors 107, e.g., such as, but not limited to, photodiodes, cameras, multi-array cameras, etc. The one or more detectors 107 measure the interference or interference patterns between the two radiation or light beams that are combined or recombined. In one or more embodiments, the reference and sample beams have traveled different optical path lengths such that a fringe effect is created and is measurable by the one or more detectors 107. Electrical analog signals obtained from the output of the system 100 and/or the interferometer thereof are converted to digital signals to be analyzed with a computer, such as, but not limited to, the computer 1200, 1200' (shown in FIG. 12 or FIG. 13, respectively, discussed further below). In one or more embodiments, the light source 101 may be a radiation source or a broadband light source that radiates in a broad band of wavelengths. In one or more embodiments, a Fourier analyzer including software and electronics may be used to convert the electrical analog signals into an optical spectrum.

The light source 101 may include a plurality of light sources or may be a single light source. The light source 101 generates broadband laser lights in one or more embodiments. The light source 101 may include any light emitting component, such as, but not limited to, one or more of a laser, an organic Light-Emitting Diode (OLED), a Light-Emitting Diode (LED), a halogen lamp, an incandescent lamp, supercontinuum light source pumped by a laser, and/or a fluorescent lamp. The light source 101 may be any light source that provides light which may then be split up into at least three bands in which each band is further dispersed to provide light which is then used to for spectral encoding of spatial information. The light source 101 may be any light source that provides light which may then be dispersed to provide light which is then used for imaging, performing control, viewing, changing, emphasizing methods for imaging modalities, constructing or reconstructing 3D structure(s), and/or any other method discussed herein. The light source 101 may be fiber coupled or may be free space coupled to the other components of the system or systems discussed herein, such as, but not limited to, the system 100, the system 100', the system 100'', the system 100''', etc. The light source 101 may be a swept-source (SS) light source.

In accordance with at least one aspect of the present disclosure, a feature of OCT devices or systems is implemented using fiber optics. As aforementioned, one application of an OCT technique of the present disclosure is to use OCT with a catheter or probe 120 as schematically shown in FIGS. 1-2.

Figure 2:
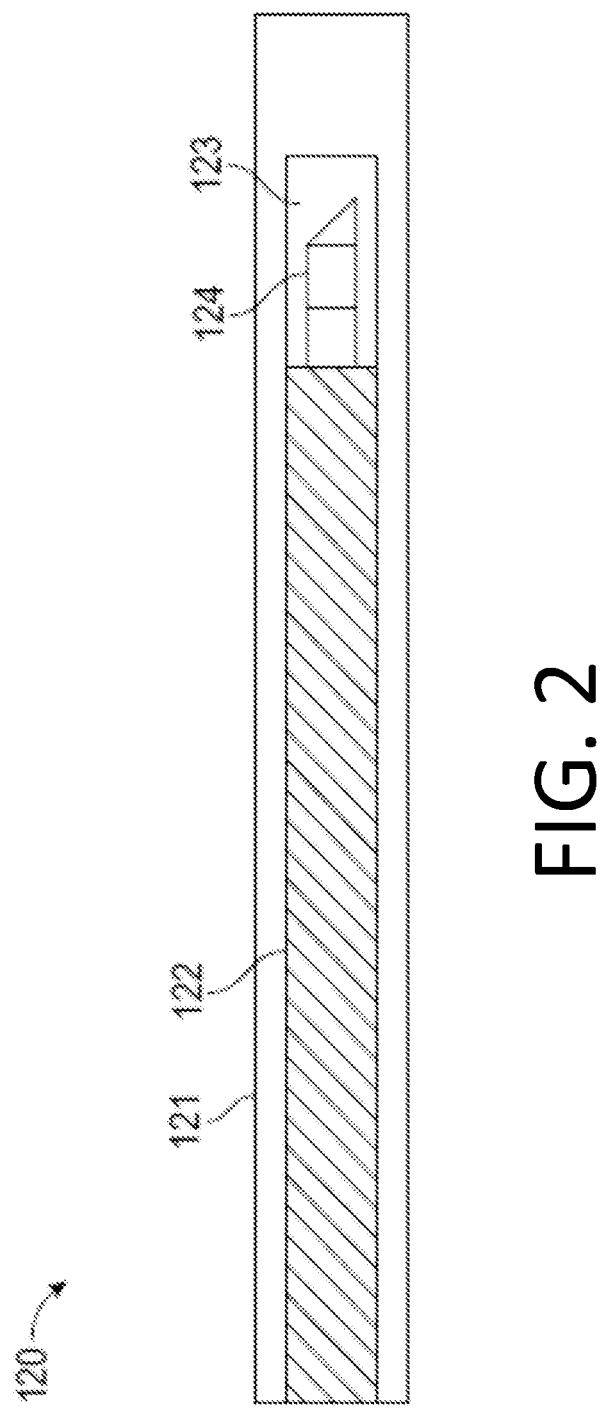
FIG. 2 is a diagram of an embodiment of a catheter that may be used with at least one embodiment of an apparatus or system for performing self-diagnosis techniques and/or imaging techniques in accordance with one or more aspects of the present disclosure.

FIG. 2 shows an embodiment of the catheter or probe 120 including a sheath 121, a coil 122, a protector 123, and an optical probe 124. As shown schematically in FIGS. 1-2, the catheter 120 preferably is connected to the PIU 110 to spin the coil 122 with pullback (e.g., at least one embodiment of the PIU 110 operates to spin the coil 122 with pullback). The coil 122 delivers torque from a proximal end to a distal end thereof (e.g., via or by a rotational motor in the PIU 110). In one or more embodiments, the coil 122 is fixed with/to the optical probe 124 so that a distal tip of the optical probe 124 also spins to see an omnidirectional view of a biological organ, sample, target, or material being evaluated, such as, but not limited to, hollow organs, such as, but not limited to, vessels, a heart, a lung or lungs, etc. For example, fiber optic catheters and endoscopes may reside in the sample arm (such as the sample arm 103 as shown in FIG. 1) of an OCT interferometer in order to provide access to internal organs (which may be displayed using one or more imaging modalities such as, but not limited to, intravascular images), gastro-intestinal tract, or any other narrow area, that are difficult to access. As the beam of light through the optical probe 124 inside of the catheter 120 or endoscope is rotated across the surface of interest, cross-sectional images of one or more targets, objects, or samples are obtained. In order to acquire three-dimensional data, the optical probe 124 is simultaneously translated longitudinally during the rotational spin resulting in a helical scanning pattern. This translation may be performed by pulling the tip of the probe 124 back towards the proximal end and therefore referred to as a pullback.

In one or more embodiments, the patient user interface 110 may comprise or include a connection component (or interface module), such as a rotary junction, to connect one or more components, such as one or more components of a probe (e.g., a catheter 120 (see e.g., FIGS. 1-2)), a needle, a capsule, a patient interface unit or component (e.g., the patient interface unit or component 110), etc., to one or more other components, such as, an optical component, a light source (e.g., the light source 101), a deflection section (e.g., such as a deflection or deflected section, which is a component that operates to deflect the light from the light source to the interference optical system (e.g., to the reference arm 102 and/or the sample arm 103), and then send light received from the interference optical system towards the at least one detector; a deflection or deflected section that includes at least one of: one or more interferometers, a circulator, a beam splitter, an isolator, a coupler, a fusion fiber coupler, a partially severed mirror with holes therein, and a partially severed mirror with a tap; a splitter 104; a deflection or deflected section 108; etc.), the sample arm 102, a motor that operates to power the connection component and/or the patient user interface or patient interface unit 110, etc. For example, when the connection member or interface module is a rotary junction, preferably the rotary junction operates as discussed below). In one or more other embodiments, the rotary junction may be at least one of: a contact rotary junction, a lenseless rotary junction, a lens-based rotary junction, or other rotary junction known to those skilled in the art. In one or more embodiments, the interferometer or the optical interference system may include one or more components of the system 100 (or any other system discussed herein) such as, but not limited to, one or more of the light source 101, the deflected section 108, the rotary junction RJ, a PIU 110, a catheter 120, etc. One or more features of the configurations of any of at least FIGS. 1-10 and 12-13 (and/or any other configurations discussed herein)

may be incorporated into one or more of the systems, including, but not limited to, the system 100, 100', 100", 100'", etc. discussed herein.

In at least one embodiment, the PIU 110 may include a Fiber Optic Rotary Junction (FORJ), a rotational motor and translation motorized stage (e.g., a portion of the PIU 110), and a catheter connector (e.g., a portion of the PIU 110). The FORJ allows uninterrupted transmission of an optical signal while rotating a fiber along the fiber axis. The FORJ may have a free space optical beam combiner including a rotor and stator.

Descriptions of like-numbered elements present in the system 100' and already described above, such as for the system 100, shall not be repeated, and are incorporated by reference herein in their entireties.

In at least one embodiment, the console 1200, 1200' operates to control motions of a motor and translation motorized stage (hereinafter referred to as "motor" or "motor and stage"), acquires intensity data from the at least one detector(s) 107, and displays the scanned image (e.g., on a monitor or screen such as a display, screen or monitor 1209 as shown in the console 1200 of FIG. 12 and/or the console 1200' of FIG. 13 as further discussed below). In one or more embodiments, the console 1200, 1200' operates to change a speed of the motor and/or to stop the motor. In at least one embodiment, a console or computer 1200, 1200', any other computer or processor discussed herein, etc. further operates to control motions of the RJ via the motion control unit (MCU) 112 or a motor M. In one or more embodiments, the MCU 112 or the motor M operates to change a speed of a motor of the RJ and/or of the RJ. The motor may be a stepping or a DC servo motor to control the speed and increase position accuracy (e.g., compared to when not using a motor, compared to when not using an automated or controlled speed and/or position change device, compared to a manual control, etc.).

In one or more embodiments, the console or computer 1200, 1200' operates to control the system 100 (and other systems, such as, but not limited to, the system 100', the system 100", the system 100'", etc. as discussed further below), the catheter 120 and/or one or more other above-described components of the system 100 (or any component or components of the other system or systems discussed herein). In at least one embodiment, the console or computer 1200, 1200' operates to acquire intensity data from the one or more detectors 107 of the OCT system/device/apparatus, and displays the image(s) (e.g., on a monitor or screen such as, but not limited to, a display, screen, or monitor 1209 as shown in the console 1200 of FIG. 12 and/or the console 1200' of FIG. 13 as further discussed below). The output of the one or more components of the system 100 (and other systems, such as, but not limited to, the system 100', the system 100", the system 100'", etc. as discussed further below) is acquired with the one or more detectors 107 of the OCT system/device/apparatus, e.g., such as, but not limited to, photodiodes, Photomultiplier tube(s) (PMTs), line scan camera(s), or multi-array camera(s). Electrical analog signals obtained from the output of the system 100 (and/or other systems, such as, but not limited to, the system 100', the system 100", the system 100'", etc. as discussed further below) or one or more components thereof are converted to digital signals to be analyzed with a computer, such as, but not limited to, the computer 1200, 1200' (e.g., as shown in FIGS. 1, 3A-3G, 8-10, and 12-13). In one or more embodiments, the light source 101 may be a radiation source or a broadband light source that radiates in a broad band of wavelengths. In one or more embodiments, a Fourier analyzer including software and electronics may be used to convert the electrical analog signals into an optical spectrum. In some embodiments, the one or more detectors 107 comprise three detectors configured to detect three different bands of light. The output of an interferometer (e.g., an OCT interferometer, an interferometer of another imaging modality, etc.) may be detected with a first detector(s) 107, wherein the first detector(s) 107 may be photodiodes or multi-array cameras (or other type of detector discussed herein or known to those skilled in the art), and then may be recorded to a computer (e.g., to the computer 1200 as shown in FIGS. 1, 3A-3G, 8-10, and 12, the computer 1200' as shown in FIG. 13, or any other computer discussed herein).

Additionally or alternatively, the one or more detectors 107 may be a linear array, a charge-coupled device (CCD), a plurality of photodiodes or some other method of converting the light into an electrical signal. The one or more detectors 107 may transmit the digital or analog signals to a processor or a computer such as, but not limited to, an image processor, a processor or computer 1200, 1200' (see e.g., FIGS. 1, 3A-3G, 8-10, and 12-13), any other processor or computer discussed herein, a combination thereof, etc. The image processor may be a dedicated image processor or a general purpose processor that is configured to process images. In at least one embodiment, the computer 1200, 1200', or any other processor or computer discussed herein may be used in place of, or in addition to, the image processor. In an alternative embodiment, the image processor may include an ADC and receive analog signals from the one or more detectors 107. The detector(s) 107 may include an analog to digital converter (ADC) in one or more embodiments. The image processor may include one or more of a CPU, DSP, FPGA, ASIC, or some other processing circuitry. The image processor may include memory for storing image, data, and instructions. The image processor may generate one or more images based on the information provided by the one or more detectors 107. A computer or processor discussed herein, such as, but not limited to, a processor of the devices, apparatuses or systems of FIGS. 1-10, the computer 1200, the computer 1200', the image processor, may also include one or more components further discussed herein (see e.g., FIGS. 12-13).

In one or more embodiments, one or more imaging techniques may be used, such as, but not limited to, various OCT imaging techniques, lumen edge detection, stent strut detection, and/or artifact detection techniques, and other techniques as discussed in at least U.S. Pat. App. No. 62/901,472, which is incorporated by reference herein in its entirety, and as discussed in U.S. patent application Ser. No. 16/990,800, filed on Aug. 11, 2020, which is incorporated by reference herein in its entirety. In one or more embodiments of the present disclosure, an OCT image is formed in a polar coordinate system from A-lines. Each A-line includes much information about the imaged object, such as, but not limited to: clear indications of artifacts from metal objects (e.g., stents, stent struts, guide wires, PIU reflection, catheter/probe reflection, noise artifacts, etc.) like narrow signal width and/or sharp rising and falling edges; significant difference in signal intensity and shape for unobstructed soft tissue compared to the sheath reflection and other artifacts like wide signal width and a gentle falling edge. Each A-line may represent a cross-sectional 1D sampling of a target, sample, object, etc., such as, but not limited to, a vessel, along a certain view angle. As an imaging probe or device rotates (e.g., rotates about 0 to about 360 degrees, about 180 degrees to about 360 degrees, about 360 degrees, etc.), the corresponding A-lines form the complete two-dimensional (2D) cross-section of the target, sample, object, etc. (e.g., the vessel) in polar coordinates, which is then converted into Cartesian coordinates to form the tomographical-view (tomo-view) image of the cross-section of the target, sample, object, etc. (e.g., the vessel).

In accordance with at least one aspect of the present disclosure and as aforementioned, one or more additional methods for lumen, stent, and/or artifacts detection of OCT images may be used with one or more embodiments of device(s), system(s), method(s), and/or storage medium(s) discussed herein, including, but not limited to, technique(s) as discussed in U.S. patent application Ser. No. 16/414,222, filed on May 16, 2019, the entire disclosure of which is incorporated by reference herein in its entirety, and in U.S. Pat. Pub. No. 2019/0374109, which was published on Dec. 12, 2019, the disclosure of which is incorporated by reference herein in its entirety.

Regardless of the approach, a predetermined or determined threshold may be used to detect the most significant pulse that may be corresponding to the lumen edge (in one or more embodiments, the most significant pulse denotes the maximum peak and its associated front edge also named as "major peak/edge"; such data may contain or include artifact edge pixels) in a specific A-line in one or more embodiments. Any pulse above the threshold is an edge pulse of an object candidate. The largest pulse among all the candidates in terms of area under the pulse is considered to be the maximum peak (also referred to herein as the "most significant pulse", or the "major peak/edge", etc.).

One or more embodiments of the present disclosure may be used with one or more devices, systems, methods, and/or storage mediums for performing engagement and/or disengagement status determination and/or engagement and/or disengagement guidance techniques, such as, but not limited to, as discussed in U.S. Pat. Pub. No. 2022/0042783 A1, published on Feb. 10, 2022, the disclosure of which is incorporated by reference herein in its entirety.

One or more embodiments of the present disclosure may minimize, reduce, and/or avoid rotary joint and/or device/system failures and may have a robust means of determining status of a rotary joint and/or a device/system (e.g., an imaging device or apparatus, an imaging system, a medical device or apparatus, a medical system, etc.). Knowledge of rotary joint and/or device/system status may be used to communicate status to a user and to allow specific apparatus and/or system functionality and/or to inhibit other apparatus and/or system functionality.

One or more embodiments may obtain a direct analysis of self-diagnosis techniques, and that use the results to determine rotary joint health and device/system health, using at least one reliable optical interference signal. One or more embodiments may operate with or without prior knowledge of reflection strength(s) from probe/catheter distal reflections, and preferably do not require such knowledge of the reflection strength(s).

One or more embodiments of the present disclosure may use an OCT signal at a patient interface unit (PIU) output connector to determine rotary joint and/or system/device status, and/or may use an OCT signal about or for the PIU output connector and a catheter connector to perform one or more of the self-diagnosis techniques discussed herein (also referred to herein as an "self-diagnosis process" or "self-diagnosis processes").

One or more features of the present disclosure may be employed or exercised using any OCT apparatus and/or system, and may be done so using only minor modifications to the reference arm where an apparatus and/or system uses a single reference arm path, one or more embodiments of a method or technique of the present disclosure may use two reference arm paths or the ability to sufficiently adjust reference arm delay so as to adjust the imaging FOV to be at either the main sample imaging location or at about the system distal-most point (e.g., a location where the catheter/probe mates with the sample arm, the rotary joint of the PIU, or a location of a sacrificial interface, etc.).

One or more embodiments of a system for increasing imaging depth range may include: an OCT system; a reference reflection adjusted so that a reflection from a system mating connector is visible in an imaging field of view; and one or more processors that operate to determine if a catheter/probe is mated to the system mating connector.

Now turning to the details of FIGS. 3A-3G, diagrams of respective apparatus/system embodiments are shown for performing one or more self-diagnosis techniques and/or one or more imaging techniques in accordance with one or more aspects of the present disclosure.

FIGS. 3A-3G depict several different embodiments of OCT interferometer apparatuses/systems with retro-reflection paths for main OCT imaging and for auxiliary OCT imaging in accordance with one or more aspects of the present disclosure. As shown via the reference numbers in FIGS. 3A-3G, while not limited to such examples, one or more of the subject apparatuses or systems may have the same or similar components (or one or more of the same or similar components) as other apparatuses or systems discussed herein. For example, one or more apparatuses may have a light source 101, a splitter 104 or deflecting/deflection section 108, one or more circulators 901, a reference arm 102, a sample arm 103, a PIU 110, a catheter or probe 120, a reference reflector 105, one or more detectors (e.g., one or more photo-receivers, one or more photo diodes, etc.) 107, a computer, processor or other type of data acquisition unit (DAQ) (e.g., computer or processor 1200, computer or processor 1200', etc.), etc. Numerous non-limiting, non-exhaustive embodiment examples of such components are discussed throughout the disclosure with reference to at least FIGS. 1, 8-10, and 12-13, and detail(s) of one or more embodiments of one or more of such components will not be repeated with reference to FIGS. 3A-3G. The discussions of FIGS. 3A-3G, as shown below, include details on structural modification(s), difference(s), or other variation(s) that may be used for one or more self-diagnosis techniques and/or one or more imaging techniques discussed herein.

Figure 3A:
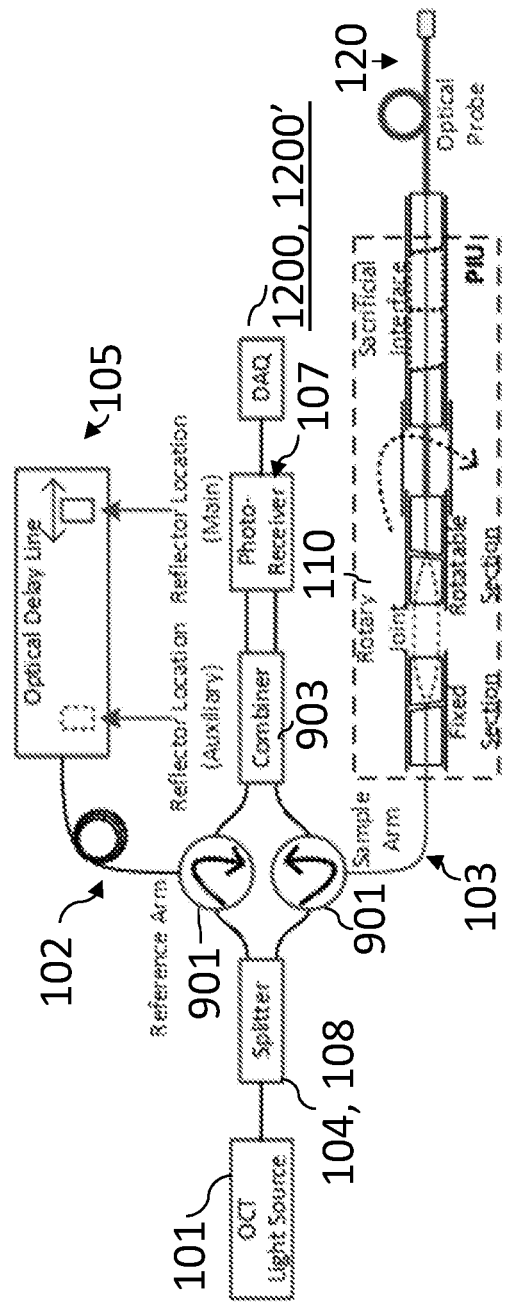
FIGS. 3A-3G are diagrams of respective apparatus/system embodiments for performing self-diagnosis techniques and/or imaging techniques in accordance with one or more aspects of the present disclosure.

FIG. 3A depicts a reference arm 102 that makes use of an optical delay line (e.g., a long optical delay line). The optical delay line has sufficient adjustment to cover at least the length of the probe or catheter 120. When the delay is increased in one or more embodiments, the reference path or arm 102 may match the length of the sample path or arm 103 with the probe or catheter 120 included and may permit regular OCT system imaging. In one or more embodiments, when the delay is decreased, the reference path or arm 102 may match the length of the sample path or arm 103 without the probe or catheter 120 and may permit OCT imaging of one or more of the following: the rotary joint region, the device or system to a catheter connection region, or another predetermined region of the device or system. In one or more embodiments, a rotary joint region may include a sacrificial interface. However, in one or more other embodiments, a rotary joint region may not include a sacrificial interface.

Figure 3B:
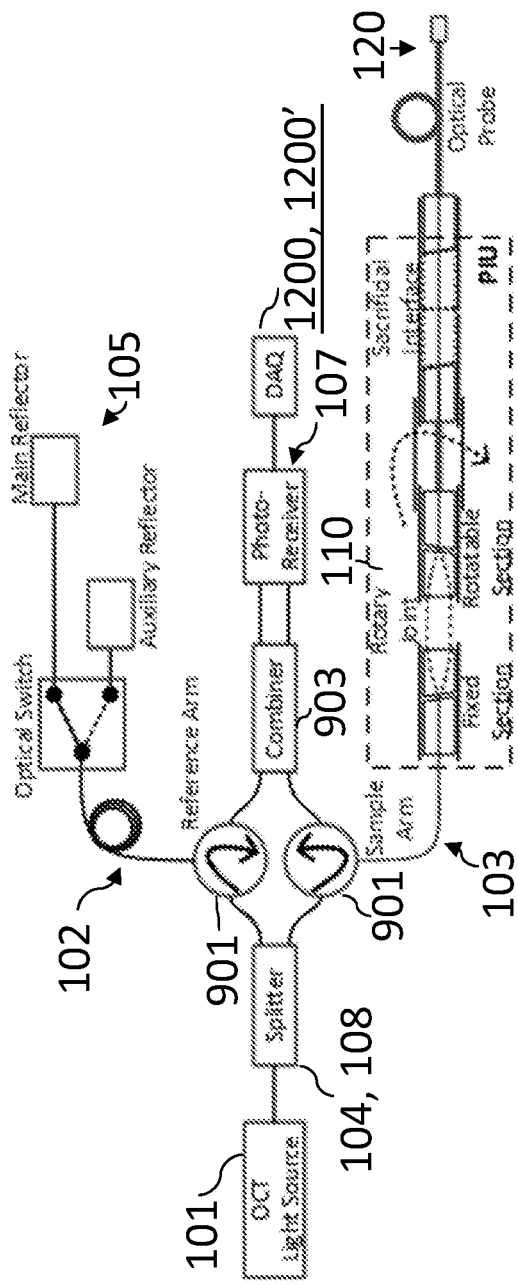

FIG. 3B depicts an optical power-efficient reference arm 102 that makes use of a 1×2 optical switch. The optical switch main output port is part of the main reference path or arm 102 and the secondary port constitutes, or is, part of the auxiliary reference path or arm (see split in the reference arm 102 of FIG. 3B). In one or more embodiments, the main reference path or arm 102 may match the length of the sample path or arm 103 with the probe or catheter 120 included and may permit regular OCT system imaging. In one or more embodiments, the auxiliary reference path may match the length of the sample path or arm 103 without the probe or catheter 120 and may permit OCT imaging of one or more of the following: the rotary joint region, the device or system to a catheter connection region, or another predetermined region of the device or system.

Figure 3C:
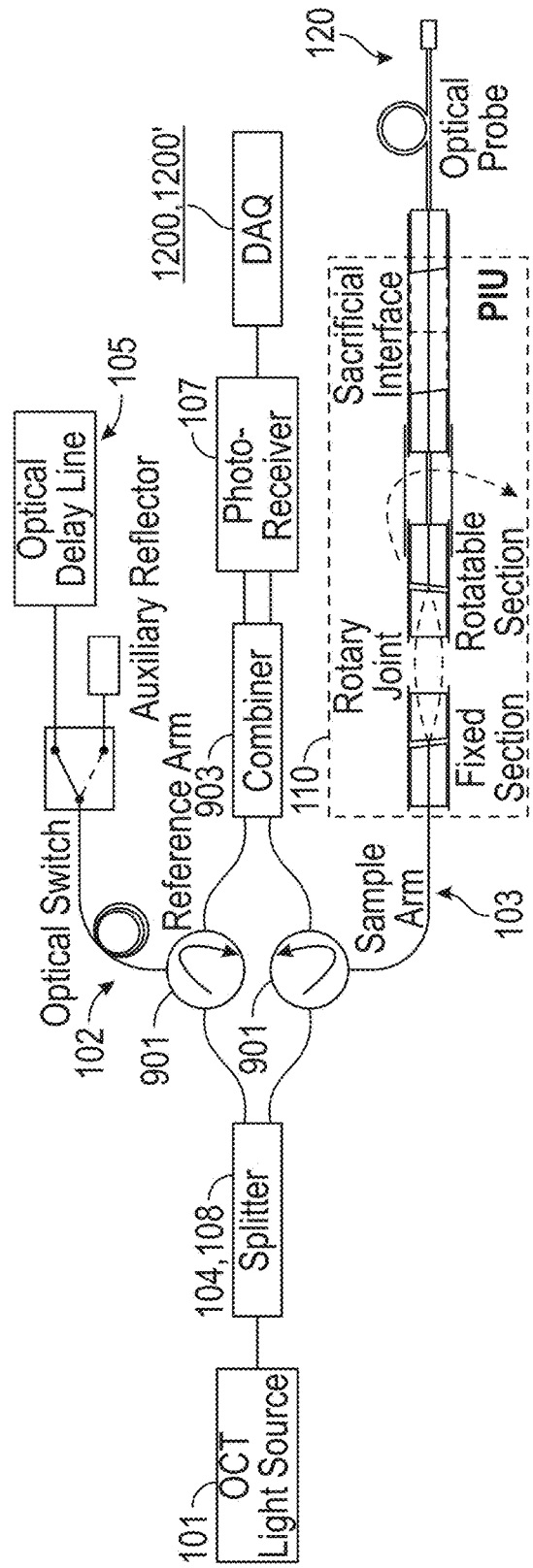

FIG. 3C depicts a similar apparatus/system to the one from FIG. 3B, where the main reflector is replaced with an optical delay line. The optical delay line allows adjustment of the main reference arm 102 to account for catheters/probes (e.g., the catheter or probe 120) with varying optical lengths. A similar configuration may be used where a second optical delay line is used to allow adjustment of the auxiliary reference arm to account for adjustment to focus imaging field of view on specific reflections from the rotary joint.

Figure 3D:
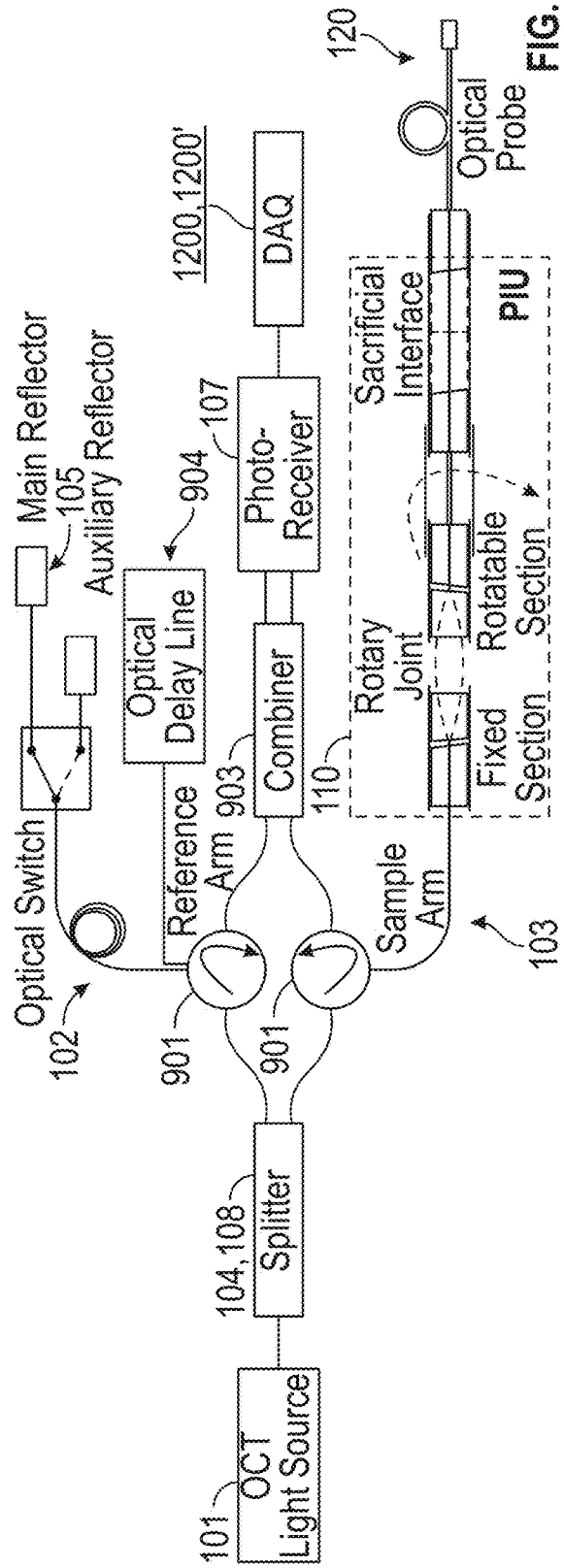

FIG. 3D depicts a similar system to the one from FIG. 3B, where the reference arm makes use of a 4-port circulator (see e.g., the top circulator 901 in the embodiment of FIG. 3D) instead of a 3-port circulator. The extra port allows for the use of an optical delay line. The optical delay line allows in this case for adjustment of both the main and the auxiliary reference arms to account for catheters/probes (e.g., the catheter or probe 120 in FIG. 3D) with varying optical lengths and to address manufacturing tolerances of the system/apparatus interferometer including replacement of PIUs (e.g., PIU 110 of FIG. 3D) with different lengths (e.g., different lengths may stem from one or more loose tolerances in one or more embodiments).

Figure 3E:
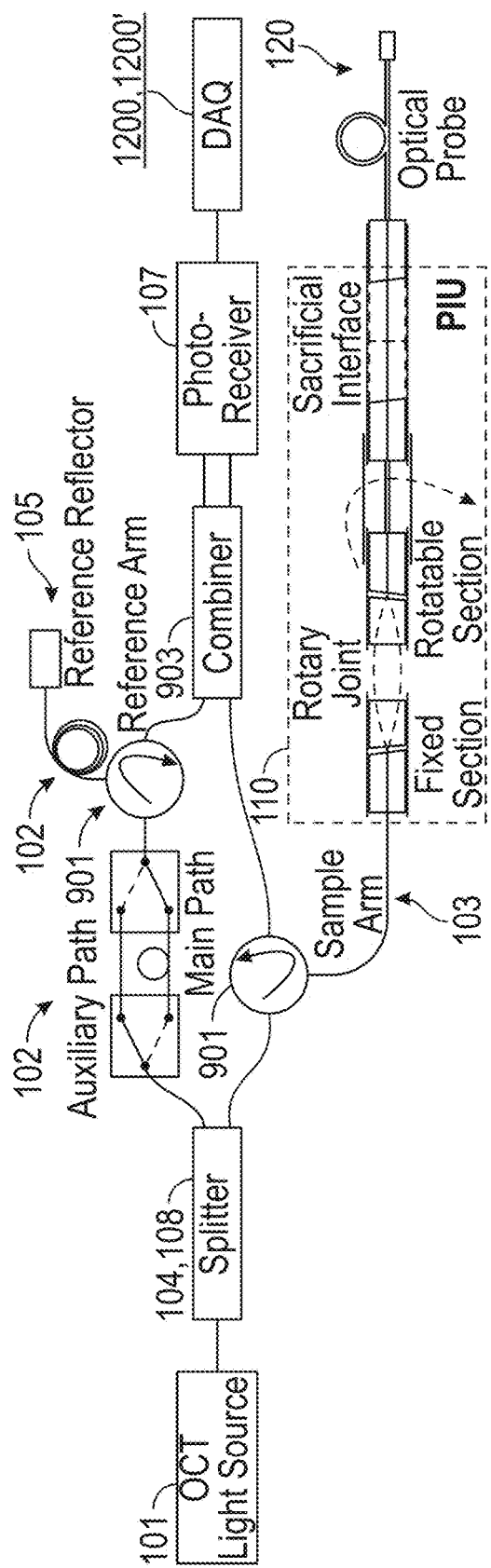

FIG. 3E depicts a similar apparatus/system to the one from FIG. 3B, where the main and auxiliary reference arms of the reference arm 102 are delineated by the use of two 1×2 optical switches in series. The reference reflector (e.g., the reference reflector 105) in this case may be a fixed reflector or an optical delay line.

Figure 3F:
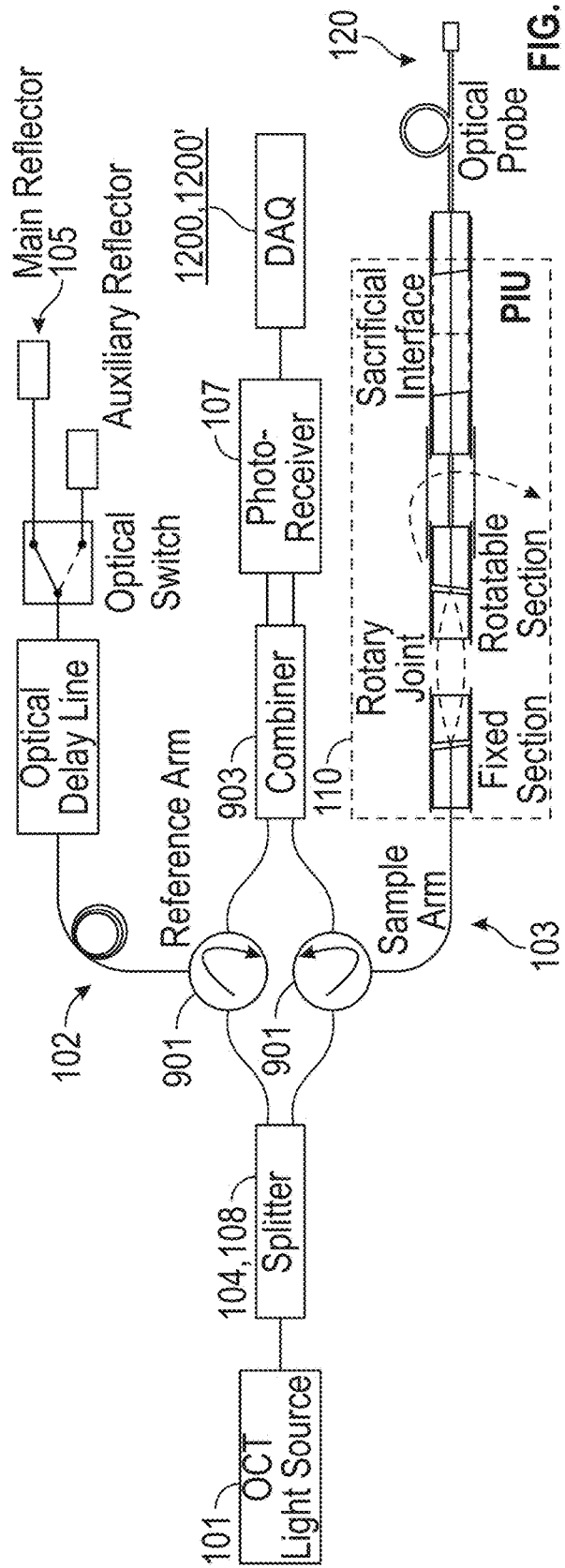

FIG. 3F depicts a similar apparatus/system to the one from FIG. 3B, where the optical delay line is inserted in the reference arm 102 before the optical switch. The optical delay line allows, in this embodiment, for adjustment of both the main and the auxiliary reference arms of the reference arm 102 to account for catheters/probes (e.g., the catheter or probe 120) with varying optical lengths and to address manufacturing tolerances of the apparatus/system interferometer including replacement of PIUs (e.g., the PIU 110) with different lengths (e.g., for main imaging, for auxiliary imaging, for main imaging and auxiliary imaging, etc.).

Figure 3G:
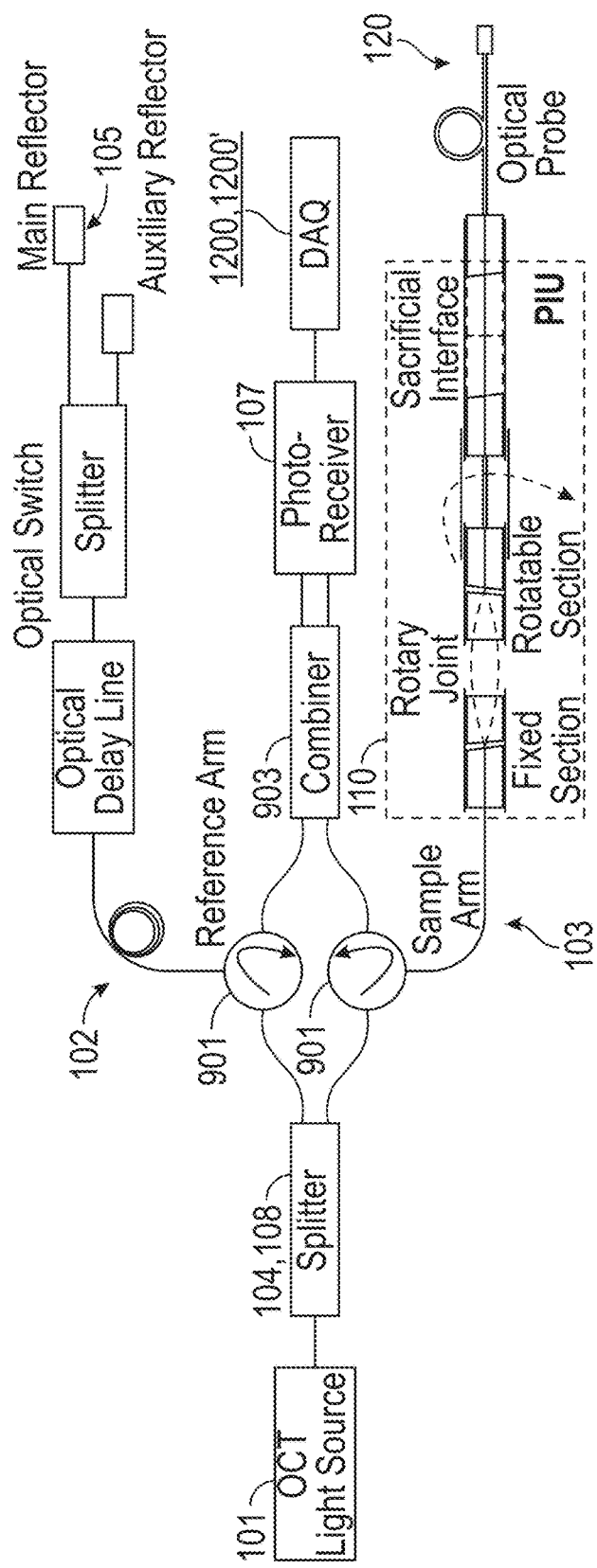

FIG. 3G depicts a similar apparatus/system to the one from FIG. 3B, where the optical delay line is used to adjust the optical length to match either the main reflector or the auxiliary reflector of the reference reflection 105. In at least one embodiment, light may be reflected from both reflectors of the reference reflection 105 at the same time so light efficiency may be reduced. Alternatively or additionally, an initial splitter may be selected to guarantee or provide that an adequate light level (e.g., of a predetermined amount, of a set amount, of a user-defined amount, of an application-specific amount, etc.) is reflected back from the reference arm 102. In one or more embodiments, a splitter located after the optical delay line as shown in FIG. 3G may be a 50/50 split ratio, but is not limited to such a split ratio. Preferably, in one or more embodiments, separation of the optical delay line is such that only one of the two imaging modes may be captured at a time by taking advantage of a limited coherence length of a laser or light source (e.g., the light source 101). Lasers or light sources with a coherence length not smaller, or not substantially smaller, than the optical delay line separation for two imaging modes may lead to an overlap of the rotary joint reflection with the main object, target, or sample during normal OCT imaging.

Figure 4:
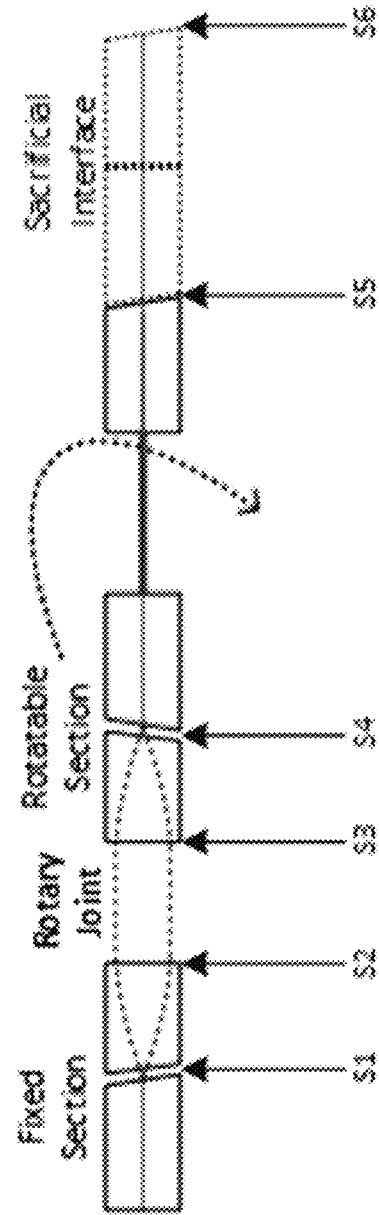
FIG. 4 is a diagram of at least one embodiment of a patient interface unit (PIU), and/or at least one embodiment of a rotary joint, that may be used with a sacrificial interface in accordance with one or more aspects of the present disclosure.

FIG. 4 depicts optical components of at least one embodiment of a rotary joint with a sacrificial interface that may be used. S1 represents a stationary ferrule-to-lens interface surface. S2 represents a stationary lens-to-air interface surface. S3 represents an air-to-rotatable lens interface surface. S4 represents a rotatable lens-to-ferrule interface surface. S5 represents a rotatable ferrule-to-sacrificial interface surface. S6 represents a rotatable sacrificial interface-to-air surface.

Figure 5:
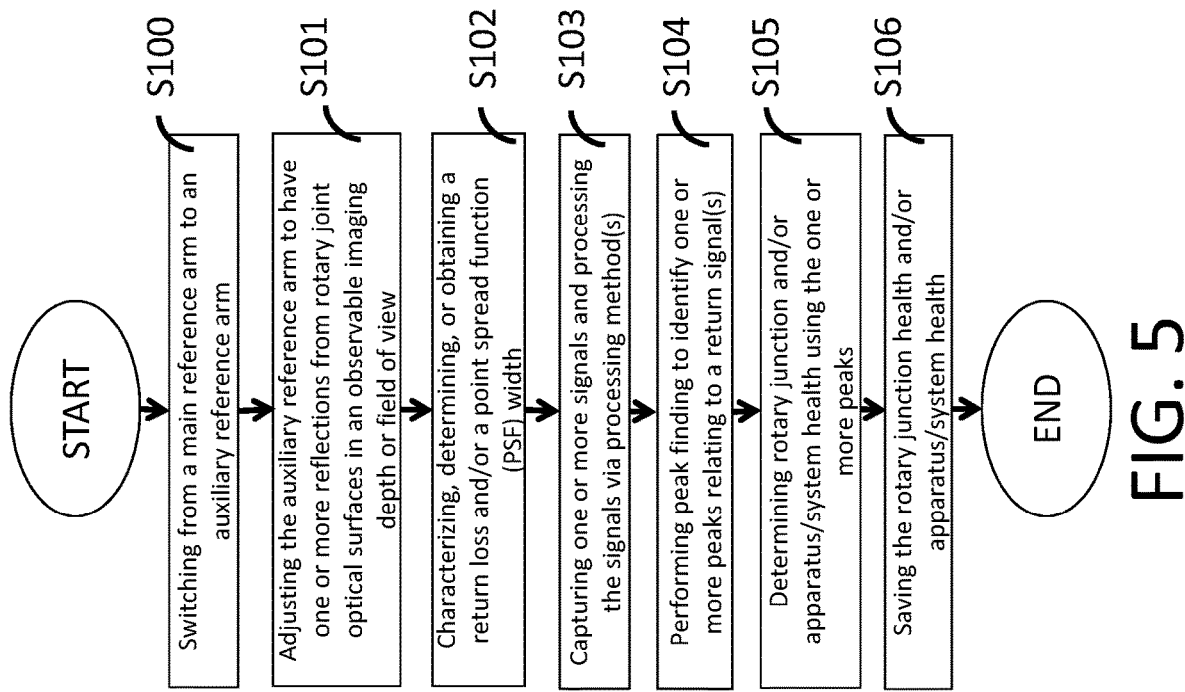
FIG. 5 is a flowchart of at least one embodiment of a method for performing self-diagnosis technique(s) or process(es) that may be used in accordance with one or more aspects of the present disclosure.

In one or more embodiments of the present disclosure, one or more steps may be used to determine rotary joint health status and/or apparatus/system health status where, at a start of the method or process, the apparatus or system may switch to an auxiliary reference arm path (see e.g., step S100 as shown in FIG. 5). The apparatus or system may adjust the auxiliary reference arm (as necessary or as desired) to have one or more reflections from rotary joint surfaces (or rotary joint optical surfaces) in an observable imaging depth or field of view (see e.g., step S101 of FIG. 5). The auxiliary reference arm may be adjusted to obtain one or more reflections at a same time or to obtain each reflection of the one or more reflections one at a time (e.g., at different times, in a row, serially or successively, etc.).

While not limited thereto, in one or more embodiments, a return loss and/or a point spread function (PSF) width from the surfaces of the rotary joint may be characterized, determined, or obtained (see e.g., step S102 of FIG. 5) (e.g., during apparatus or system build, during testing (e.g., after the build), etc.) and may be stored, for example, in the apparatus or system (e.g., a priori, after testing the apparatus or system during or after the build, etc.) or in another storage device or system location. Reflections from a sacrificial interface may or may not characterized or determined beforehand. By way of at least one embodiment example, the values (e.g., of the return loss, of the PSF width, of the reflections, or any other values being stored for use of the apparatus or system, etc.) may be stored in a memory (e.g., a non-volatile memory or any other type of memory discussed herein) in the apparatus or system (e.g., in the patient interface unit PIU 110, or in any other component or location of the apparatus or system, etc.). In another example, the values may be stored in a solid state drive (SSD), in a storage drive (e.g., such as, but not limited to, a hard drive (HD), a hybrid hard drive (HHD), a solid state hybrid drive (SSHD), etc.), any other storage device discussed herein, or any other type of storage device known to those skilled in the art. In one or more embodiments, step S102 may be omitted.

In one or more embodiments, the apparatus or system (or a processor thereof), or method being performed, may capture one or more signals (e.g., one or more interferometric signals, one or more A-lines, etc.) and may process the one or more signals (e.g., one or more interferometric signals, one or more A-lines, etc.) using one or more processing methods (e.g., one or more OCT processing methods (see e.g., step S103 in FIG. 5). In one or more embodiments, the processed signals may be one or more A-lines. While not limited thereto, the one or more processing methods may include (or may exclude) one or more of the following: background subtraction; and/or zero-padding before the FFT or interpolating after the FFT to increase two (2)-point resolution during PSF width calculation, determination, or obtaining.

In one or more embodiments, the apparatus or system, or method being performed, may perform peak finding to identify one or more peaks corresponding to a return signal or signals (see e.g., step S104 in FIG. 5). For example, in one or more embodiments, the peak finding step may be performed to identify one or more desired peaks, P1, P2, P3, P4, P5, P6, etc. corresponding to a return signal or signals from S1, S2, S3, S4, S5, S6, etc., respectively.

In one or more embodiments, the apparatus or system, or method being performed, may determine rotary junction health, and/or apparatus/system health, using the one or more peaks (see e.g., step S105 in FIG. 5). In one non-limiting, non-exhaustive embodiment example, either or both of peaks P1 and P2 may be used to determine rotary joint health and/or apparatus/system health up to the stationary or fixed section of the rotary joint (see e.g., surfaces S1 and S2 and surrounding portions of at least the rotary joint in FIG. 4, for example). By way of another non-limiting, non-exhaustive embodiment example, either or both of peaks P3 and P4 may be used to determine rotary joint and/or apparatus/system health up to the rotatable section of the rotary joint (see e.g., surfaces S3 and S4 and surrounding portions of at least the rotary joint in FIG. 4, for example). In one or more embodiments, a differential value between the rotatable section and stationary/fixed section may be used to determine a change in insertion loss across the rotary joint. In one or more non-limiting, non-exhaustive embodiments, insertion loss rotational variation, an important metric to obtain uniform images circumferentially, may be obtained by rotating the rotatable section of the rotary joint and by measuring insertion loss at different angles. In one non-limiting, non-exhaustive embodiment example, insertion loss may be measured at two or more discrete angles. In another non-limiting, non-exhaustive embodiment example, insertion loss may be measured as the rotatable section of the rotary joint is continuously rotated. In another non-limiting, non-exhaustive embodiment example, either or both of P5 and P6 may be used to determine rotary joint health and/or apparatus/system health up to the Sacrificial Interface (see e.g., any sacrificial interface shown in any of FIGS. 3A-3G and/or FIG. 4, any sacrificial interface discussed herein, or any sacrificial interface known to those skilled in the art that may be used with a rotary joint, etc.). In one or more embodiments, a reflection from surface S6 may be used to assess whether an endface (e.g., of surface S6, of the rotary joint, of the PIU, etc.) is dirty by tracking an absolute return loss (absolute RL) signal before and/or after each optical probe engagement/disengagement process that may be performed for the apparatus/system (e.g., the system 100, the system 100', the system 100", the system 100''', any other system discussed herein, etc.). Absolute RL refers to the return loss (RL) measured at a peak taking into account any different insertion losses up to that point. In one or more embodiments, the rotary joint health and/or apparatus/system health may be stored in one or more memories (see e.g., step S106 of FIG. 5). In one or more embodiments, step S106 may be omitted, or may be replaced with, or used together with, a step that displays the rotary junction/joint health and/or the apparatus/system health on a display.

Figure 6:
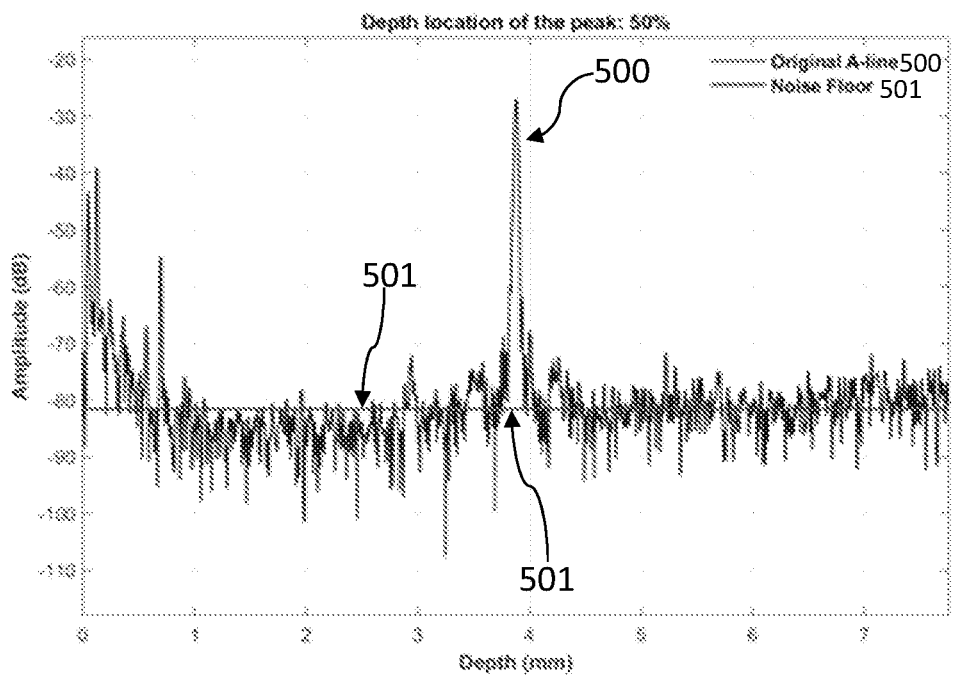
FIG. 6 is a graph showing at least one embodiment of an A-line as a function of depth in accordance with one or more aspects of the present disclosure.

In one or more non-limiting, non-exhaustive embodiment examples, rotary joint health and/or apparatus/system health may be determined, using the one or more peaks, from a measurement of sensitivity, resolution, or both. For example, a peak value for a specific peak of the one or more peaks may be calculated and compared to the noise floor to measure signal-to-noise ratio (SNR). Sensitivity may be measured by subtracting the specific peak's return loss RL from the measured SNR per Equation 1 shown below, where RL is the specific peak's return loss (which may be measured beforehand and stored in the apparatus/system or any other storage device in one or more embodiments). FIG. 6 depicts a typical A-line that may be obtained from any one or more of the surfaces (e.g., any one or more of S1 through S6, any combination of surfaces S1 through S6, etc.) described earlier. In at least one example, the peak P3 from surface S3 may be identified, and the delay line may be adjusted to place a peak reflection in a middle of an imaging range. In some examples, the peak reflection may be placed at a specific depth or location in the imaging range (such as, but not limited to, for example: 10%, 50%, or 90%). For consistency, the measurement may be performed at the same or similar specific depth in one or more embodiments, with a minor deviation from a nominal value, for example 50%±2% or 50%±5%. In other words, the measurement may be performed at a same or similar specific depth within a predetermined or set deviation range (e.g., a predetermined or set value±2%, a predetermined or set value±3%, a predetermined or set value±4%, a predetermined or set value±5%, etc.). A noise floor may be determined using any consistent noise floor determination method. By way of at least one example, a noise floor may be determined as the mean of a predetermined or selected A-line, the median of a set of A-lines, or the mean or the median of a subset of the A-line(s) (e.g., a group or subset of A-line(s) taken from a larger set or plurality of A-lines). The subset of the A-line(s) may be a set number of samples with a smallest amplitude or a specific number of samples about, or a fixed distance away from, the specific peak.

$$\text{Sensitivity} = \text{SNR} - \text{RL}. \qquad \text{Equation 1:}$$

Figure 7:
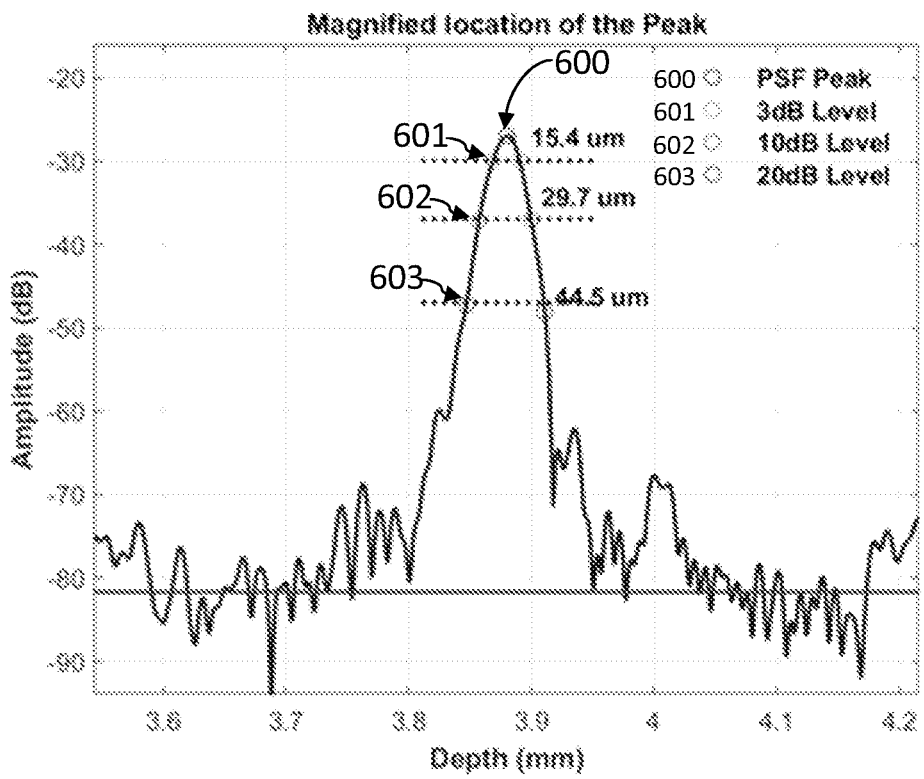
FIG. 7 is a graph showing the least one embodiment of an A-line as a function of depth of FIG. 6 that is zoomed-in about or around a peak depth in accordance with one or more aspects of the present disclosure.

FIG. 7 shows a zoomed-in version about the peak (or the specific peak) from FIG. 6. The width of the peak PSF may be determined or predetermined at a specific percent or decibel (dB) reduction from a maximum peak value. For example, in one or more embodiments, the measurement may be made at the −3 dB level (other values may be chosen instead and are not limited to the −3 dB level, the −10 dB level, or the −20 dB level shown in FIG. 7) to determine resolution.

In the example of FIGS. 6-7, the reflection peak measured at −26.8 dB, and the noise floor was calculated as the median of the A-line measured at −81.6 dB corresponding to a SNR of 54.8 dB. Peak RL, previously characterized/determined and measured at −64.3 dB, corresponded to an apparatus/system sensitivity of 119.1 dB per equation 1 above. In a case where, during apparatus/system self-diagnosis, the peak RL measures differently, then the rotary joint and/or apparatus/system health is in question and further evaluated. For example, after predetermined or set handling (e.g., rough handling, stress testing, etc.) of the apparatus/system, the rotary joint was significantly rattled, which caused misalignment of the rotary joint optics. A measurement had the peak RL measure or value at −14.7 dB, and the noise floor measure or value at −81.4 dB which corresponds to a SNR of 66.7 dB. One may compare the original SNR to the measured SNR to conclude that the difference is significant or may calculate RL. Calculating RL is preferable, in one or more embodiments, even in a case where such a process or step takes an extra calculation to determine the RL since the calculation allows for a more accurate comparison, especially when correcting RL value by insertion loss IL up to the peak in question. In this example the peak RL measured at −52.4 dB, which was calculated by subtracting sensitivity value (119.1 dB) from SNR (66.7 dB). This is an increase of 11.9 dB for the peak reflection, which is a good indicator of the optics misalignment and hence a state of the apparatus/system in one or more embodiments.

In one or more other embodiments, rotary joint health and/or apparatus/system sensitivity health may be determined by comparing a measured peak value to an initially recorded value (e.g., at a factory during or after manufacture).

In one or more embodiments, multiple indicators may be used to evaluate a state of a rotary joint health and/or an apparatus/system health. For example, one or more methods or techniques may use one or more of (or a combination of) the aforementioned indicators (e.g., comparing original SNR to the measured SNR, evaluating or calculating RL and comparing same to values for the peak reflection, comparing a measured peak value to an initially recorded value, etc.).

Using one or more of the features or techniques of the present disclosure, one or more embodiments may achieve one or more of the following: (i) get a direct measurement of rotary joint health (or optical health) and/or apparatus/system health (or optical health); (ii) determine rotary joint health without an optical probe or catheter connection which typically is a single-use device; (iii) determine sacrificial interface quality without disconnecting the sacrificial interface and without visual inspection aids; and/or (iv) determine apparatus/system sensitivity as a function of rotary joint rotation angle.

In one or more embodiments, an apparatus/system for increasing imaging depth range may include: an OCT apparatus/system; a reference reflection adjusted so that a reflection from a rotary joint of the apparatus/system is visible in an imaging field of view; and one or more processors that operate to perform data processing step(s) to determine rotary joint health and/or apparatus/system health.

Peak value may be used instead of SNR for all embodiments. Also, a single A-line, or two or more averaged A-lines, may be used to determine a peak (or peaks) and/or SNR in one or more embodiments.

The PIU linear stage actuation causes no change in optical length in one or more of the embodiment designs discussed herein, and this also may apply to apparatuses or systems where the total length of the signal path changes as the linear stage of the PIU moves. In one or more embodiments, an optical delay line may be used in an application similar to the embodiments and applications shown in FIGS. 3A, 3D, and 3F, and the optical delay line may move proportional to the linear stage of the PIU keeping the imaging depth consistently at the end face of the PIU-Catheter interface.

The Optical Delay line as depicted in FIGS. 3D and 3F may be used to maintain imaging depth as the PIU linear stage moves, changing the optical length from the module to the PIU-Catheter interface.

In one or more embodiments, intraluminal imaging may be used to acquire high-resolution cross-sectional images of tissues or materials, and to enable real time visualization. Intraluminal imaging may employ automatic connection and disconnection of an optical probe/catheter to an imaging system. In one or more embodiments, knowing a status of the probe/catheter connection improves or maximizes system performance/functionality. One or more embodiments properly mate and/or confirm proper mating of the probe/catheter connection to yield useful data, and to improve or maximize time of a physician.

Accordingly, it is at least one broad object of the present disclosure to provide one or more optical apparatuses, systems, methods (for using and/or manufacturing) and storage mediums, such as, but not limited to, fiber optic catheters, endoscopes and/or optical coherence tomography (OCT) apparatuses and systems, and methods and storage mediums, for use with same, to achieve consistent, reliable detection and/or self-diagnosis results (e.g., determining rotary junction health (e.g., optical health) or status, determining apparatus/system health (e.g., optical health) or status, health or status for the rotary joint and the apparatus/system, etc.), including at a high efficiency, and at a reasonable cost of manufacture and maintenance.

In one or more embodiments, the A-line signal (e.g., as shown in each of FIGS. 6-7) may be processed in one or more ways, such as those ways, methods, techniques, etc. discussed in U.S. Pat. App. No. 62/944,064, filed on Dec. 5, 2019, the disclosure of which is incorporated by reference herein in its entirety, and discussed in U.S. patent application Ser. No. 17/098,042, filed on Nov. 13, 2020, the disclosure of which is incorporated by reference herein in its entirety. For example, one or more of the A-line signals may be smoothed by a 2D Gaussian filter for more reliable and accurate peak detection. Preferably, in one or more embodiments, special care or step(s) may be taken to avoid any phase delay introduced by any filtering so that the pulse location is not shifted. After such filtering, a much smoother A-line signal may be obtained. By way of at least another example, in one or more method embodiments, additional filtering (e.g., 1D filtering) may be performed to smooth A-lines. The pulse in the one-dimensional signal may correspond to a vessel wall. The rising edge of the pulse may be where the edge pixel of the A-line lies. By detecting the edge pixel in each A-line, the two-dimensional edge detection issue may be converted into a simpler one-dimensional pulse detection issue. In other words, one or more embodiments of the present disclosure may simplify at least one lumen edge, stent, and/or artifacts detection approach and provide a solution at the same time.

In one or more embodiments, an additional step of finding and calculating the peaks and width parameters for lumen edge, stent(s) and/or artifact(s) may be performed, for example, as discussed in U.S. Pat. App. No. 62/944,064, filed on Dec. 5, 2019, the disclosure of which is incorporated by reference herein in its entirety, and as discussed in U.S. patent application Ser. No. 17/098,042, filed on Nov. 13, 2020, the disclosure of which is incorporated by reference herein in its entirety. In one or more embodiments, the peak or threshold (or other measurements/calculations) information may be applied to detecting and diagnosing one or more optical connections. In one or more embodiments, for each A-line signal, the highest peak may be detected within the proper FOV range. In at least one embodiment, there may be three (3) types of widths defined for the detected peak. The first may be a half-max width that may be detected using an adaptive threshold based on mean and maximum values of the smoothed A-line. By way of at least one embodiment example, the threshold may be computed, as follows:

$$\text{Threshold} = (\text{mean} + \text{peak})/2,$$

where "mean" is the average of the smoothed A-line and "peak" is the maximum value of the smoothed A-line. This threshold may be used to detect the most significant pulse corresponding to the lumen edge in a specific A-line. Any pulse above the threshold may be an edge pulse candidate in one or more embodiments. The largest pulse among all the candidates in terms of area under the pulse may be considered to be the maximum peak (or the "most significant pulse"). The second width of the highest peak may be defined as the one dimensional gradient signal along the A-line in the vicinity of the maximum peak, and may be used to identify the exact location of the lumen edge point in the smoothed A-line. The third width of the same peak may be defined along the A-line similar to the second width. However, for the third width, the gradient value will drop from its peak value to zero, which indicates the point that the value change stops and begins reversing its direction. By placing together all the lumen edge points thus detected from all the A-lines in one or more embodiments, the lumen edge for the vessel may be formed as a function of maximum peak locations vs. A-line indices.

As a further example, another approach to find the threshold is to find the average between the max peak and min peak as:

Threshold=(min+peak)/2.

A further alternative approach is to find the threshold based on the max peak as:

Threshold=(peak)×2/3.

The location of the highest peak of the one dimensional gradient signal along the A-line in the vicinity of the maximum peak may be used to identify the exact location of the lumen edge point in the smoothed A-line. Again, in one or more embodiments, the lumen edge data may contain or include artifact edge pixels.

In one or more embodiments, a guide wire artifact may be determined/detected and removed as discussed in U.S. Pat. App. No. 62/944,064, filed on Dec. 5, 2019, the disclosure of which is incorporated by reference herein in its entirety, and as discussed in U.S. patent application Ser. No. 17/098, 042, filed on Nov. 13, 2020, the disclosure of which is incorporated by reference herein in its entirety.

In one or more instances, a guide wire region may have a strong reflection, which corresponds to higher peak values. A guide wire region also may cover a larger range in terms of A-lines and often may have a strong relection at the center A-lines. When a guide wire and stents both exist or are used in one or more embodiments, some stents struts may overlap with the guide wire, and the shadow regions may be extended by the stent(s). For those kind of conditions, identifying the guide wire correctly helps the further process to extract other stents.

One or more embodiments of the guide wire search process may be defined as or may include, as discussed in U.S. Pat. App. No. 62/944,064, filed on Dec. 5, 2019, the disclosure of which is incorporated by reference herein in its entirety, and as discussed in U.S. patent application Ser. No. 17/098,042, filed on Nov. 13, 2020, the disclosure of which is incorporated by reference herein in its entirety, one or more of the following: a) starting from the maximum peak values for all A-lines; b) growing the neighbor edge until either location or width jump finds a boundary point; c) continuing to grow around the boundary untill the tissue only peak/edge pair is reached; d) growing back from the tissue only peak/edge pair until the end is reached; e) conducting the process on both directions; f) defining the range of the A-lines to include the tissue only peaks on both sides as the shadow range; g) calculating a shadow profile behind the tissue peaks to confirm the shadow does indeed exist; h) when the shadow is confirmed, the guide wire region is then confirmed; otherwise, iterate or repeat the process steps (a) to (h) with the next maximum peak value.

After the guide wire region has been identified, in one or more embodiments, the edge points may not be considered (and are, in one or more embodiments, preferably not considered) as the lumen edge and may be removed for stent detection step(s) that follow.

In one or more embodiments, stent detection may be performed as discussed in U.S. Pat. App. No. 62/944,064, filed on Dec. 5, 2019, the disclosure of which is incorporated by reference herein in its entirety, and as discussed in U.S. patent application Ser. No. 17/098,042, filed on Nov. 13, 2020, the disclosure of which is incorporated by reference herein in its entirety. For example, stents may be detected by identifying stent strut candidates using one or more techniques, such as, but not limited to, edge jump stent detection, narrow peak width stent detection, etc. By way of at least one further example, stent strut candidates may be identified using location and peak width jumps. Confirmation and removal of the stent strut obstructed lumen edge points may share similar steps as done for sheath and/or guide wire detection and removal, but in a more iterative approach in one or more embodiments. First, in at least one embodiment, the major peak and edge profile for the whole lumen may be obtained with the guide wire removed. When there is/are stent(s) present in front of the lumen edge, the edge position jumps may indicate the possible stent candidates. For stents which are very close to the lumen edge either on one side or both sides, the stents and/or stent candidates may be identified by looking into the profile of the peak widths. The stent strut peaks tend to have small and equal peak widths compared to neighbor lumen peaks and corresponding edges.

In one or more embodiments, stent detection may be performed by merging and extending a stent region as discussed in U.S. Pat. App. No. 62/944,064, filed on Dec. 5, 2019, the disclosure of which is incorporated by reference herein in its entirety, and as discussed in U.S. patent application Ser. No. 17/098,042, filed on Nov. 13, 2020, the disclosure of which is incorporated by reference herein in its entirety. Following the above lists or listing of stent strut candidates, in one or more embodiments, the search process may be conducted locally on each candidate to find the neighbor lumen edges on both sides of the stent strut. In at least one embodiment, the neighbor lumen edges are further extended until the connected peak and edge may no longer be confirmed to be a valid lumen edge. The covered region may be marked as confirmed edges. During one or more embodiments of the process, the candidates coming from different detection methods may have duplicates such that sets of candidates overlap. As such, the overlapping condition and the duplicates may be checked before proceeding on to the next step. Once all candidates are processed, the whole lumen edge circle may be marked as confirmed edges. Broken segments may be identified, and reasons for doing so are explained to at least confirm that the candidates and broken segments are all valid results.

In one or more embodiments, a shadow profile of the stent strut candidates may be calculated and/or a shadow pattern may be confirmed for an identified or found stent center location as discussed in U.S. Pat. App. No. 62/944,064, filed on Dec. 5, 2019, the disclosure of which is incorporated by reference herein in its entirety, and as discussed in U.S. patent application Ser. No. 17/098,042, filed on Nov. 13, 2020, the disclosure of which is incorporated by reference herein in its entirety. For each stent, the interpolated lumen edge may exist between lumen edges on each of the sides, which is behind the detected peak and edge of the stent, in one or more embodiments. Based on the interpolated lumen peak position, the shadow accumulation profile may be calculated. In at least one embodiment, a normal shape of the shadow accumulation profile or shadow profile may be a single valley with a nadir (e.g., foot, base, lowest point, etc.) at, substantially at, or near the center of the valley. The minimum value location may be identified as the stent center, which corresponds to a middle of the stent strut that casted the shadow. There may exist some second reflection behind the stent shadow, which may distort the true shadow profile, in one or more embodiments. An additional process may be employed to remove the effects of such second reflections behind the stent shadow by identifying the narrow width peaks behind the interpolated lumen edge within the shadow and subtracting them from the original image.

In one or more embodiments, a lumen edge near the border may be extracted as discussed in U.S. Pat. App. No. 62/944,064, filed on Dec. 5, 2019, the disclosure of which is incorporated by reference herein in its entirety, and as discussed in U.S. patent application Ser. No. 17/098,042, filed on Nov. 13, 2020, the disclosure of which is incorporated by reference herein in its entirety. As extra steps when processing each stent strut candidates, there may be one or more valid lumen edges that exist as secondary peaks behind the stent peak near the border region. Proper extraction and inclusion of the one or more valid lumen edges that exist as secondary peaks behind the stent peak improves the quality of the lumen edge results. This is one of the several unique aspects or features or improvements of the present disclosure compared to other methods because all such A-line results are often thrown away. The extraction of such a lumen edge may be based on the connectivity of the current lumen edge by searching a secondary peak outside of the major peak on the neighborhood A-line that already has been identified or that is identified as the non-lumen peak. The process may search on both sides of the stent neighborhood A-lines until no further peak is found in one or more embodiments.

In one or more embodiments, any missing portion of the lumen edge may be interpolated to fill in missing data as discussed in U.S. Pat. App. No. 62/944,064, filed on Dec. 5, 2019, the disclosure of which is incorporated by reference herein in its entirety, and as discussed in U.S. patent application Ser. No. 17/098,042, filed on Nov. 13, 2020, the disclosure of which is incorporated by reference herein in its entirety. For example, for each confirmed stent location, any gap between or in the lumen edge may be filled using linear interpolation. Both lumen peak and edge information are kept and interpolated in one or more embodiments. After the process, the whole lumen circle may be processed and may form a closed circle-like curve for the lumen edge.

In one or more embodiments of embedded stent detection as discussed in U.S. Pat. App. No. 62/944,064, filed on Dec. 5, 2019, the disclosure of which is incorporated by reference herein in its entirety, and as discussed in U.S. patent application Ser. No. 17/098,042, filed on Nov. 13, 2020, the disclosure of which is incorporated by reference herein in its entirety, the peak curve may be similar and may be used to calculate a shadow accumulation profile or a shadow profile for the whole image. In one or more embodiments, finding an embedded stent and/or stent strut center may be based on the lumen peak curve or may be based on any other method or technique as discussed in U.S. Pat. App. No. 62/944,064, filed on Dec. 5, 2019, the disclosure of which is incorporated by reference herein in its entirety, and as discussed in U.S. patent application Ser. No. 17/098,042, filed on Nov. 13, 2020, the disclosure of which is incorporated by reference herein in its entirety. For example, in one or more embodiments of embedded stent detection, a stent peak and/or edge behind the lumen edge may be found, a peak width and/or thickness may be calculated, the stent region may be merged and extended, an embedded stent(s) may be confirmed and extracted, and strust location information may be determined/identified, etc. Following the above discussed steps, for example, to identify and confirm the stent struts, valid embedded stents may be extracted and confirmed, with its location information (such as, but not limited to, strut center location) identified as well.

In one or more embodiments, the lumen edge may be output and/or the stent strut center location (and/or other stent strut location information) may be output as discussed, for example, in U.S. Pat. App. No. 62/944,064, filed on Dec. 5, 2019, the disclosure of which is incorporated by reference herein in its entirety, and in U.S. patent application Ser. No. 17/098,042, filed on Nov. 13, 2020, the disclosure of which is incorporated by reference herein in its entirety. A 1D smoothing filter may be applied to or used on the lumen edge results. The lumen edge and/or stent strut center location information (and/or other stent strut location information) may be output to a desired format, may be stored in a memory, may be printed, may be displayed on a display, etc.

One or more embodiments may detect the peaks and edges with three types of peak widths in each one-dimensional data (A-line) as discussed in U.S. Pat. App. No. 62/944,064, filed on Dec. 5, 2019, the disclosure of which is incorporated by reference herein in its entirety, and as discussed in U.S. patent application Ser. No. 17/098,042, filed on Nov. 13, 2020, the disclosure of which is incorporated by reference herein in its entirety. In one or more embodiments, the maximum peak in each of the A-lines may be detected. The most significant pulse denotes the maximum peak and its associated front edge also named as "major peak/edge" in each of the A-lines in one or more embodiments. In one or more embodiments, a gradient of one-dimensional data (A-line) may be used to determine the edge location associated with each peak. In one or more embodiments, each peak may associate with three types of width: (1) a half-max width, (2) max gradient width, and (3) minimal value width, which defines the peak range on the A-line. The half-max width, which is the first width, may be used to test connectivity between neighbor peaks. The max gradient width, which is the second width, may be used to indicate a thickness of the object. The minimal value width, which is the third width, may be used to define the peak range. In one or more embodiments, other peaks may exist outside of a current peak range. One or more embodiments may group connected peaks on different neighbor A-lines together to form geometrically separate objects in 2D space.

One or more embodiments may distinguish the lumen edge peak from the guide wire and stent struts. For example, in one or more embodiments, disconnected major peaks in neighbor A-lines may indicate separate objects, such as a lumen edge peak and a guide wire or stent strut(s). The peak location connectivity may exist in a case where the stent strut peak edge is very close to the lumen edge in neighbor A-lines. In such cases, the lumen and stent may be separated by the jump of the peak widths. In one or more embodiments, peak widths of stent strut(s) are small and near constant, including the first, second, and third widths, because of a shadow behind the stent strut(s). Therefore, both peak location and the peak widths' values are used to separate the objects, such as a lumen edge peak and a guide wire or stent strut(s).

One or more embodiments of the present disclosure may grow major peaks into neighbor A-lines around the boundary region between the lumen and the stent strut(s) or guide wire. Multiple peaks may exist when peaks from a neighbor A-line grow by searching a local peak which is outside the major peak on the current A-line. Both a lumen edge region and stent strut objects may be grown into more complete objects that leads to an improved, optimal, and/or correct decision of the boundary between the lumen and the stent strut(s) or guide wire (which may be useful in one or more situations, including, but not limited to, some challenging cases).

One or more embodiments of the present disclosure may calculate the shadow accumulation profile (or shadow profile) locally based on the interpolation of lumen peaks on both sides of the guide wire and/or stent strut(s). In one or more embodiments, the interpolation may happen on both sides of the guide wire and the stent struts. Interpolation of lumen edge peaks may be used to calculate the shadow profile because starting points for the accumulation calculation may be critical and/or may substantially improve the accuracy in one or more embodiments. A shape of the shadow profile may be used to confirm or ensure that the area includes or contains a valid shadow. As aforementioned, a single valley shadow may be used to find a center location for a stent strut(s).

One or more embodiments may process stent candidates iteratively to complete the lumen profile for the whole image. A guide wire region may be processed first, and then each stent candidate may be processed locally for better accuracy. Both lumen peak and lumen edge curves may be generated to confirm the results.

One or more embodiments of the present disclosure may use a global lumen peak curve to calculate the shadow profile and to detect embedded stent(s). An interpolated peak curve may be used to calculate the global shadow profile in one or more embodiments, and/or the global shadow profile may be used to identify the embedded stent strut(s). In one or more embodiments, embedded stent strut(s) may be extracted using a secondary peak width pattern.

Additionally or alternatively, in one or more embodiments, a principal component analysis method and/or a regional covariance descriptor(s) may be used to detect objects, such as stents. Cross-correlation among neighboring images may be used to improve lumen edge detection result(s). One or more embodiments may employ segmentation based image processing and/or gradient based edge detection to improve detection result(s).

As discussed in U.S. Pat. App. No. 62/944,064, filed on Dec. 5, 2019, the disclosure of which is incorporated by reference herein in its entirety, and as discussed in U.S. patent application Ser. No. 17/098,042, filed on Nov. 13, 2020, the disclosure of which is incorporated by reference herein in its entirety, the OCT image in polar coordinates (e.g., of a stented vessel) may be displayed vertically (rather than, or in addition to, horizontally), and/or may be displayed with a corresponding OCT image in Cartesian Coordinates using at least one apparatus or system for performing lumen, stent, and/or artifacts detection techniques in accordance with one or more aspects of the present disclosure.

In accordance with at least one aspect of the present disclosure and as aforementioned, one or more additional methods for lumen, stent, and/or artifacts detection of OCT images are provided herein, or may be used with one or more of the features or aspects of the present disclosure, and are discussed in U.S. patent application Ser. No. 16/414,222, filed on May 16, 2019, the entire disclosure of which is incorporated by reference herein in its entirety, and in U.S. Pat. Pub. No. 2019/0374109, which was published on Dec. 12, 2019, the disclosure of which is incorporated by reference herein in its entirety.

Placing together all the lumen edge points thus detected from all the A-lines forms the lumen edge (in one or more embodiments, the lumen edge data may contain or include artifact edge pixels) for the vessel as a function of maximum peak locations vs. A-line indices.

In one or more method embodiments, edge points corresponding to large the falling and rising gradient ratio (FRGR) and small sized pulses may be removed as discussed in U.S. patent application Ser. No. 16/414,222, filed on May 16, 2019, the entire disclosure of which is incorporated by reference herein in its entirety, and in U.S. Pat. Pub. No. 2019/0374109, which was published on Dec. 12, 2019, the disclosure of which is incorporated by reference herein in its entirety. The falling and rising gradient ratio may be used as an indicator of the stent strut and guidewire presence if the detected lumen edge and its corresponding falling rising gradient ratio are plotted together as discussed in U.S. patent application Ser. No. 16/414,222, filed on May 16, 2019, the entire disclosure of which is incorporated by reference herein in its entirety, and in U.S. Pat. Pub. No. 2019/0374109, which was published on Dec. 12, 2019, the disclosure of which is incorporated by reference herein in its entirety.

In one or more embodiments, one may use either the pulse width or the area under the 1D signal pulse as the measure of the signal pulse size as discussed in U.S. patent application Ser. No. 16/414,222, filed on May 16, 2019, the entire disclosure of which is incorporated by reference herein in its entirety, and in U.S. Pat. Pub. No. 2019/0374109, which was published on Dec. 12, 2019, the disclosure of which is incorporated by reference herein in its entirety.

Using the noticeable differences of the falling raising gradient ratio and the differences in a size of the A-line pulses, the artifact region locations corresponding to the guidewire and stent struts in the detected lumen edge may be identified using simple thresh holding where the threshold may be set, for example, as:

$$\text{PulseSizeThreshold} = \text{mean} - \text{sigma} \times k1$$

Or $$\text{FRGRThreshold} = \text{mean} + \text{sigma} \times k2,$$

where "mean" and "sigma" are the mean and standard deviation of the corresponding signal, and k1, k2 are empirical parameters preferably chosen, but not limited to, between 1 to 2.

An alternative approach to calculate the thresholds may be:

$$\text{PulseSizeThreshold} = \text{mean} + (\text{peak} - \text{mean})/3$$

Or $$\text{FRGRThreshold} = \text{mean} + (\text{peak} - \text{mean})/3$$

Furthermore, as another alternative, the thresholds may also be calculated as:

$$\text{PulseSizeThreshold} = \text{peak} - (\text{peak} - \text{mean})/2$$

Or $$\text{FRGRThreshold} = \text{peak} - (\text{peak} - \text{mean})/2$$

Preferably, in one or more embodiments, these identified edge points are not considered as the lumen edge and are not used for lumen parameter calculation.

One advantage of using one dimensional A-line signal processing for lumen edge detection is that there may be a multi-peak pattern of these boundary regions from the A-line signal because both stents and lumen edge peaks exist in the A-line signal. For example, as discussed in U.S. patent application Ser. No. 16/414,222, filed on May 16, 2019, the entire disclosure of which is incorporated by reference herein in its entirety, and as discussed in U.S. Pat. Pub. No. 2019/0374109, which was published on Dec. 12, 2019, the disclosure of which is incorporated by reference herein in its entirety, the boundary region may produce clustered multi-peak pulses in the A-line signal. Multi-peak pulses may be detected using the same threshold used in the maximum peak detection step as discussed above, and is not repeated herein as a result. If a falling edge of a peak rises again before the falling edge falls below the threshold, a multi-peak pulse is considered to be identified in at least one embodiment. Preferably, if a pulse is detected as a multi-peak pulse, the lumen edge data from that A-line may be considered as the boundary region of the stent struts and guidewire and removed from lumen edge detection. In one or more embodiments, multi-peaks not in the boundary region may be retained, and are preferably retained in one or more embodiments.

Even if a falling edge of a peak falls below the threshold and then raises again to form another peak, it may still be considered as a multi-peak pulse. The correct identification of the lumen edge may then rely on the major peak detection and the size of the front peak in at least one embodiment. If the front peak is identified as the artifacts, such as, but not limited to, a stent or guidewire, the second peak may be the lumen edge. There may be small vessel branch presented in the tissue underneath the vessel wall, which may end up manifesting as two separate peaks in a single A-line in a similar manner in one or more embodiments. In such a case, the front peak without the narrow width may be the lumen edge. At least one way to distinguish multi-peak pulses between the valid lumen edge versus an influence of one or more artifacts is determining whether they are located within the boundary regions. Therefore, the mutli-peak cases may be further classified into the non-boundary region and boundary region cases, and they may be removed from the detected lumen edge only in the boundary regions.

By way of another example and alternative to the aforementioned example, horizontal gradients may be used to identify and remove the lumen edge data corresponding to the boundary region between the soft tissue and narrow artifacts. As discussed in U.S. patent application Ser. No. 16/414,222, filed on May 16, 2019, the entire disclosure of which is incorporated by reference herein in its entirety, and as discussed in U.S. Pat. Pub. No. 2019/0374109, which was published on Dec. 12, 2019, the disclosure of which is incorporated by reference herein in its entirety, a gradient across the A-lines may display a pattern of many shadows (which may include one or more artifact shadows) caused by the light blocking artifacts.

For each detected lumen edge point, the average values of across the A-lines gradient below the edge point may be computed as discussed in U.S. patent application Ser. No. 16/414,222, filed on May 16, 2019, the entire disclosure of which is incorporated by reference herein in its entirety, and as discussed in U.S. Pat. Pub. No. 2019/0374109, which was published on Dec. 12, 2019, the disclosure of which is incorporated by reference herein in its entirety. These average values reflect the locations of the shadows caused by the light blocking artifacts. Given the directional property of the gradient across the A-lines, the bright to dark edge produces a rising peak while the dark to bright edge produces a falling peak. For each dark shadow produced by the stent strut, the shadow is bordered by a rising peak at one side and by a falling edge at the other side.

In one or more method embodiments, edge points corresponding to multi-pulse A-lines may be removed as discussed in U.S. patent application Ser. No. 16/414,222, filed on May 16, 2019, the entire disclosure of which is incorporated by reference herein in its entirety, and in U.S. Pat. Pub. No. 2019/0374109, which was published on Dec. 12, 2019, the disclosure of which is incorporated by reference herein in its entirety. For example, lumen edge data corresponding to a ghost signal or ghost signals produced (e.g., from reflection(s) of stent(s), any signal(s) other than the targeted signal, a luminance signal, etc.) may be identified and removed by detecting multiple pulses.

When there is strong reflection caused by the stent struts or guidewire, there may be a ghost signal or signals in the A-line signal due to a detected multipath signal. As another advantage of using one dimensional A-line signal processing for lumen edge detection, this ghost signal (or signals) manifests iteself as an additional pulse signal in the A-line signal as discussed in U.S. patent application Ser. No. 16/414,222, filed on May 16, 2019, the entire disclosure of which is incorporated by reference herein in its entirety, and in U.S. Pat. Pub. No. 2019/0374109, which was published on Dec. 12, 2019, the disclosure of which is incorporated by reference herein in its entirety. For example, an A-line plot may show two peaks in which the right peak corresponds to the ghost signal and the left peak corresponds to a stent strut as discussed in U.S. patent application Ser. No. 16/414,222, filed on May 16, 2019, the entire disclosure of which is incorporated by reference herein in its entirety, and in U.S. Pat. Pub. No. 2019/0374109, which was published on Dec. 12, 2019, the disclosure of which is incorporated by reference herein in its entirety. Peaks of all significant pulses in the A-line signal may be determined.

Given that the most likely sources of strong reflection are stent struts and guidewire, the detected lumen edge points corresponding to the A-lines with a ghost signal (or signals) are preferably excluded from the parameter calculation for the lumen.

In one or more method embodiments, a lumen edge may be formed as discussed in U.S. patent application Ser. No. 16/414,222, filed on May 16, 2019, the entire disclosure of which is incorporated by reference herein in its entirety, and in U.S. Pat. Pub. No. 2019/0374109, which was published on Dec. 12, 2019, the disclosure of which is incorporated by reference herein in its entirety. For example, after removing all the artifacts from the detected lumen edge (e.g., edge points with a narrow pulse width (which correspond to edge points from guide wire(s) and stent(s)) may be removed; edge points with large FRGR (which correspond to edge points from weak stent(s)) may be removed; edge points with separated multiple large pulses (which correspond to stents with a reflection image) may be removed; edge points with clustered multiple pulses (which correspond to the boundary of soft tissue and the stent(s)) may be removed; etc.), the gaps in the lumen edge may be filled using simple interpolation (e.g., linear interpolation) using the neighboring edge points. One embodiment example for doing this is to have the lumen edge undergo median filtering.

In one or more method embodiments, a lumen edge may be smoothed as discussed in U.S. patent application Ser. No.

16/414,222, filed on May 16, 2019, the entire disclosure of which is incorporated by reference herein in its entirety, and in U.S. Pat. Pub. No. 2019/0374109, which was published on Dec. 12, 2019, the disclosure of which is incorporated by reference herein in its entirety. For example, the lumen edge may undergo low pass filtering. In one or more embodiments, some simple median filtering and low pass filtering may be applied to lumen edge (edge locations vs. A-line pixels) to smooth and polish the final lumen edge.

In one or more method embodiments, a lumen edge may be converted into Cartesian coordinates as discussed in U.S. patent application Ser. No. 16/414,222, filed on May 16, 2019, the entire disclosure of which is incorporated by reference herein in its entirety, and in U.S. Pat. Pub. No. 2019/0374109, which was published on Dec. 12, 2019, the disclosure of which is incorporated by reference herein in its entirety.

At least one embodiment of a method for detecting lumen edges and artifacts may be summarized as follows: The OCT image in polar coordinates may be filtered using a two dimensional Gaussian filter to reduce the noise in the image. The separate gradient in vertical and horizontal directions may be computed using the Sobel filters from the filtered image. For each A-line, one-dimensional filtering is applied to further smooth the A-line signal and remove the signal offset. The gradient along the A-line direction may be further smoothed using a low pass filter. For each A-line, all the significant pulses in the A-line signal may be found, and the most significant pulse and its position may be determined as the lumen data, based on the detection threshold and the pulse size using either pulse width or area under the pulse. The falling rising gradient ratio for the most significant pulse (lumen data) in each A-line may be computed. The lumen data may be removed, and a gap may be identified if the falling rising gradient ration is larger than the threshold value. The lumen data may be removed, and a gap may be identified if the pulse size is smaller than the threshold pulse size. The lumen data may be removed, and a gap may be identified if the detected pulses are multi-peak pulse(s) or where an artifact region detected from the previous step is bordered by the rising and falling peaks of the gradient across A-lines. The lumen data may be removed, and a gap may be identified if there is more than one comparable pulse in the A-line signal. Thereafter, the gaps are filled in the lumen edge using linear interpolation. Median filtering and/or low pass filtering may be applied to the lumen edge. The lumen edge may be converted into Cartesian coordinates for display.

One or more embodiments of a method(s) for detecting lumen and artifacts may be performed with or without the filtering of the lumen edge. For example, median filtering and/or low pass filtering the lumen edge is optional in one or more embodiments. In one or more embodiments, alternative methods for smoothing the lumen edge may be used in place of the median filtering and/or low pass filtering of the lumen edge.

One or more alternative embodiments of a method(s) for detecting lumen and artifacts may be performed by detecting a signal edge pixel from each one-dimensional data (A-line). A-lines with a significant pulse peak may be selected. Each one-dimensional data (A-line) may have its own detection threshold for pulse detection, and the respective threshold may change among different A-lines in an image. A gradient of one-dimensional data (A-line) may be used to further determine the lumen edge pixel location.

One or more alternative embodiments of a method(s) for detecting lumen and artifacts may be performed by introducing an FRGR to distinguish the edges of the target or object (e.g., soft tissue), guide wire(s), stent(s) and/or any other component being used in the procedure. The pulse size of the one dimension data is introduced to distinguish the target or object (e.g., soft tissue), guide wire(s), stent(s), and/or any other component or artifact(s) related to the procedure(s).

One or more alternative embodiments of a method(s) for detecting lumen and artifacts may be performed by identifying the boundary region between the target or object (e.g., soft tissue) and the stent strut(s), guide wire(s), or other artifacts. Multiple peaks in an A-line may represent a blurred boundary between the target or object (e.g., soft tissue) and the stent strut(s), guide wire(s), or other artifacts. The multi-peaks may be used as a signature to identify the boundary.

One or more alternative embodiments of a method(s) for detecting lumen and artifacts may be performed by identifying the boundary region between the target or object (e.g., soft tissue) and narrow stent strut(s). Variation of the gradient along the horizontal direction (across the A-lines) in the region behind the detected lumen edge may be utilized to improve the determination of the location of the artifact region.

One or more alternative embodiments of a method(s) for detecting lumen and artifacts may be performed by identifying ghost signal(s) produced from reflection of stent(s). A ghost signal may cause multiple peaks in an A-line signal. One way to handle this is to remove the area where the multiple pulses/peaks are detected.

As aforementioned for one or more embodiments of a method(s) for detecting lumen and artifacts, interpolation may be used to sample the data that is removed, and to form the lumen edge. The final edge may be smoothed or polished using filters as aforementioned.

A computer, such as the console or computer 1200, 1200', may perform any of the steps, processes, and/or techniques discussed herein for any apparatus and/or system being manufactured or used, including, but not limited to, apparatus or system 100, apparatus or system 100', apparatus or system 100", apparatus or system 100''', any of the embodiments shown in FIGS. 3A-3G, any other apparatus or system discussed herein, etc.

Figure 8:
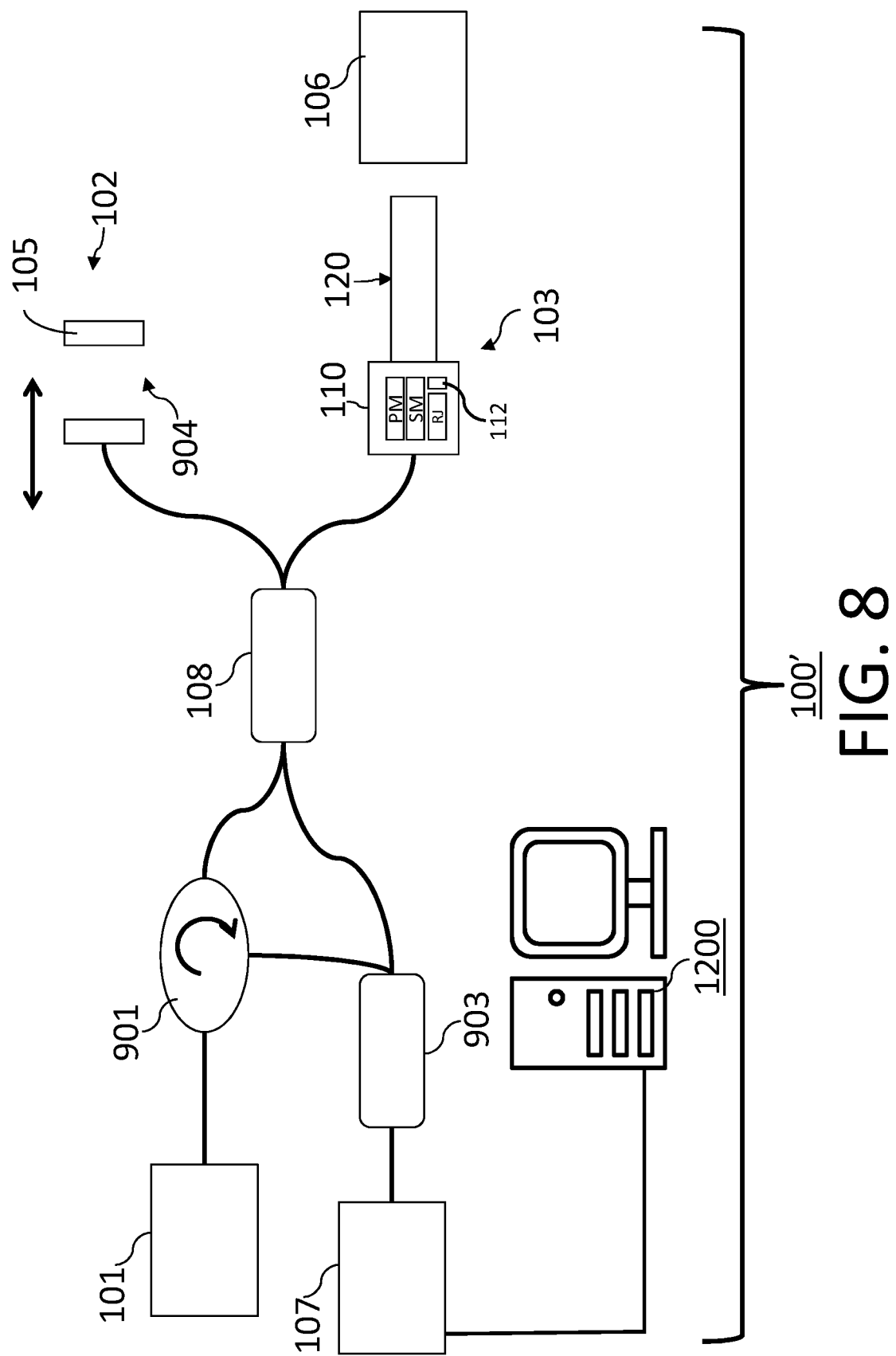
FIG. 8 is a diagram showing an embodiment of at least another system which may utilize one or more self-diagnosis techniques and/or one or more imaging techniques in accordance with one or more aspects of the present disclosure.

In accordance with one or more further aspects of the present disclosure, bench top systems may be utilized with one or more imaging modalities (such as, but not limited to, angiography, Optical Coherence Tomography (OCT), Multi-modality OCT (MM-OCT), near-infrared auto-fluorescence (NIRAF), near-infrared fluorescence (NIRF), OCT-NIRAF, OCT-NIRF, etc.) for the techniques, such as, but not limited to, the detecting and/or guiding optical connection techniques, and the self-diagnosing of rotary joint health and/or apparatus/system health, disclosed herein. FIG. 8 shows an example of a system 100' that may utilize the detecting and/or guiding, and the rotary joint health (e.g., optical health) and/or the apparatus/system health (e.g., optical health) self-diagnosis, techniques for a bench-top such as for ophthalmic applications. A light from a light source 101 delivers and splits into a reference arm 102 and a sample arm 103 with a deflecting (or deflection) section 108. A reference beam goes through a length adjustment section 904 (which is optional in one or more embodiments) and is reflected from a reference mirror (such as reference mirror or reference reflection 105 shown in FIG. 1) in the reference arm 102 while a sample beam is reflected or scattered from a sample, target or object 106 in the sample arm 103 (e.g., via the PIU 110 and the catheter 120). In one embodiment, both beams combine at the deflecting/deflection section 108 and generate interference patterns. In one or more embodiments, the beams go to the combiner 903, and the combiner 903 combines both beams via the circulator 901 and the deflecting section 108. The combined beams preferably are delivered to one or more detectors (such as the one or more detectors 107). The output of the beam splitter (see e.g., beam splitter 104 in FIG. 1), the deflecting section 108, and/or an interferometer is continuously acquired with one or more detectors, such as the one or more detectors 107. The electrical analog signals are converted to the digital signals to analyze them with a computer, such as, but not limited to, the computer 1200 (see FIG. 1; also shown in FIGS. 3A-3G, 8-10, and 12 discussed further below), the computer 1200' (see e.g., FIG. 13 discussed further below), any other computer or processor discussed herein, etc.

Figure 9:
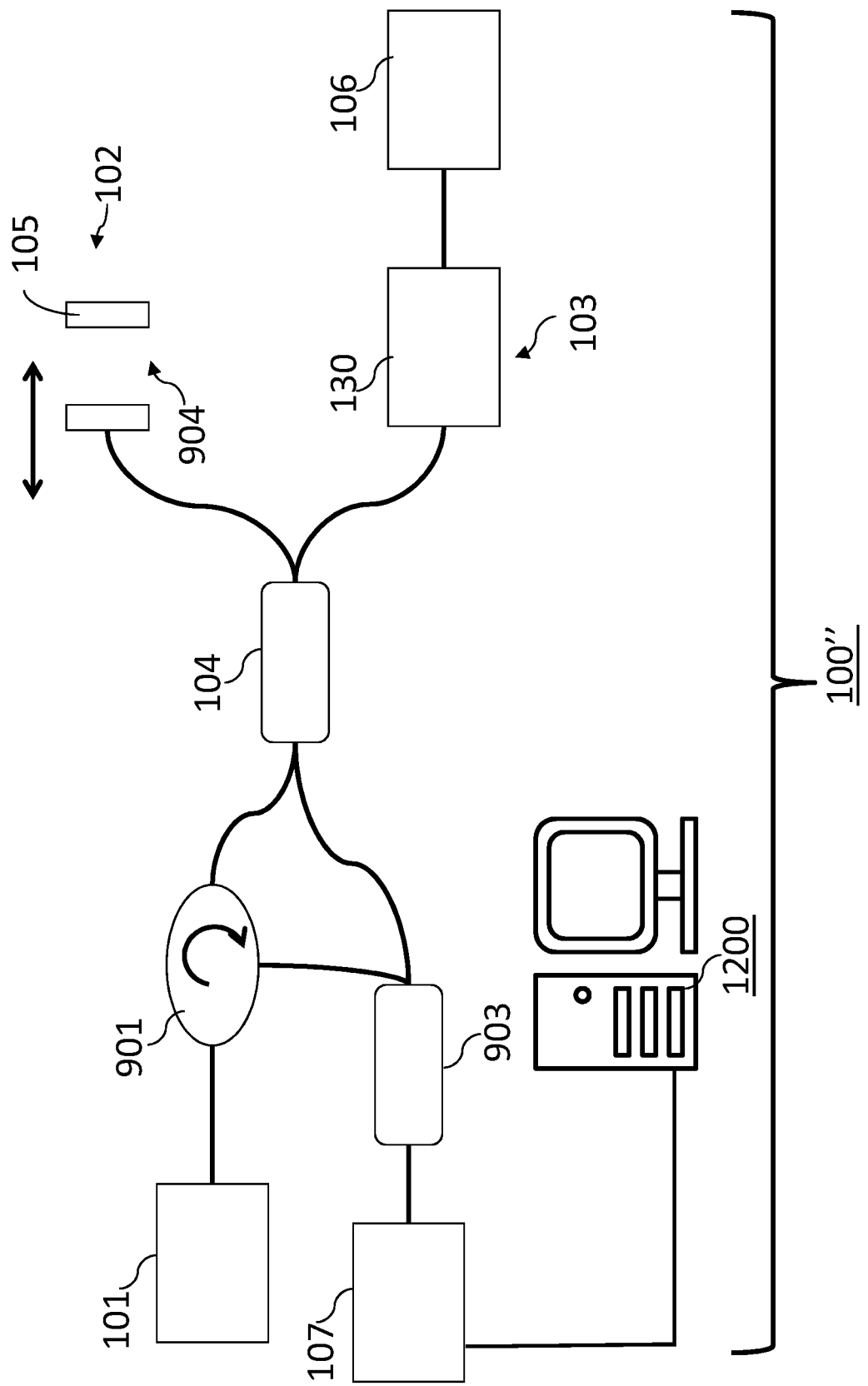
FIG. 9 is a diagram showing an embodiment of at least a further system which may utilize one or more self-diagnosis techniques and/or one or more imaging techniques in accordance with one or more aspects of the present disclosure.

In one or more embodiments, the sample arm 103 may include a phase shift unit 103 for a bench top system(s) as shown in system 100" in FIG. 9. The sample 106 may be located at the place of the mirror 105 used with the phase shift unit 130 (e.g., as shown in FIG. 1). A light from a light source 101 delivers and splits into a reference arm 102 and a sample arm 103 with a splitter 104. A reference beam goes through a length adjustment section 904 and is reflected from a reference mirror (such as reference mirror 105 shown in FIGS. 8-10) in the reference arm 102 while a sample beam is reflected or scattered from a sample, target and/or object 106 through a phase shift unit (such as the phase shift unit 130) in the sample arm 103. In one embodiment, both beams combine at the splitter 104 and generate interference patterns. In one or more embodiments, the beams go to the combiner 903, and the combiner 903 combines both beams via the circulator 901 and the splitter 104, and the combined beams are delivered to one or more detectors (such as the one or more detectors 107). The output of the beam splitter 104 and/or an interferometer is continuously acquired with one or more detectors, such as the one or more detectors 107. The electrical analog signals are converted to the digital signals to analyze them with a computer, such as, but not limited to, the computer 1200 (see FIG. 1; also shown in FIGS. 3A-3G and in FIGS. 8-10 and 12 discussed further below), the computer 1200' (see e.g., FIG. 13 discussed further below), any other computer or processor discussed herein, etc.

There are many ways to compute rotation, intensity, or any other measurement discussed herein, and/or to control and/or manufacture a device/apparatus, system and/or storage medium, digital as well as analog. In at least one embodiment, a computer, such as the console or computer 1200, 1200', may be dedicated to control and/or use devices, systems, methods and/or storage mediums for use therewith described herein. In one or more embodiments, the device/apparatus, system, method, and/or storage medium may be for MMOCT or OCT (or any other imaging modality discussed herein or known to those skilled in the art).

Figure 10:
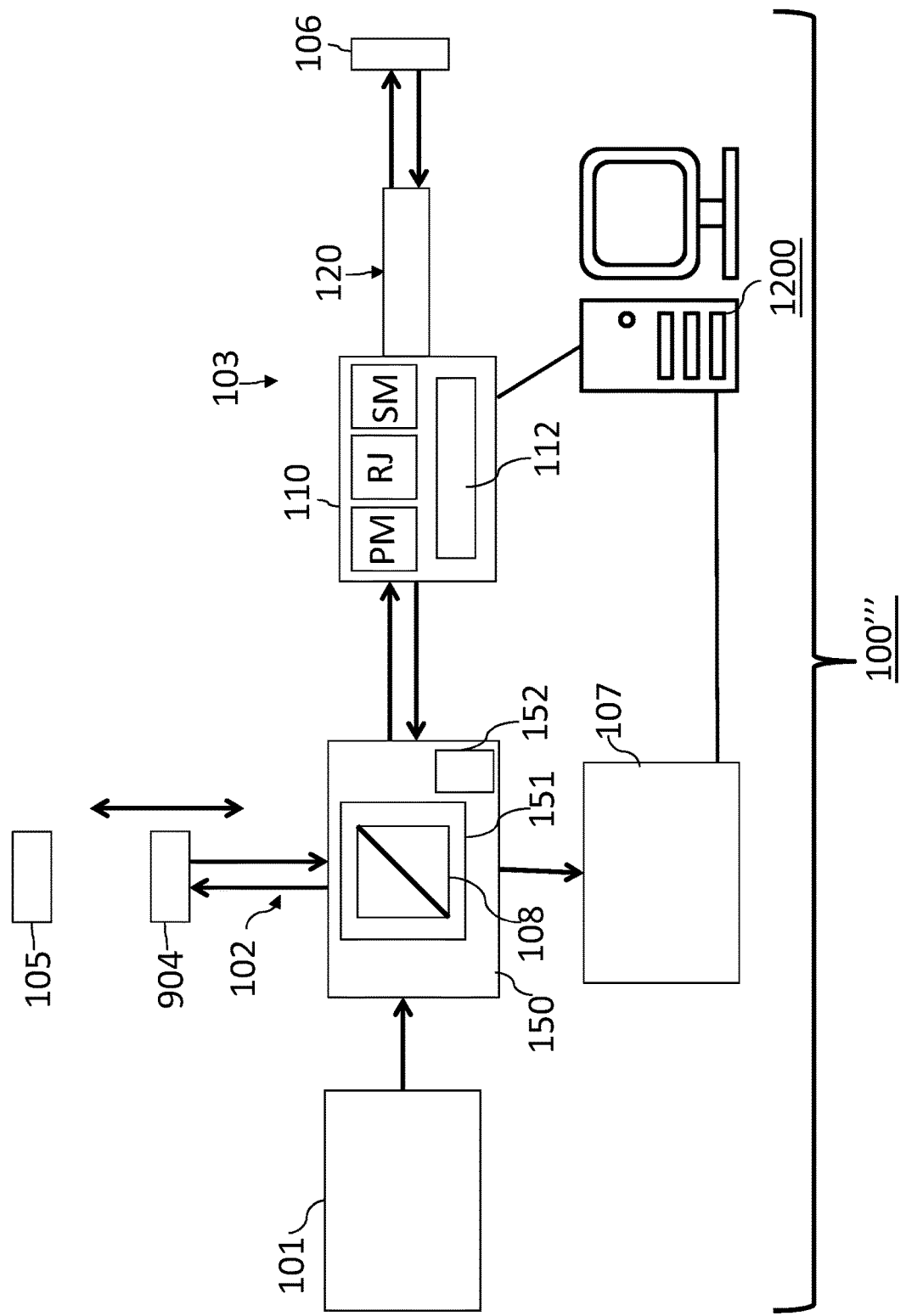
FIG. 10 is a diagram showing an embodiment of at least yet a further system which may utilize one or more self-diagnosis techniques and/or one or more imaging techniques in accordance with one or more aspects of the present disclosure.

In accordance with one or more further aspects of the present disclosure, one or more other systems may be utilized with the detecting and/or guiding, and the rotary joint health (e.g., optical health) and/or the apparatus/system health (e.g., optical health), techniques disclosed herein. FIG. 10 shows an example of a system 100''' that may utilize the detecting and/or guiding, and the rotary joint health (e.g., optical health) and/or the apparatus/system health (e.g., optical health), techniques such as for ophthalmic applications. A light from a light source 101 delivers and splits into a reference arm 102 and a sample arm 103 with a deflecting section 108 (e.g., a beam splitter or other deflecting or deflected section discussed herein) located inside of an OCT imaging engine 150, which may also include an OCT interferometer 151 (which may house or include the deflecting section 108) and a swept source engine 152 in one or more embodiments. A reference beam may pass through a length adjustment section 904, which may operate to change the distance of a reference mirror (such as reference mirror or reference reflection 105; also shown in FIG. 1) and is reflected from the reference reflection 105 in the reference arm 102 while a sample beam is reflected or scattered from a sample, target or object 106 in the sample arm 103. In one embodiment, both beams combine at the deflecting section 108 and generate interference patterns. In one or more embodiments, the combined beams are delivered to one or more detectors. The output of the interferometer 151 is continuously acquired with one or more detectors, such as the one or more detectors 107. The electrical analog signals are converted to the digital signals to analyze them with a computer, such as, but not limited to, the computer 1200 (see e.g., FIG. 1; also shown in FIGS. 3A-3G and in FIGS. 8-10 and 12 discussed further below), the computer 1200' (see e.g., FIG. 13 discussed further below), etc. In one or more embodiments, the sample arm 103 includes the PIU 110 and the catheter 120 so that the sample beam is reflected or scattered from the sample, patient (e.g., blood vessel of a patient), target, or object 106 as discussed herein. In one or more embodiments, the PIU 110 may include one or more motors to control the pullback operation of the catheter 120 (or one or more components thereof) and/or to control the rotation or spin of the catheter 120 (or one or more components thereof). For example, the PIU 110 may include a pullback motor (PM) and a spin motor (SM), and/or may include a motion control unit (MCU) 112 that operates to perform the pullback and/or rotation features using the pullback motor PM and/or the spin motor SM. As discussed herein, the PIU 110 may include a rotary junction (e.g., rotary junction RJ as shown in FIGS. 8 and 10). The rotary junction RJ may be connected to the spin motor SM so that the catheter 120 may obtain one or more views or images of the sample 106. The computer 1200 (or the computer 1200') may be used to control one or more of the pullback motor PM, the spin motor SM and/or the motion control unit 112. An OCT system may include one or more of the OCT engine 150, a computer (e.g., the computer 1200, the computer 1200', etc.), the PIU 110, the catheter 120, a monitor, etc. One or more embodiments of an OCT system may interact with one or more external systems, such as, but not limited to, an angio system, external displays, one or more hospital networks, external storage media, a power supply, a bedside controller (e.g., which may be connected to the OCT system using Bluetooth technology or other methods known for wireless communication), etc.

Unless otherwise discussed herein, like numerals indicate like elements. For example, while variations or differences exist between the systems/apparatuses, such as, but not limited to, the system 100, the system 100', the system 100", the system 100''', the systems/apparatuses of FIGS. 3A-3G, etc. (e.g., differences between the position(s) of the reference reflection 105 (and/or reference arm 102) depending on the OCT system or method being used), one or more features thereof may be the same or similar to each other, such as, but not limited to, the light source 101, the deflecting section 108 or other component(s) thereof (e.g., the console 1200, the console 1200', etc.). Those skilled in the art will appreciate that the light source 101, the at least one detector 107 and/or one or more other elements of the system 100, may operate in the same or similar fashion to those like-numbered elements of one or more other systems, such as, but not limited to, the system 100', the system 100", the system 100'", etc. as discussed herein. Those skilled in the art will appreciate that alternative embodiments of the system 100, the system 100', the system 100", the system 100'", the systems/apparatuses of FIGS. 3A-3G, and/or one or more like-numbered elements of one of such systems, while having other variations as discussed herein, may operate in the same or similar fashion to the like-numbered elements of any of the other systems (or component(s) thereof) discussed herein. Indeed, while certain differences exist between the system 100, the system 100', the system 100", the system 100'", the systems/apparatuses of FIGS. 3A-3G, etc. as discussed herein, there are similarities between the apparatuses/systems discussed herein. Likewise, while the console or computer 1200 may be used in one or more systems (e.g., the system 100, the system 100', the system 100", the system 100'", the systems/apparatuses of FIGS. 3A-3G, any other apparatuses/systems discussed herein, etc.), one or more other consoles or computers, such as the console or computer 1200', may be used additionally or alternatively.

Figure 11:
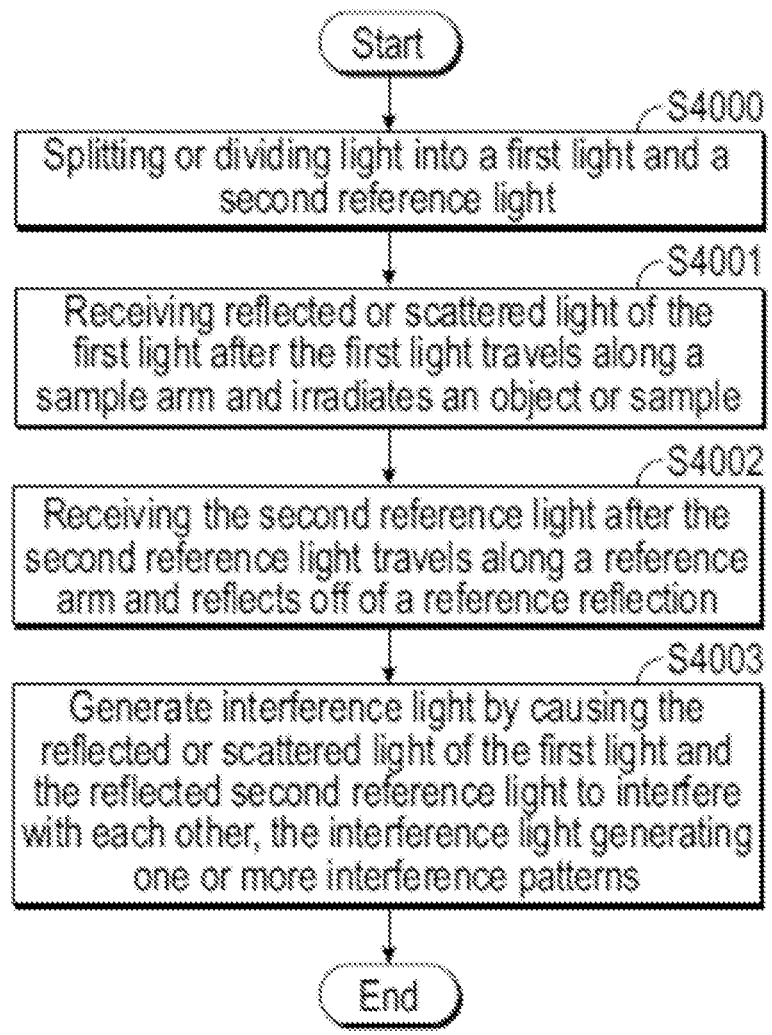
FIG. 11 is a flow diagram illustrating at least one method embodiment of performing an imaging feature, function, or technique that may be used with one or more self-diagnosis techniques and/or one or more imaging techniques in accordance with one or more aspects of the present disclosure.

In accordance with one or more aspects of the present disclosure, one or more methods for detecting and guiding optical connections are provided herein, and one or more methods for performing imaging are provided herein. FIG. 11 illustrates a flow chart of at least one embodiment of a method for performing imaging. Preferably, the method(s) may include one or more of the following: (i) splitting or dividing light into a first light and a second reference light (see step S4000 in FIG. 11); (ii) receiving reflected or scattered light of the first light after the first light travels along a sample arm and irradiates an object or a sample (see step S4001 in FIG. 11); (iii) receiving the second reference light after the second reference light travels along a reference arm and reflects off of a reference reflection (see step S4002 in FIG. 11); and (iv) generating interference light by causing the reflected or scattered light of the first light and the reflected second reference light to interfere with each other (for example, by combining or recombining and then interfering, by interfering, etc.), the interference light generating one or more interference patterns (see step S4003 in FIG. 11). One or more methods may further include using low frequency monitors to update or control high frequency content to improve image quality. For example, one or more embodiments may use balanced detection, polarization diversity, automated polarization control, etc. to achieve improved image quality. In one or more embodiments, an imaging probe may be connected to one or more systems (e.g., the system 100, the system 100', the system 100", the devices, apparatuses or systems of FIGS. 3A-3G, any other system or apparatus discussed herein, etc.) with a connection member or interface module. For example, when the connection member or interface module is a rotary junction (or rotary joint) for an imaging probe, the rotary junction may be at least one of: a contact rotary junction, a lenseless rotary junction, a lens-based rotary junction, or other rotary junction known to those skilled in the art. The rotary junction may be a one channel rotary junction or a two channel rotary junction. In one or more embodiments, the illumination portion of the imaging probe may be separate from the detection portion of the imaging probe. For example, in one or more applications, a probe may refer to the illumination assembly, which includes an illumination fiber (e.g., single mode fiber, a GRIN lens, a spacer and the grating on the polished surface of the spacer, etc.). In one or more embodiments, a scope may refer to the illumination portion which, for example, may be enclosed and protected by a drive cable, a sheath, and detection fibers (e.g., multimode fibers (MMFs)) around the sheath. Grating coverage is optional on the detection fibers (e.g., MMFs) for one or more applications. The illumination portion may be connected to a rotary joint and may be rotating continuously at video rate. In one or more embodiments, the detection portion may include one or more of: a detection fiber, a detector (e.g., the one or more detectors 107, a spectrometer, etc.), the computer 1200, the computer 1200', etc. The detection fibers may surround the illumination fiber, and the detection fibers may or may not be covered by a grating, a spacer, a lens, an end of a probe or catheter, etc.

There are many ways to compute power and/or perform one or more of the techniques, such as, but not limited to, the detecting and/or guiding, and the rotary joint health (e.g., optical health) and/or the apparatus/system health (e.g., optical health), techniques, discussed herein, digital as well as analog. In at least one embodiment, a computer, such as the console or computer 1200, 1200', may be dedicated to the control and the monitoring of the OCT devices, systems, methods and/or storage mediums described herein.

The electric signals used for imaging may be sent to one or more processors, such as, but not limited to, a computer 1200 (see e.g., FIGS. 1, 3A-3G, 8-10, and 12), a computer 1200' (see e.g., FIG. 13), etc. as discussed further below, via cable(s) or wire(s), such as, but not limited to, the cable(s) or wire(s) 113 (see FIG. 12). The computer or processor 1200, 1200' may be used instead of any other computer or processor discussed herein (e.g., the processor 1200 may be used instead of the processor 1200', the processor 1200' may be used instead of the processor 1200', the processors 1200 and 1200' may be used together, etc.). In other words, the computers or processors discussed herein are interchangeable, and may operate to perform any of the multiple imaging modalities feature(s) and method(s) or any of the other techniques or methods discussed herein. The communication interface of the computer 1200 may connect to other components discussed herein via line 113 (as diagrammatically shown in FIG. 12).

Figure 12:
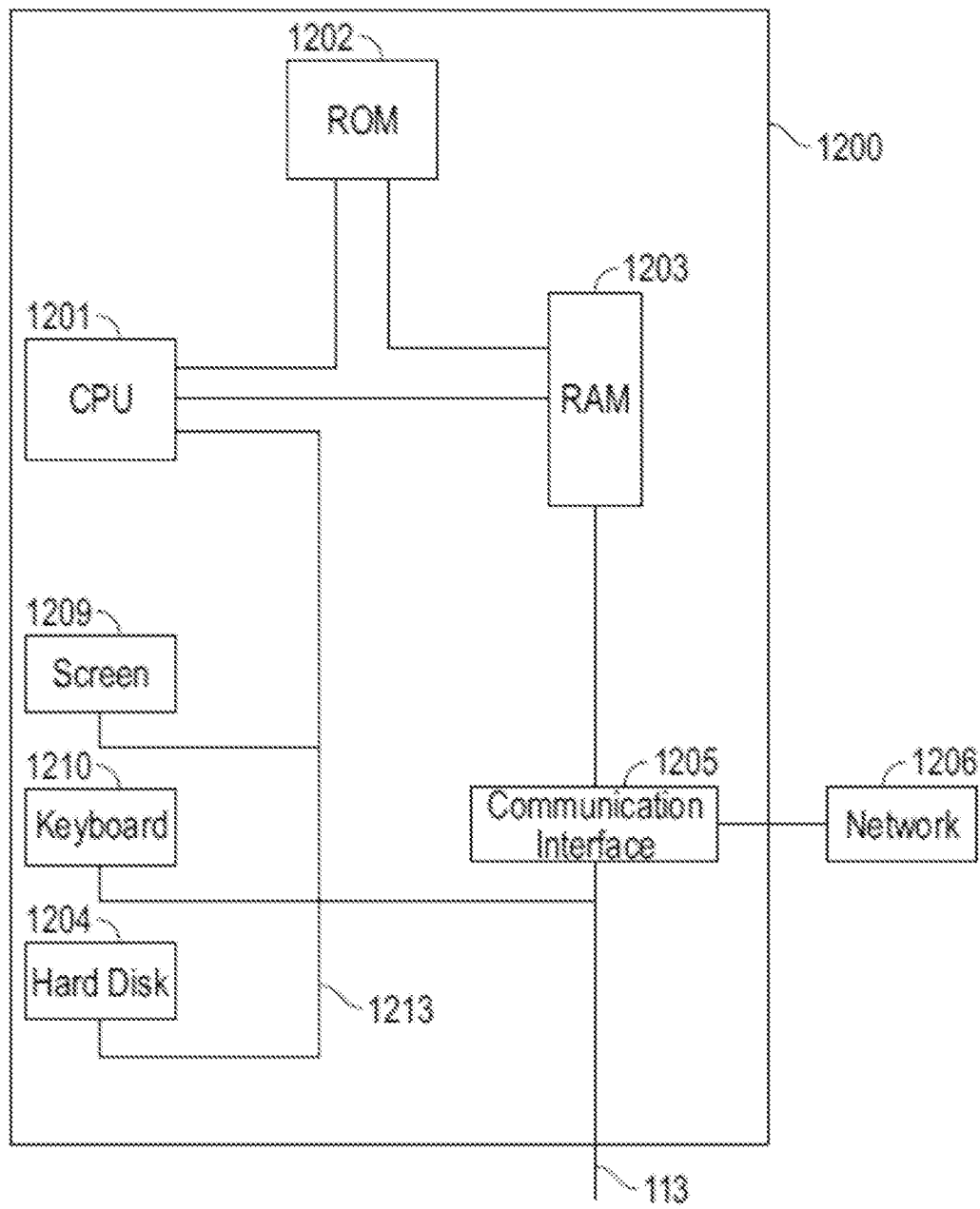
FIG. 12 shows a schematic diagram of an embodiment of a computer that may be used with one or more embodiments of at least one apparatus, system, method, and/or storage medium, including, but not limited to, for performing one or more self-diagnosis techniques and/or one or more imaging techniques in accordance with one or more aspects of the present disclosure.

Various components of a computer system 1200 (see e.g., the console or computer 1200 as shown in FIGS. 1, 3A-3G, and 8-10) are provided in FIG. 12. A computer system 1200 may include a central processing unit ("CPU") 1201, a ROM 1202, a RAM 1203, a communication interface 1205, a hard disk (and/or other storage device) 1204, a screen (or monitor interface) 1209, a keyboard (or input interface; may also include a mouse or other input device in addition to the keyboard) 1210 and a BUS or other connection lines (e.g., connection line 1213) between one or more of the aforementioned components (e.g., as shown in FIG. 12). In addition, the computer system 1200 may comprise one or more of the aforementioned components. For example, a computer system 1200 may include a CPU 1201, a RAM 1203, an input/output (I/O) interface (such as the communication interface 1205) and a bus (which may include one or more lines 1213 as a communication system between components of the computer system 1200; in one or more embodiments, the computer system 1200 and at least the CPU 1201 thereof may communicate with the one or more aforementioned components of a FORJ or a device or system using same, such as, but not limited to, the system 100, the system 100', the system 100", the system 100'", and/or the systems/apparatuses of FIGS. 3A-3G, discussed herein above, via one or more lines 1213), and one or more other computer systems 1200 may include one or more combinations of the other aforementioned components. The CPU 1201 is configured to read and perform computer-executable instructions stored in a storage medium. The computer-executable instructions may include those for the performance of the methods and/or calculations described herein. The computer system 1200 may include one or more additional processors in addition to CPU 1201, and such processors, including the CPU 1201, may be used for controlling and/or manufacturing a device, system or storage medium for use with same or for use with any lumen detection, stent(s) detection, artifact(s) detection, detecting and/or guiding optical connections, and/or the rotary joint health (e.g., optical health) determination and/or the apparatus/system health (e.g., optical health) determination technique(s) discussed herein. The system 1200 may further include one or more processors connected via a network connection (e.g., via network 1206). The CPU 1201 and any additional processor being used by the system 1200 may be located in the same telecom network or in different telecom networks (e.g., performing, manufacturing, controlling, and/or using technique(s) may be controlled remotely).

Figure 13:
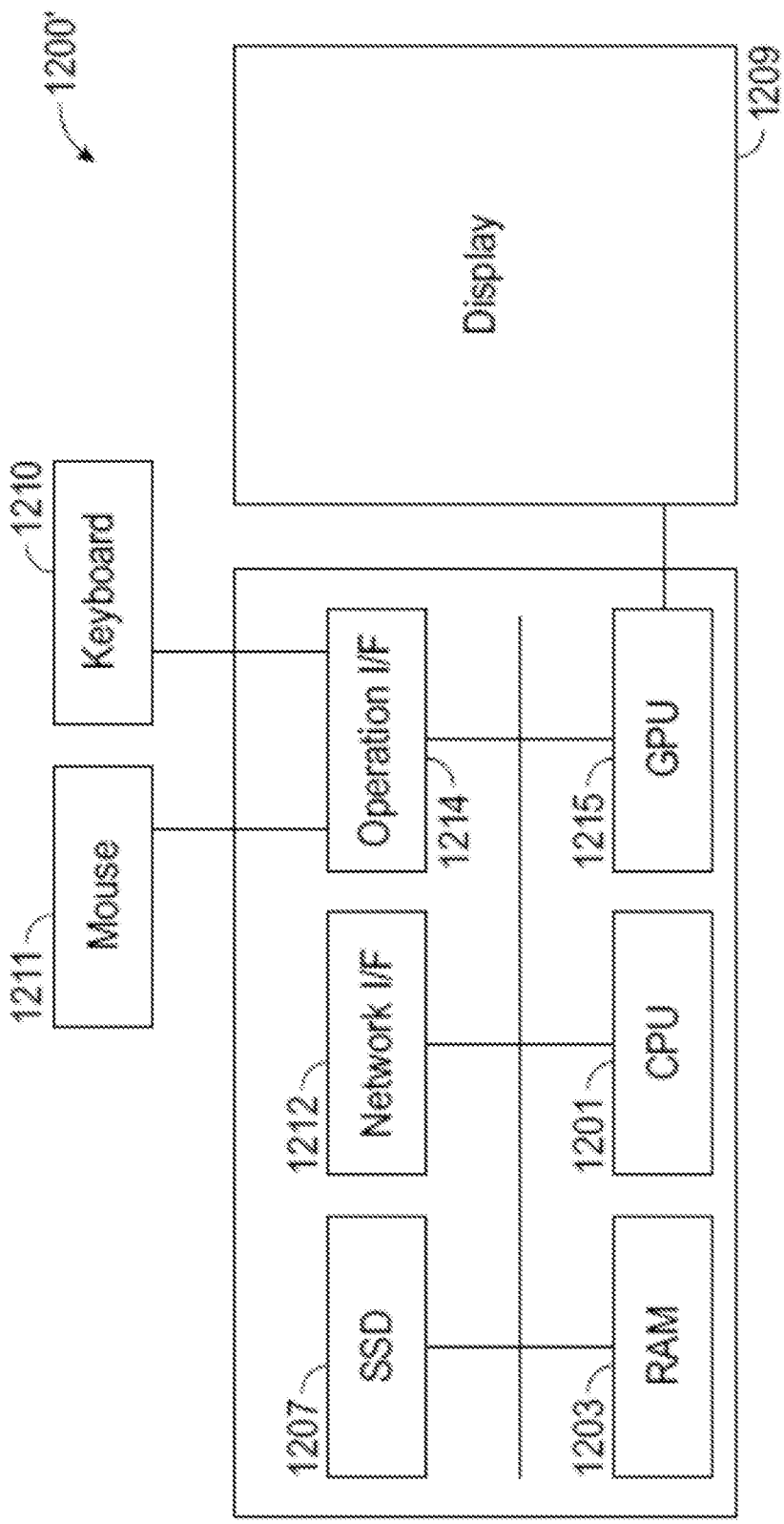
FIG. 13 shows a schematic diagram of another embodiment of a computer that may be used with one or more embodiments of at least one apparatus, system, method, and/or storage medium, including, but not limited to, for performing one or more self-diagnosis techniques and/or one or more imaging techniques in accordance with one or more aspects of the present disclosure.

The I/O or communication interface 1205 provides communication interfaces to input and output devices, which may include the light source 101, a RJ, a PM, an SM, unit 150, unit 112, a microphone, a communication cable and a network (either wired or wireless), a keyboard 1210, a mouse (see e.g., the mouse 1211 as shown in FIG. 13), a touch screen or screen 1209, a light pen and so on. The Monitor interface or screen 1209 provides communication interfaces thereto.

Any methods and/or data of the present disclosure, such as the methods for using and/or manufacturing a device, system, or storage medium for use with same and/or method(s) for detecting lumen edge(s), stent(s), and/or artifact(s), including in OCT image(s), for detecting and/or guiding optical connections, and/or for determining rotary joint/junction health (e.g., optical health) and/or apparatus/system health (e.g., optical health) as discussed herein, may be stored on a computer-readable storage medium. A computer-readable and/or writable storage medium used commonly, such as, but not limited to, one or more of a hard disk (e.g., the hard disk 1204, a magnetic disk, etc.), a flash memory, a CD, an optical disc (e.g., a compact disc ("CD") a digital versatile disc ("DVD"), a Blu-ray™ disc, etc.), a magneto-optical disk, a random-access memory ("RAM") (such as the RAM 1203), a DRAM, a read only memory ("ROM"), a storage of distributed computing systems, a memory card, or the like (e.g., other semiconductor memory, such as, but not limited to, a non-volatile memory card, a solid state drive (SSD) (see SSD 1207 in FIG. 13), SRAM, etc.), an optional combination thereof, a server/database, etc. may be used to cause a processor, such as, the processor or CPU 1201 of the aforementioned computer system 1200 to perform the steps of the methods disclosed herein. The computer-readable storage medium may be a non-transitory computer-readable medium, and/or the computer-readable medium may comprise all computer-readable media, with the sole exception being a transitory, propagating signal. The computer-readable storage medium may include media that store information for predetermined, limited, or short period(s) of time and/or only in the presence of power, such as, but not limited to Random Access Memory (RAM), register memory, processor cache(s), etc. Embodiment(s) of the present disclosure may also be realized by a computer of a system or apparatus that reads out and executes computer executable instructions (e.g., one or more programs) recorded on a storage medium (which may also be referred to more fully as a "non-transitory computer-readable storage medium") to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s).

In accordance with at least one aspect of the present disclosure, the methods, devices, systems, and computer-readable storage mediums related to the processors, such as, but not limited to, the processor of the aforementioned computer 1200, the processor of computer 1200', any other processor discussed herein, etc., as described above may be achieved utilizing suitable hardware, such as that illustrated in the figures. Functionality of one or more aspects of the present disclosure may be achieved utilizing suitable hardware, such as that illustrated in FIG. 12. Such hardware may be implemented utilizing any of the known technologies, such as standard digital circuitry, any of the known processors that are operable to execute software and/or firmware programs, one or more programmable digital devices or systems, such as programmable read only memories (PROMs), programmable array logic devices (PALs), etc. The CPU 1201 (as shown in FIG. 12 or FIG. 13) may also include and/or be made of one or more microprocessors, nanoprocessors, one or more graphics processing units ("GPUs"; also called a visual processing unit ("VPU")), one or more Field Programmable Gate Arrays ("FPGAs"), or other types of processing components (e.g., application specific integrated circuit(s) (ASIC)). Still further, the various aspects of the present disclosure may be implemented by way of software and/or firmware program(s) that may be stored on suitable storage medium (e.g., computer-readable storage medium, hard drive, solid state drive, hybrid hard drive, etc.) or media (such as floppy disk(s), memory chip(s), etc.) for transportability and/or distribution. The computer may include a network of separate computers or separate processors to read out and execute the computer executable instructions. The computer executable instructions may be provided to the computer, for example, from a network or the storage medium. The computers or processors (e.g., 1200, 1200', any other computers or processors discussed herein, etc.) may include the aforementioned CPU structure, or may be connected to such CPU structure for communication therewith.

As aforementioned, hardware structure of an alternative embodiment of a computer or console 1200' is shown in FIG. 13. The computer 1200' includes a central processing unit (CPU) 1201, a graphical processing unit (GPU) 1215, a random access memory (RAM) 1203, a network interface device 1212, an operation interface 1214 such as a universal serial bus (USB) and a memory such as a hard disk drive or a solid-state drive (SSD) 1207. Preferably, the computer or console 1200' includes a display 1209. The computer 1200' may connect with a rotary junction (e.g., RJ of FIG. 8, RJ of FIG. 10, etc.), the motor PM, the motor SM, and/or one or more other components of a system (e.g., the system 100, the system 100', the system 100", the system 100''', the systems/apparatuses of FIGS. 3A-3G, etc.) via the operation interface 1214 or the network interface 1212. A computer, such as the computer 1200, 1200', may include the RJ, the PM, and/or the SM in one or more embodiments. The computer 1200' may connect with a motor, a console, or any other component of the device(s) or system(s) discussed herein via the operation interface 1214 or the network interface 1212 (e.g., via a cable or fiber, such as the cable or fiber 113 as similarly shown in FIG. 12). A computer, such as the computer 1200', may include a motor or motion control unit (MCU) in one or more embodiments. The operation interface 1214 is connected with an operation unit such as a mouse device 1211, a keyboard 1210 or a touch panel device. The computer 1200' may include two or more of each component. Alternatively, the CPU 1201 or the GPU 1215 may be replaced by the field-programmable gate array (FPGA), the application-specific integrated circuit (ASIC) or other processing unit depending on the design of a computer, such as the computer 1200, the computer 1200', any other computer or processor discussed herein, etc.

A computer program is stored in the SSD 1207, and the CPU 1201 loads the program onto the RAM 1203, and executes the instructions in the program to perform one or more processes described herein, as well as the basic input, output, calculation, memory writing and memory reading processes.

The computer, such as the computer 1200, 1200', communicates with the PIU 110, the rotary junction (e.g., the RJ, etc.), the motor PM, the motor SM, the catheter 120 and/or one or more other components of a system, such as the system 100, 100', 100", 100''', etc., to perform imaging, and reconstructs an image from the acquired intensity data. The monitor or display 1209 displays the reconstructed image, and may display other information about the imaging condition or about an object to be imaged. The monitor 1209 also provides a graphical user interface for a user to operate a system (e.g., the system 100, the system 100', the system 100", the system 100''', etc.), for example when performing OCT or other imaging technique, including, but not limited to, detection of lumen edge(s) and/or artifact(s), detecting and/or guiding optical connections, determining or evaluating rotary joint health (e.g., optical health) and/or apparatus/system health (e.g., optical health), etc. An operation signal is input from the operation unit (e.g., such as, but not limited to, a mouse device 1211, a keyboard 1210, a touch panel device, etc.) into the operation interface 1214 in the computer 1200', and corresponding to the operation signal the computer 1200' instructs the system (e.g., the system 100, the system 100', the system 100", the system 100''', the systems/apparatuses of FIGS. 3A-3G, etc.) to set or change the imaging condition, and to start or end the imaging, and/or to start or end the lumen detection, stent(s) detection, artifact(s) detection, detection and/or guidance of optical connection(s), and/or determination or evaluation of rotary joint health (e.g., optical health) and/or apparatus/system health (e.g., optical health). The laser source 101 of an OCT system as aforementioned may have interfaces to communicate with the computers 1200, 1200' to send and receive the status information and the control signals.

While not limited to such arrangements, configurations, devices or systems, one or more embodiments of the devices, apparatuses, systems, methods, storage mediums, etc. discussed herein may be used with an apparatus or system as aforementioned, such as, but not limited to, for example, the system 100, the system 100', the system 100", the system 100''', the devices, apparatuses, or systems of FIGS. 1-10 and 12-13, any other device, apparatus or system discussed herein, etc. In one or more embodiments, one user may perform the method(s) discussed herein. In one or more embodiments, one or more users may perform the method(s) discussed herein. In one or more embodiments, one or more of the computers, CPUs, processors, etc. discussed herein may be used to process, control, update, emphasize, and/or change one or more of the imaging modalities, and/or process the related techniques, functions or methods, or may process the electrical signals as discussed above.

Additionally, unless otherwise specified, the term "subset" of a corresponding set does not necessarily represent a proper subset and may be equal to the corresponding set.

The present disclosure and/or one or more components of devices, systems and storage mediums, and/or methods, thereof also may be used in conjunction with optical coherence tomography probes. Such probes include, but are not limited to, the OCT imaging systems disclosed in U.S. Pat. Nos. 6,763,261; 7,366,376; 7,843,572; 7,872,759; 8,289,522; 8,676,013; 8,928,889; 9,087,368; 9,557,154; 10,912,462; 9,795,301; and 9,332,942 to Tearney et al. and arrangements and methods of facilitating photoluminescence imaging, such as those disclosed in U.S. Pat. No. 7,889,348 to Tearney et al., as well as the disclosures directed to multimodality imaging disclosed in U.S. Pat. No. 9,332,942 and U.S. Patent Publication Nos. 2010/0092389, 2011/0292400, 2012/0101374, 2014/0276011, 2017/0135584, 2016/0228097, 2018/0045501 and 2018/0003481, WO 2016/015052 to Tearney et al. and WO 2016/144878, each of which patents, patent publications and patent application(s) are incorporated by reference herein in their entireties. As aforementioned, any feature or aspect of the present disclosure may be used with OCT imaging systems, apparatuses, methods, storage mediums or other aspects or features as discussed in U.S. patent application Ser. No. 16/414,222, filed on May 16, 2019, the entire disclosure of which is incorporated by reference herein in its entirety, as discussed in U.S. Pat. Pub. No. 2019/0374109, which was published on Dec. 12, 2019, the disclosure of which is incorporated by reference herein in its entirety, as discussed in U.S. Pat. App. No. 62/944,064, filed on Dec. 5, 2019, the disclosure of which is incorporated by reference herein in its entirety, as discussed in U.S. Pat. Pub. No. 2021/0077037, published on Mar. 18, 2021, as discussed in U.S. Pat. Pub. No. 2021/0174125, published on Jun. 10, 2021, and as discussed in U.S. patent application Ser. No. 17/098,042, filed on Nov. 13, 2020, the disclosure of which is incorporated by reference herein in its entirety.

The present disclosure and/or one or more components of devices, systems, and storage mediums, and/or methods, thereof also may be used in conjunction with OCT imaging systems and/or catheters and catheter systems, such as, but not limited to, those disclosed in U.S. Pat. Nos. 9,869,828; 10,323,926; 10,558,001; 10,601,173; 10,606,064; 10,743,749; 10,884,199; 10,895,692; and 11,175,126 as well as U.S. Patent Publication Nos. 2019/0254506; 2020/0390323; 2021/0121132; 2021/0174125; 2022/0040454; 2022/0044428; and WO2021/055837, each of which patents and patent publications are incorporated by reference herein in their entireties.

Although the disclosure herein has been described with reference to particular embodiments, it is to be understood that these embodiments are merely illustrative of the principles and applications of the present disclosure (and are not limited thereto). It is therefore to be understood that numerous modifications may be made to the illustrative embodiments and that other arrangements may be devised without departing from the spirit and scope of the present disclosure. The scope of the following claims is to be accorded the broadest interpretation so as to encompass all such modifications, equivalent structures and functions.

What is claimed is:

1. An interferometry and/or Optical Coherence Tomography (OCT) system that operates to determine a health of one or more internal components of the interferometry and/or OCT system and/or to determine a health of the interferometry and/or OCT system, comprising:

an imaging apparatus or system using one or more imaging modalities;

at least one reference reflection that operates so that a reflection from a portion of the one or more internal components of the interferometry and/or OCT system is visible in an observable imaging depth or in an imaging field of view; and one or more processors that operate to determine the health of the one or more internal components and/or the health of the interferometry and/or OCT system based on one or more interferometry signals and/or images.

2. The interferometry and/or OCT system of claim 1, further compromising a catheter or probe.

3. The interferometry and/or OCT system of claim 2, wherein the one or more internal components includes one or more of the following: a mating part of the catheter or probe; a portion of the catheter or probe; a rotary joint of a Patient Interface Unit (PIU); a rotary joint of the interferometry and/or OCT system; a portion of the PIU; and/or a sacrificial interface in communication with a rotary joint of the interferometry and/or OCT system or in communication with the interferometry and/or OCT system.

4. The interferometry and/or OCT system of claim 1, where the interferometry and/or OCT system or the one or more processors further operate to:

switch the at least one reference reflection from a main reference arm to an auxiliary reference arm; and adjust the auxiliary reference arm such that one or more reflections from one or more optical surfaces of the rotary joint or of the one or more internal components are disposed or located in the observable imaging depth or in the imaging field of view.

5. The interferometry and/or OCT system of claim 4, wherein the interferometry and/or OCT system or the one or more processors further operate to determine the health of the one or more internal components and/or the health of the interferometry and/or OCT system, based on the one or more interferometry signals and/or the images, by characterizing or using one or more of the following: one or more return losses, a noise floor, one or more fixed pattern artifacts, and/or point spread functions (PSF) width.

6. The interferometry and/or OCT system of claim 5, wherein the one or more processors further operate to:

perform peak finding to identify one or more peaks related or relating to one of the following: (i) one or more return signals that return from one or more predetermined locations on the one or more internal components, a rotary joint of the one or more internal components, and/or the interferometry and/or OCT system; and/or (ii) the one or more interferometry signals and/or the images; and determine the health of the one or more internal components or the rotary joint of the interferometry and/or OCT system using the identified one or more peaks and/or determine the health of the interferometry and/or OCT system using the identified one or more peaks.

7. The interferometry and/or OCT system of claim 4, wherein the one or more processors further operate to one or more of the following:

(i) store the determined health of the one or more internal components or of a rotary joint of the one or more internal components and/or the determined health of the interferometry and/or OCT system in one or more memories; and/or (ii) display the determined health of the one or more internal components or of a rotary joint of the one or more internal components and/or the determined health of the interferometry and/or OCT system on a display of the interferometry and/or OCT system or on a display in communication with the interferometry and/or OCT system.

8. The interferometry and/or OCT system of claim 4, wherein:

in a case where a delay of an optical delay line is increased or adjusted so that a length of the main reference arm or of the auxiliary reference arm matches a length of a sample arm of the interferometry and/or OCT system and of a catheter or probe included, the interferometry and/or OCT system operates or the one or more processors operate to perform system imaging; or in a case where the delay is decreased or adjusted so that a length of the main reference arm or of the auxiliary reference arm matches a length of a sample arm of the interferometry and/or OCT system without the catheter or probe, the interferometry and/or OCT system operates or the one or more processors operate to perform imaging of a region of the one or more internal components, the rotary joint, or of one or more portions of the rotary joint or of the one or more internal components.

9. The interferometry and/or OCT system of claim 4, further comprising one of the following:

(i) an optical delay line or an optical switch that operates such that the one or more processors switch the at least one reference reflection between the main reference arm and the auxiliary reference arm;

(ii) an optical switch, wherein the at least one reference reflection comprises a main reflector for the main reference arm and an auxiliary reflector for the auxiliary reference arm, and the optical switch operates to switch between the main reflector of the main reference arm and the auxiliary reflector of the auxiliary reference arm;

(iii) a 1×2 optical switch, wherein the at least one reference reflection comprises a main reflector for the main reference arm and an auxiliary reflector for the auxiliary reference arm, and the 1×2 optical switch operates to switch between the main reflector of the main reference arm and the auxiliary reflector of the auxiliary reference arm;

(iv) an optical switch, wherein the at least one reference reflection comprises an optical delay line for the main reference arm and an auxiliary reflector for the auxiliary reference arm, the optical switch operates to switch between the optical delay line of the main reference arm and the auxiliary reflector of the auxiliary reference arm, and the optical delay line operates to adjust a length of the main reference arm to account for an optical probe or catheter with varying optical lengths;

(v) an optical switch, wherein the at least one reference reflection comprises a main reflector for the main reference arm and an optical delay line for the auxiliary reference arm, the optical switch operates to switch between the main reflector of the main reference arm and the optical delay line of the auxiliary reference arm, and the optical delay line operates to adjust a length of the auxiliary reference arm to account for an optical probe or catheter with varying optical lengths;

(vi) an optical switch and an optical delay line, wherein the at least one reference reflection comprises a main reflector for the main reference arm and an auxiliary reflector for the auxiliary reference arm, the optical switch operates to switch between the main reflector of the main reference arm and the auxiliary reflector of the auxiliary reference arm, and the optical delay line is in communication with the optical switch such that the optical delay line operates to adjust a length of the main reference arm and/or the auxiliary reference arm to account for a catheter or probe with a varying optical length and/or to address one or more manufacturing tolerances of the interferometry and/or OCT system or of a portion of the interferometry and/or OCT system;

(vii) two optical switches in communication with each other in series, the two optical switches operating to define an auxiliary path portion of the auxiliary reference arm and a main path portion of the main reference arm, the two optical switches being in further communication with the at least one reference reflection or an optical delay line such that the auxiliary path or the main path is used for the reference reflection or the optical delay line;

(viii) an optical switch and an optical delay line, wherein the at least one reference reflection comprises a main reflector for the main reference arm and an auxiliary reflector for the auxiliary reference arm, the optical switch operates to switch between the main reflector of the main reference arm and the auxiliary reflector of the auxiliary reference arm, the optical delay line is in communication with the optical switch such that the optical switch is disposed in between the optical delay line and the main and auxiliary reflectors, and the optical delay line operates to adjust a length of the main reference arm and/or the auxiliary reference arm; or (ix) an optical delay line and a light splitter, wherein the at least one reference reflection comprises a main reflector for the main reference arm and an auxiliary reflector for the auxiliary reference arm, the splitter operates to split light or one or more signals between the main reflector of the main reference arm and the auxiliary reflector of the auxiliary reference arm at the same time.

10. The interferometry and/or OCT system of claim 9, further comprising one or more of the following:

(i) a 3-port circulator that is connected to or in communication with, or that operates to transmit one or more signals between, the following: a light source via a first port of the 3-port circulator, the main reference arm and/or the auxiliary reference arm via a second port of the 3-port circulator, and one or more detectors via a third port of the 3-port circulator;

(ii) a 4-port circulator that is connected to or in communication with, or that operates to transmit one or more signals between, the following: a light source via a first port of the 4-port circulator, the main reference arm and/or the auxiliary reference arm via a second port of the 4-port circulator, one or more detectors via a third port of the 4-port circulator, and an optical delay line via a fourth port of the 4-port circulator; and/or (iii) another 3-port circulator connected to or included in a sample arm of the interferometry and/or OCT system, the other 3-port circulator being connected to or in communication with, or operating to transmit one or more signals between, the following: a light source via a first port of the another 3-port circulator, the rotary joint or a catheter or probe connected to the rotary joint via a second port of the another 3-port circulator, and one or more detectors via a third port of the another 3-port circulator.

11. The interferometry and/or OCT system of claim 1, wherein the one or more processors further operate to control one or more of the following: (i) a mechanical mating of a sacrificial interface of a rotary joint of the interferometry and/or OCT system, of the one or more internal components of the interferometry and/or OCT system, of a patient interface unit of the interferometry and/or OCT system, or of the interferometry and/or OCT system to a connector of a catheter or probe; and/or (ii) a mechanical de-mating of a connector of a catheter or probe from one of the following: a sacrificial interface of the rotary joint of the interferometry and/or OCT system, the one or more internal components of the interferometry and/or OCT system, a patient interface unit of the interferometry and/or OCT system, or the interferometry and/or OCT system.

12. The interferometry and/or OCT system of claim 1, further comprising a linear stage and a rotary motor, wherein the one or more processors further operate to move the linear stage and the rotary motor to one or more positions such that the reflection from the portion of the one or more internal components of the interferometry and/or OCT system is visible in the observable imaging depth or the imaging field of view.

13. The interferometry and/or OCT system of claim 1, further comprising, or being connected to, one or more of the following:

(a) a light source that operates to produce a light;

(b) an interference optical system that operates to: (i) receive and divide the light from the light source into a first light with which an object or sample is to be irradiated and a second reference light, (ii) send the second reference light for reflection off of a reference mirror of the interference optical system or off of the at least one reference reflection, and (iii) generate interference light by causing reflected or scattered light of the first light with which the object or sample has been irradiated and the reflected second reference light to combine or recombine, and to interfere, with each other, the interference light generating one or more interference patterns; and/or (c) an interference optical system and one or more detectors, the interference optical system operating to: (i) receive and divide the light from the light source into a first light with which an object or sample is to be irradiated and a second reference light, (ii) send the second reference light for reflection off of a reference mirror of the interference optical system or off of the at least one reference reflection, and (iii) generate interference light by causing reflected or scattered light of the first light with which the object or sample has been irradiated and the reflected second reference light to combine or recombine, and to interfere, with each other, the interference light generating one or more interference patterns, and the one or more detectors operating to continuously acquire the interference light and/or the one or more interference patterns such that the one or more interferometry signals and/or the images is/are obtained.

14. The interferometry and/or OCT system of claim 1, wherein the one or more imaging modalities include one or more of the following: Optical Coherence Tomography (OCT); another lumen image(s) modality; an intravascular imaging modality; an imaging modality for fluorescence; a near-infrared auto-fluorescence (NIRAF) imaging modality; a near-infrared auto-fluorescence (NIRAF) imaging modality in a predetermined view, a carpet view, and/or an indicator view; a near-infrared fluorescence (NIRF) imaging modality; a near-infrared fluorescence (NIRF) imaging modality in a predetermined view, a carpet view, and/or an indicator view; a three-dimensional (3D) rendering imaging modality; an imaging modality for a 3D rendering of a vessel; an imaging modality for a 3D rendering of a vessel in a half-pipe view or display; an imaging modality for a 3D rendering of an object, target, or specimen; an imaging modality for a lumen profile; an imaging modality for a lumen diameter display; an imaging modality for a longitudinal view; computer tomography (CT); Magnetic Resonance Imaging (MRI); Intravascular Ultrasound (IVUS); an imaging modality for an X-ray image or view; and an imaging modality for an angiography view.

15. A method for determining a health of an interferometry and/or Optical Coherence Tomography (OCT) apparatus or system or one or more internal components of the interferometry and/or OCT apparatus or system, the interferometry and/or OCT apparatus or system comprising an imaging apparatus or system using one or more imaging modalities, and at least one reference reflection that operates so that a reflection from a portion of the one or more internal components of the interferometry and/or OCT apparatus or system is visible in an observable imaging depth or in an imaging field of view, the method comprising:
   determining the health of the one or more internal components and/or the health of the interferometry and/or OCT apparatus or system based on one or more interferometry signals and/or images.

16. The method of claim 15, wherein one or more of the following:
   the interferometry and/or OCT apparatus or system further includes a catheter or probe; and/or
   the one or more internal components includes one or more of the following: a mating part of the catheter or probe; a portion of the catheter or probe; a rotary joint of a Patient Interface Unit (PIU); a rotary joint of the interferometry and/or OCT apparatus or system; a portion of the PIU; and/or a sacrificial interface in communication with a rotary joint of the interferometry and/or OCT apparatus or system or in communication with the interferometry and/or OCT apparatus or system.

17. The method of claim 15, further comprising:
   switching the at least one reference reflection from a main reference arm to an auxiliary reference arm; and
   adjusting the auxiliary reference arm such that one or more reflections from one or more optical surfaces of a rotary joint or of the one or more internal components are disposed or located in the observable imaging depth or in the imaging field of view.

18. The method of claim 17, wherein the interferometry and/or OCT apparatus or system further operates to determine the health of the one or more internal components and/or the health of the interferometry and/or OCT apparatus or system, based on the one or more interferometry signals and/or the images, by characterizing or using one or more of the following: one or more return losses, a noise floor, one or more fixed pattern artifacts, and/or point spread functions (PSF) width.

19. The method of claim 18, further comprising:
   performing peak finding to identify one or more peaks related or relating to one of the following: (i) one or more return signals that return from one or more predetermined locations on the one or more internal components, a rotary joint of the one or more internal components, and/or the interferometry and/or OCT apparatus/system; and/or (ii) the one or more interferometry signals and/or the images; and
   determining the health of the one or more internal components or the rotary joint of the interferometry and/or OCT apparatus or system using the identified one or more peaks and/or determining the health of the interferometry and/or OCT apparatus/system using the identified one or more peaks.

20. The method of claim 17, further comprising one or more of the following:
   (i) storing the determined health of the one or more internal components or of a rotary joint of the one or more internal components and/or the determined health of the interferometry and/or OCT apparatus/system in one or more memories; and/or
   (ii) displaying the determined health of the one or more internal components or of a rotary joint of the one or more internal components and/or the determined health of the interferometry and/or OCT apparatus/system on a display of the interferometry and/or OCT apparatus/system or on a display in communication with the interferometry and/or OCT apparatus/system.

21. The method of claim 17, wherein the determining the health of the one or more internal components using the identified one or more peaks and/or the determining the health of the interferometry and/or OCT apparatus/system using the identified one or more peaks step further comprises one or more of the following:
   (i) calculating a value of a selected peak or peaks of the identified one or more peaks and comparing the value of the selected peak or peaks to a measured a measured signal-to-noise ratio (SNR);
   (ii) calculating a sensitivity value by calculating a value of a selected peak or peaks of the identified one or more peaks and subtracting a return loss of the selected peak or peaks from a measured signal-to-noise ratio (SNR);
   (iii) using a differential value between a rotatable section of the one or more internal components or of a rotary joint of the one or more internal components and a stationary or fixed section of the one or more internal components or of a rotary joint of the one or more internal components to determine a change in insertion loss across the one or more internal components or of a rotary joint of the one or more internal components;
   (iv) obtaining insertion loss rotation variation by rotating a rotatable section of one or more internal components or of a rotary joint of the one or more internal components and by measuring insertion loss at two or more discrete or different angles, or by measuring insertion loss as the rotatable section of the one or more internal components or of a rotary joint of the one or more internal components is continuously rotated;
   (v) using a peak or peaks corresponding to predetermined or set location or locations of the one or more internal components or of a rotary joint of the one or more internal components and/or the interferometry and/or OCT apparatus/system to determine a health at each corresponding location or locations of the one or more internal components or of a rotary joint of the one or more internal components and/or the interferometry and/or OCT apparatus/system;

(vi) calculating a resolution for the identified one or more peaks and/or calculating a sensitivity for the identified one or more peaks, where sensitivity is measured by subtracting a return loss (RL) for a specific peak or peaks from a measured, predetermined or set signal-to-noise ratio (SNR), and where resolution is measured or determined by identifying or obtaining a width of a peak point spread function (PSF) at a specific percent or decibel (dB) reduction from a maximum peak value;

(vii) placing a peak reflection at a specific depth or location, within a predetermined deviation range, in the imaging depth range or in the imaging field of view, and calculating the sensitivity, the resolution, or both of the sensitivity and the resolution;

(viii) determining a noise floor, or determining a noise floor as the mean of a predetermined or selected A-line of the one or more interferometry signals and/or images, the median of a set of A-lines of the one or more interferometry signals and/or images, or the mean or the median of a subset of A-line(s) of the one or more interferometry signals and/or images;

(ix) determining a noise floor, or determining a noise floor as the mean of a predetermined or selected A-line of the one or more interferometry signals and/or images, the median of a set of A-lines of the one or more interferometry signals and/or images, or the mean or the median of a subset of A-line(s) of the one or more interferometry signals and/or images, where the subset of the A-line(s) is a set number of samples with a smallest amplitude or a specific number of samples about, or a fixed distance away from, the specific peak or peaks;

(x) calculating a resolution for the identified one or more peaks and/or calculating a sensitivity for the identified one or more peaks, where sensitivity is measured by subtracting a return loss (RL) for a specific peak or peaks from a measured, predetermined or set signal-to-noise ratio (SNR), where resolution is measured or determined by identifying or obtaining a width of a peak point spread function (PSF) at a specific percent or decibel (dB) reduction from a maximum peak value, and where the RL value is corrected by an insertion loss (IL) amount up to the specific peak or peaks; and/or (xi) comparing a predetermined or set signal-to-noise ratio (SNR) of a selected peak or peaks of the identified one or more peaks with a measured signal-to-noise ratio (SNR) to see whether the values of the predetermined or set SNR and the measured SNR are the same or similar to indicate an acceptable health of the rotary joint and/or the apparatus/system or to see whether the difference in values of the predetermined or set SNR and the measured SNR exceeds a set amount or threshold to indicate an unacceptable health of the one or more internal components or a rotary joint of the one or more internal components and/or the interferometry and/or OCT apparatus/system.

22. The method of claim 17, further comprising:

(i) measuring a current return loss (RL) and comparing the measured current RL to a characterized, determined, or obtained return loss (RL) to determine whether the current RL is the same as, or different from, the characterized, determined, or obtained return loss (RL); and (ii) in a case where the current RL is the same as the characterized, determined, or obtained return loss (RL), then determining that the one or more internal components or a rotary joint of the one or more internal components and/or the interferometry and/or OCT apparatus/system or portion of the interferometry and/or OCT apparatus/system corresponding to the measured return loss is healthy, or, in a case where the current RL is different than the characterized, determined, or obtained return loss (RL), then determining that the health of the one or more internal components or of the rotary joint of the one or more internal components and/or the health of the interferometry and/or OCT apparatus/system or portion of the interferometry and/or OCT apparatus/system corresponding to the measured return loss is in question, and performing additional evaluation to determine whether one or more optics are misaligned or dirty.

23. The method of claim 22, wherein the characterized, determined or obtained RL is a value recorded during or after manufacture of the interferometry and/or OCT apparatus or system.

24. The method of claim 17, further comprising using a reflection from a predetermined surface of the one or more internal components, of a rotary joint of the one or more internal components, and/or of the interferometry and/or OCT apparatus or system to assess whether an endface of the predetermined surface, of the one or more internal components or of the rotary joint, and/or of a patient interface unit housing the one or more internal components or the rotary joint is dirty by tracking an absolute return loss (absolute RL) signal before and/or after each probe or catheter engagement/disengagement process that is performed for the interferometry and/or OCT apparatus or system, where the absolute RL is defined by the return loss (RL) measured at a peak or peaks taking into account any different insertion losses up to that point in the interferometry and/or OCT apparatus or system.

25. A non-transitory computer-readable storage medium storing at least one program for causing a computer to execute a method for determining a health of an interferometry and/or Optical Coherence Tomography (OCT) apparatus or system or one or more internal components of the interferometry and/or OCT apparatus or system, the interferometry and/or OCT apparatus or system comprising an imaging apparatus or system using one or more imaging modalities, and at least one reference reflection that operates so that a reflection from a portion of the one or more internal components of the interferometry and/or OCT apparatus or system is visible in an observable imaging depth or in an imaging field of view, the method comprising:

determining the health of the one or more internal components and/or the health of the interferometry and/or OCT apparatus or system based one or more interferometry signals and/or images.

26. The non-transitory computer-readable storage medium of claim 25, wherein one or more of the following:

the interferometry and/or OCT apparatus or system further includes a catheter or probe; and/or the one or more internal components includes one or more of the following: a mating part of the catheter or probe; a portion of the catheter or probe; a rotary joint of a Patient Interface Unit (PIU); a rotary joint of the interferometry and/or OCT apparatus or system; a portion of the PIU; and/or a sacrificial interface in communication with a rotary joint of the interferometry and/or OCT apparatus or system or in communication with the interferometry and/or OCT apparatus or system.

27. The non-transitory computer-readable storage medium of claim 25, wherein the method further comprises:
switching the at least one reference reflection from a main reference arm to an auxiliary reference arm; and
adjusting the auxiliary reference arm such that one or more reflections from one or more optical surfaces of a rotary joint or of the one or more internal components are disposed or located in the observable imaging depth or in the imaging field of view.

28. The non-transitory computer-readable storage medium of claim 27, wherein the interferometry and/or OCT apparatus or system further operates to determine the health of the one or more internal components and/or the health of the interferometry and/or OCT apparatus or system, based on the one or more interferometry signals and/or the images, by characterizing or using one or more of the following: one or more return losses, a noise floor, one or more fixed pattern artifacts, and/or point spread functions (PSF) width.

29. The non-transitory computer-readable storage medium of claim 28, wherein the method further comprises:
performing peak finding to identify one or more peaks related or relating to one of the following: (i) one or more return signals that return from one or more predetermined locations on the one or more internal components, a rotary joint of the one or more internal components, and/or the interferometry and/or OCT apparatus/system; and/or (ii) the one or more interferometry signals and/or the images; and
determining the health of the one or more internal components or the rotary joint of the interferometry and/or OCT apparatus or system using the identified one or more peaks and/or determining the health of the interferometry and/or OCT apparatus/system using the identified one or more peaks.

30. The non-transitory computer-readable storage medium of claim 27, wherein the method further comprises one or more of the following:
(i) storing the determined health of the one or more internal components or of a rotary joint of the one or more internal components and/or the determined health of the interferometry and/or OCT apparatus/system in one or more memories; and/or
(ii) displaying the determined health of the one or more internal components or of a rotary joint of the one or more internal components and/or the determined health of the interferometry and/or OCT apparatus/system on a display of the interferometry and/or OCT apparatus/system or on a display in communication with the interferometry and/or OCT apparatus/system.

31. The interferometry and/or OCT system of claim 1, wherein the interferometry and/or OCT system or the one or more processors further operate to determine the health of the one or more internal components and/or the health of the interferometry and/or OCT system, based on the one or more interferometry signals and/or the images, by characterizing or using one or more of the following: one or more return losses, a noise floor, one or more fixed pattern artifacts, and/or point spread functions (PSF) width.

* * * * *